US012759984B2

(12) United States Patent
Choi et al.

(10) Patent No.: US 12,759,984 B2
(45) Date of Patent: Oct. 13, 2026

(54) ORGANIC LIGHT EMITTING DEVICE

(71) Applicant: LG Display Co., Ltd., Seoul (KR)

(72) Inventors: Su-Na Choi, Paju-si (KR); In-Bum Song, Paju-si (KR); Jeong-Dae Seo, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 1299 days.

(21) Appl. No.: 17/520,606

(22) Filed: Nov. 5, 2021

(65) Prior Publication Data

US 2022/0216409 A1 Jul. 7, 2022

(30) Foreign Application Priority Data

Dec. 28, 2020 (KR) ........................ 10-2020-0184955

(51) Int. Cl.

*C07D 251/24* (2006.01)
*C07C 15/28* (2006.01)
(Continued)

(52) U.S. Cl.

CPC ............ *C07D 251/24* (2013.01); *C07C 15/28* (2013.01); *C07C 211/61* (2013.01);
(Continued)

(58) Field of Classification Search

CPC ............... H01L 51/008; H01L 51/5016; H01L 51/0058; H01L 51/0073; H01L 51/0052;
(Continued)

(56) References Cited

U.S. PATENT DOCUMENTS

| | | | | |
|---|---|---|---|---|
| 11,482,675 B1 | 10/2022 | Tasaki et al. | | |
| 2012/0126208 A1* | 5/2012 | Kawamura | ........ | H10K 85/6576 257/E51.026 |

(Continued)

FOREIGN PATENT DOCUMENTS

| | | |
|---|---|---|
| KR | 10-2020-0081986 A | 7/2020 |
| KR | 10-2020-0132752 A | 11/2020 |

(Continued)

OTHER PUBLICATIONS

Korean Intellectual Property Office, Office Action, Korean Patent Application No. 10-2020-0184955, Dec. 6, 2024, 34 pages.

(Continued)

*Primary Examiner* — Benjamin L Utech
(74) *Attorney, Agent, or Firm* — Fenwick & West LLP

(57) ABSTRACT

The present disclosure relates to an organic light emitting device that includes a substrate, and an organic light emitting diode positioned on the substrate and including a first electrode, a second electrode facing the first electrode, a first emitting material layer including a first dopant of a boron derivative and a first host of an anthracene derivative and positioned between the first and second electrodes, a first electron blocking layer including an electron blocking material and positioned between the first electrode and the first emitting material layer, and a first hole blocking layer including a hole blocking material and positioned between the second electrode and the first emitting material layer, wherein the first host is deuterated.

17 Claims, 5 Drawing Sheets

100

(51) Int. Cl.

| | |
|---|---|
| ***C07C 211/61*** | (2006.01) |
| ***C07D 209/86*** | (2006.01) |
| ***C07D 307/77*** | (2006.01) |
| ***C07D 307/91*** | (2006.01) |
| ***C07D 333/76*** | (2006.01) |
| ***C07D 401/10*** | (2006.01) |
| ***C07D 401/14*** | (2006.01) |
| ***C07D 403/10*** | (2006.01) |
| ***C07D 403/14*** | (2006.01) |
| ***C07D 471/10*** | (2006.01) |
| ***C07F 5/02*** | (2006.01) |
| ***C09K 11/06*** | (2006.01) |
| ***H10K 50/11*** | (2023.01) |
| ***H10K 50/13*** | (2023.01) |
| ***H10K 50/18*** | (2023.01) |
| ***H10K 50/19*** | (2023.01) |
| ***H10K 85/60*** | (2023.01) |
| ***H10K 101/10*** | (2023.01) |
| *H10K 59/12* | (2023.01) |

(52) U.S. Cl.

CPC ......... *C07D 209/86* (2013.01); *C07D 307/77* (2013.01); *C07D 307/91* (2013.01); *C07D 333/76* (2013.01); *C07D 401/10* (2013.01); *C07D 401/14* (2013.01); *C07D 403/10* (2013.01); *C07D 403/14* (2013.01); *C07D 471/10* (2013.01); *C07F 5/027* (2013.01); *C09K 11/06* (2013.01); *H10K 85/615* (2023.02); *H10K 85/622* (2023.02); *H10K 85/624* (2023.02); *H10K 85/626* (2023.02); *H10K 85/633* (2023.02); *H10K 85/636* (2023.02); *H10K 85/654* (2023.02); *H10K 85/6572* (2023.02); *H10K 85/6574* (2023.02); *H10K 85/658* (2023.02); *C07B 2200/05* (2013.01); *C07C 2603/24* (2017.05); *C07C 2603/97* (2017.05); *C09K 2211/1007* (2013.01); *C09K 2211/1011* (2013.01); *C09K 2211/1018* (2013.01); *H10K 50/11* (2023.02); *H10K 50/13* (2023.02); *H10K 50/18* (2023.02); *H10K 50/181* (2023.02); *H10K 50/19* (2023.02); *H10K 59/12* (2023.02); *H10K 85/6576* (2023.02); *H10K 2101/10* (2023.02)

(58) Field of Classification Search

CPC ............. H01L 51/0006; H01L 51/0061; H01L 51/0067; H01L 51/0072; H01L 51/0054; H01L 51/0056; C09K 11/06; C07C 15/28; C07C 211/61; C07D 307/91; C07D 307/77; C07D 209/86; C07D 333/76; C07D 403/10; C07D 401/10; C07D 471/10; C07D 251/24; C07F 5/027; H10K 85/658

See application file for complete search history.

(56) References Cited

U.S. PATENT DOCUMENTS

| | | | | |
|---|---|---|---|---|
| 2013/0153881 | A1* | 6/2013 | Tokoo .................... | H10K 50/11 257/40 |
| 2021/0036233 | A1* | 2/2021 | Joo ...................... | H10K 85/615 |
| 2021/0296589 | A1 | 9/2021 | Song et al. | |
| 2022/0173318 | A1 | 6/2022 | Kim et al. | |
| 2022/0285625 | A1 | 9/2022 | Tasaki et al. | |
| 2023/0047477 | A1 | 2/2023 | Tasaki et al. | |

FOREIGN PATENT DOCUMENTS

| | | | | |
|---|---|---|---|---|
| KR | 10-2191018 | B1 | 12/2020 | |
| WO | WO-2020080417 | A1 * | 4/2020 | ............. C09K 11/06 |
| WO | WO 2020/138872 | A1 | 7/2020 | |

OTHER PUBLICATIONS

China National Intellectual Property Administration, Office Action, Chinese Patent Application No. 202111298286.2, Feb. 21, 2025, seven pages.

* cited by examiner

ORGANIC LIGHT EMITTING DEVICE

CROSS-REFERENCE TO RELATED APPLICATIONS

The present application claims the benefit of Republic of Korea Patent Application No. 10-2020-0184955 filed in the Republic of Korea on Dec. 28, 2020, which is hereby incorporated by reference in its entirety.

FIELD OF TECHNOLOGY

The present disclosure relates to an organic light emitting device, and more specifically, to an organic light emitting diode (OLED) having enhanced emitting efficiency and lifespan and an organic light emitting device including the same.

BACKGROUND

As requests for a flat panel display device having a small occupied area have been increased, an organic light emitting display device including an OLED has been the subject of recent research and development.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. In addition, the organic light emitting display device can be operated at a voltage (e.g., 10V or below) lower than a voltage required to operate other display devices. Moreover, the organic light emitting display device has advantages in the power consumption and the color sense.

The OLED includes a first electrode as an anode over a substrate, a second electrode, which is spaced apart from and faces the first electrode, and an organic emitting layer therebetween.

For example, the organic light emitting display device may include a red pixel region, a green pixel region and a blue pixel region, and the OLED may be formed in each of the red, green and blue pixel regions.

However, the OLED in the blue pixel does not provide sufficient emitting efficiency and lifespan such that the organic light emitting display device has a limitation in the emitting efficiency and the lifespan.

SUMMARY

The present disclosure is directed to an OLED and an organic light emitting device including the OLED that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an aspect of the present disclosure is an organic light emitting device including a substrate, and an organic light emitting diode positioned on the substrate and including a first electrode, a second electrode facing the first electrode, a first emitting material layer including a first dopant of a boron derivative and a first host of an anthracene derivative and positioned between the first and second electrodes, a first electron blocking layer including an electron blocking material and positioned between the first electrode and the first emitting material layer, and a first hole blocking layer including a hole blocking material and positioned between the second electrode and the first emitting material layer, wherein the first dopant is represented by Formula 1: [Formula 1]

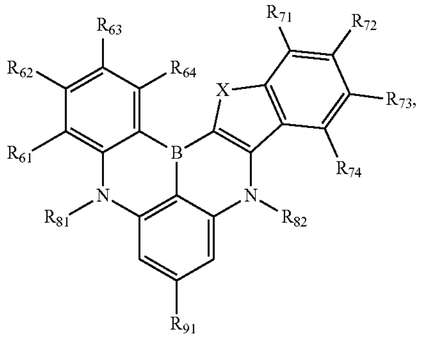

wherein X is one of $NR_1$, $CR_2R_3$, O, S, Se, $SiR_4R_5$, and each of $R_1$, $R_2$, $R_3$, $R_4$ and $R_5$ is independently selected from the group consisting of hydrogen, $C_1$ to $C_{10}$ alkyl group, $C_6$ to $C_{30}$ aryl group, $C_5$ to $C_{30}$ heteroaryl group, $C_3$ to $C_{30}$ cycloalkyl group and $C_3$ to $C_{30}$ alicyclic group, wherein each of $R_{61}$ to $R_{64}$ is independently selected from the group consisting of hydrogen, deuterium, $C_1$ to $C_{10}$ alkyl group unsubstituted or substituted with deuterium, $C_6$ to $C_{30}$ aryl group unsubstituted or substituted with at least one of deuterium and $C_1$ to $C_{10}$ alkyl, $C_6$ to $C_{30}$ arylamino group unsubstituted or substituted with at least one of deuterium and $C_1$ to $C_{10}$ alkyl, $C_5$ to $C_{30}$ heteroaryl group unsubstituted or substituted with at least one of deuterium and $C_1$ to $C_{10}$ alkyl and $C_3$ to $C_{30}$ alicyclic group unsubstituted or substituted with at least one of deuterium and $C_1$ to $C_{10}$ alkyl, or adjacent two of $R_{61}$ to $R_{64}$ are connected to each other to form a fused ring, wherein each of $R_{71}$ to $R_{74}$ is independently selected from the group consisting of hydrogen, deuterium, $C_1$ to $C_{10}$ alkyl group and $C_3$ to $C_{30}$ alicyclic group, wherein $R_{81}$ is selected from the group consisting of $C_6$ to $C_{30}$ aryl group unsubstituted or substituted with at least one of deuterium and $C_1$ to $C_{10}$ alkyl, $C_5$ to $C_{30}$ heteroaryl group unsubstituted or substituted with at least one of deuterium and $C_1$ to $C_{10}$ alkyl and $C_3$ to $C_{30}$ alicyclic group unsubstituted or substituted with at least one of deuterium and $C_1$ to $C_{10}$ alkyl, or is connected with $R_{61}$ to form a fused ring, wherein $R_{82}$ is selected from the group consisting of $C_6$ to $C_{30}$ aryl group unsubstituted or substituted with at least one of deuterium and $C_1$ to $C_{10}$ alkyl, $C_5$ to $C_{30}$ heteroaryl group unsubstituted or substituted with at least one of deuterium and $C_1$ to $C_{10}$ alkyl and $C_3$ to $C_{30}$ alicyclic group unsubstituted or substituted with at least one of deuterium and $C_1$ to $C_{10}$ alkyl, wherein $R_{91}$ is selected from the group consisting of hydrogen, $C_1$ to $C_{10}$ alkyl group, $C_3$ to $C_{15}$ cycloalkyl group unsubstituted or substituted with $C_1$ to $C_{10}$ alkyl, $C_6$ to $C_{30}$ aryl group unsubstituted or substituted with $C_1$ to $C_{10}$ alkyl, $C_5$ to $C_{30}$ heteroaryl group unsubstituted or substituted with $C_1$ to $C_{10}$ alkyl, $C_6$ to $C_{30}$ arylamino group unsubstituted or substituted with $C_1$ to $C_{10}$ alkyl and $C_3$ to $C_{30}$ alicyclic group unsubstituted or substituted with $C_1$ to $C_{10}$ alkyl, wherein when each of $R_{81}$, $R_{82}$ and $R_{91}$ is $C_6$ to $C_{30}$ aryl group substituted with $C_1$ to $C_{10}$ alkyl, these alkyl groups are connected to each other to form a fused ring, wherein the first host is represented by Formula 2:

[Formula 2]

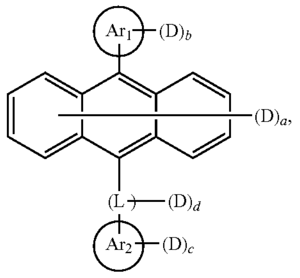

wherein each of Ar1 and Ar2 is independently $C_6$ to $C_{30}$ aryl group or $C_5$ to $C_{30}$ heteroaryl group, and L is a single bond or $C_6$ to $C_{30}$ arylene group, wherein a is an integer of 0 to 8, each of b, c and d is independently an integer of 0 to 30, wherein at least one of a, b, c and d is a positive integer, wherein the electron blocking material is represented by Formula 3:

[Formula 3]

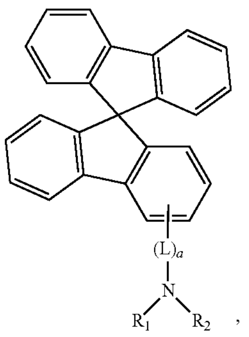

wherein in Formula 3, L is arylene group, and a is 0 or 1, and wherein each of $R_1$ and $R_2$ is independently selected from the group consisting of unsubstituted or substituted $C_6$ to $C_{30}$ aryl group and unsubstituted or substituted $C_5$ to $C_{30}$ heteroaryl group.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION

Reference will now be made in detail to some of the examples and preferred embodiments, which are illustrated in the accompanying drawings.

Figure 1:
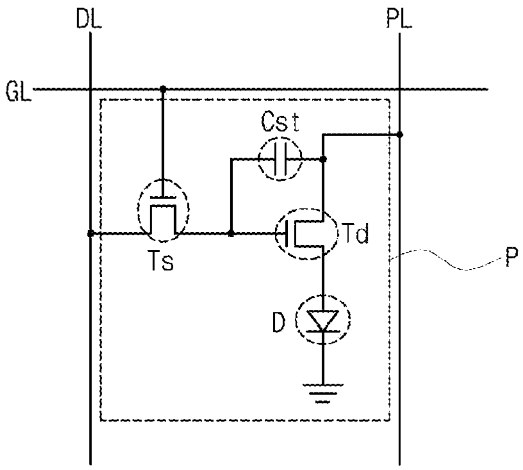
FIG. 1 is a schematic circuit diagram illustrating an organic light emitting display device of the present disclosure.

FIG. 1 is a schematic circuit diagram illustrating an organic light emitting display device of the present disclosure.

As illustrated in FIG. 1, a gate line GL and a data line DL, which cross each other to define a pixel (pixel region) P, and a power line PL are formed in an organic light emitting display device. A switching thin film transistor (TFT) Ts, a driving TFT Td, a storage capacitor Cst and an OLED D are formed in the pixel P. The pixel P may include a red pixel, a green pixel and a blue pixel.

The switching thin film transistor Ts is connected to the gate line GL and the data line DL, and the driving thin film transistor Td and the storage capacitor Cst are connected between the switching thin film transistor Ts and the power line PL. The OLED D is connected to the driving thin film transistor Td. When the switching thin film transistor Ts is turned on by the gate signal applied through the gate line GL, the data signal applied through the data line DL is applied to a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the OLED D through the driving thin film transistor Td. The OLED D emits light having a luminance proportional to the current flowing through the driving thin film transistor Td. In this case, the storage capacitor Cst is charged with a voltage proportional to the data signal so that the voltage of the gate electrode in the driving thin film transistor Td is kept constant during one frame. Therefore, the organic light emitting display device can display a desired image.

Figure 2:
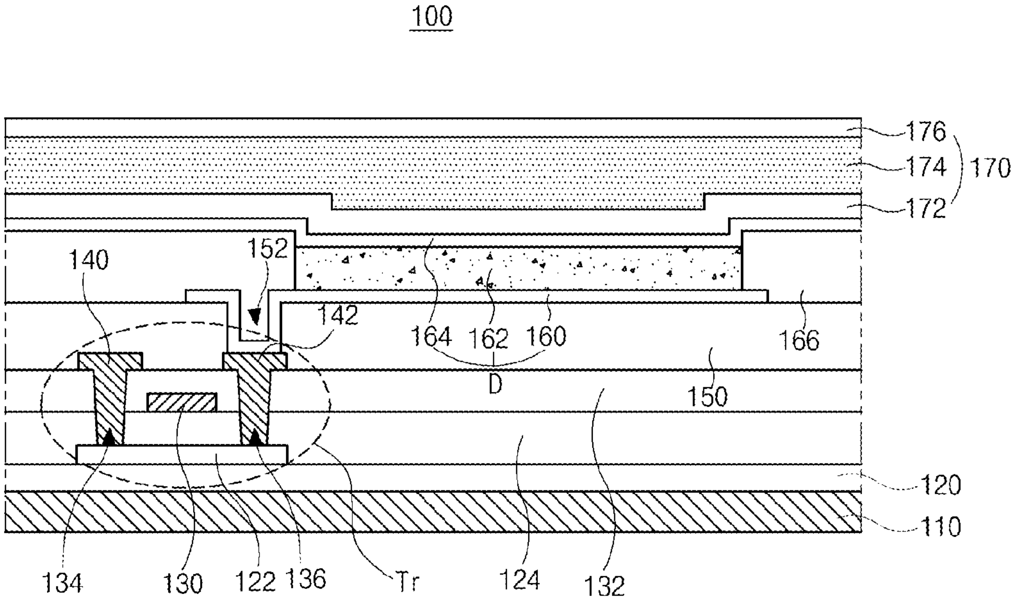
FIG. 2 is a schematic cross-sectional view illustrating an organic light emitting display device according to a first embodiment of the present disclosure.

FIG. 2 is a schematic cross-sectional view illustrating an organic light emitting display device according to a first embodiment of the present disclosure.

As illustrated in FIG. 2, the organic light emitting display device 100 includes a substrate 110, a TFT Tr and an OLED D connected to the TFT Tr. For example, the organic light emitting display device 100 may include a red pixel, a green pixel, and a blue pixel, and the OLED D may be formed in each of the red, green, and blue pixels. Namely, the OLEDs D emitting red light, green light and blue light may be provided in the red, green and blue pixels, respectively.

The substrate 110 may be a glass substrate or a flexible substrate. For example, the flexible substrate may be one of a polyimide (PI) substrate, polyethersulfone (PES), polyethylenenaphthalate (PEN), polyethylene terephthalate (PET) and polycarbonate (PC).

A buffer layer 120 is formed on the substrate, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 are formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element. Namely, the TFT Tr may correspond to the driving TFT Td (of FIG. 1).

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer (or a planarization layer) 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel and on the passivation layer 150. The first electrode 160 may be an anode and may be formed of a conductive material, e.g., a transparent conductive oxide (TCO), having a relatively high work function. For example, the first electrode 160 may be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 100 is operated in a bottom-emission type, the first electrode 160 may have a single-layered structure of the transparent conductive oxide. When the organic light emitting display device 100 is operated in a top-emission type, a reflection electrode or a reflection layer may be formed under the first electrode 160. For example, the reflection electrode or the reflection layer may be formed of silver (Ag) or aluminum-palladium-copper (APC) alloy. In this instance, the first electrode 160 may have a triple-layered structure of ITO/Ag/ITO or ITO/APC/ITO.

A bank layer 166 is formed on the planarization layer 150 to cover an edge of the first electrode 160. Namely, the bank layer 166 is positioned at a boundary of the pixel and exposes a center of the first electrode 160 in the pixel.

An organic emitting layer 162 is formed on the first electrode 160. The organic emitting layer 162 may include an emitting material layer (EML) including an emitting material, an electron blocking layer (EBL) between the first electrode 160 and the EML and a hole blocking layer (HBL) between the EML and the second electrode 164.

The organic emitting layer 162 is separated in each of the red, green and blue pixels. As illustrated below, the organic emitting layer 162 in the blue pixel includes a host of an anthracene derivative (an anthracene compound), at least a part of hydrogens of which is substituted with deuterium (deuterated), and a dopant of a boron derivative (a boron compound) such that the emitting efficiency and the lifespan of the OLED D in the blue pixel are improved.

In addition, in the OLED D, the EBL includes an amine derivative substituted by spirofluorene (e.g., "spirofluorene-substituted amine derivative"), and the HBL includes at least one of a hole blocking material of an azine derivative and a hole blocking material of a benzimidazole derivative. As a result, the lifespan of the OLED D and the organic light emitting display device 100 is further improved.

The second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg), silver (Ag) or their alloy, e.g., Al—Mg alloy (AlMg) or Ag—Mg alloy (MgAg). In the top-emission type organic light emitting display device 100, the second electrode 164 may have a thin profile (small thickness) to provide a light transmittance property (or a semi-transmittance property).

The first electrode 160, the organic emitting layer 162, and the second electrode 164 constitute the OLED D.

An encapsulation film 170 is formed on the second electrode 164 to prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 may be omitted.

The organic light emitting display device 100 may further include a polarization plate (not shown) for reducing an ambient light reflection. For example, the polarization plate may be a circular polarization plate. In the bottom-emission type organic light emitting display device 100, the polarization plate may be disposed under the substrate 110. In the top-emission type organic light emitting display device 100, the polarization plate may be disposed on or over the encapsulation film 170.

In addition, in the top-emission type organic light emitting display device 100, a cover window (not shown) may be attached to the encapsulation film 170 or the polarization plate. In this instance, the substrate 110 and the cover window have a flexible property such that a flexible organic light emitting display device may be provided.

Figure 3:
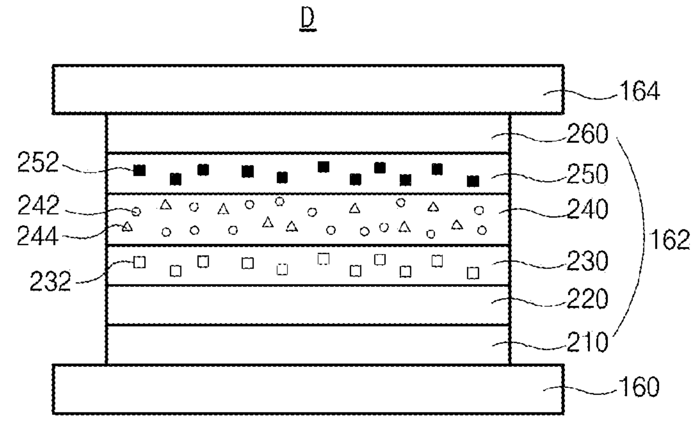
FIG. 3 is a schematic cross-sectional view illustrating an OLED having a single emitting part for the organic light emitting display device according to the first embodiment of the present disclosure.

FIG. 3 is a schematic cross-sectional view illustrating an OLED having a single emitting part for the organic light emitting display device according to the first embodiment of the present disclosure.

As illustrated in FIG. 3, the OLED D includes the first electrode 160 and the second electrode 164, which face each other, and the organic emitting layer 162 therebetween. The organic emitting layer 162 includes an EML 240 between the first and second electrodes 160 and 164, an EBL 230 between the first electrode 160 and the EML 240 and an HBL between the EML 240 and the second electrode 164. The organic light emitting display device 100 (of FIG. 2) includes red, green and blue pixels, and the OLED D may be positioned in the blue pixel.

One of the first and second electrodes 160 and 164 is an anode, and the other one of the first and second electrodes 160 and 164 is a cathode. One of the first and second electrodes 160 and 164 is a transparent electrode (or a semi-transparent electrode) electrode, and the other one of the first and second electrodes 160 and 164 is a reflection electrode.

The organic emitting layer 162 may further include a hole transporting layer (HTL) 220 between the first electrode 160 and the EBL 230.

In addition, the organic emitting layer 162 may further include a hole injection layer (HIL) 210 between the first electrode 160 and the HTL 220 and an electron injection layer (EIL) 260 between the second electrode 164 and the HBL 250.

For example, the HIL 210 may include at least one compound selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPB or NPD), 1,4,5,8,9,11-hexaazatriphenylenehexacarbonitrile(dipyrazino[2,3-f:2' 3'-h]quinoxaline-2,3,6,7,10,11-hexacarbonitrile (HAT-CN), 1,3,5-tris[4-(diphenylamino)phenyl]benzene (TDAPB), poly(3,4-ethylenedioxythiphene) polystyrene sulfonate (PEDOT/PSS) and N-(biphenyl-4-yl)-9,9-dimethyl-N-(4-(9-phenyl-9H-carbazol-3-yl)phenyl)-9H-fluoren-2-amine. Alternatively, the HIL 210 may include a compound in Formula 12 as a host and a compound in Formula 13 as a dopant.

The HTL220 may include at least one compound selected from the group consisting of N,N'-diphenyl-N,N'-bis(3-methylphenyl)-1,1'-biphenyl-4,4'-diamine (TPD), NPB (or NPD), 4,4'-bis(N-carbazolyl)-1,1'-biphenyl (CBP), poly[N,N'-bis(4-butylpnehyl)-N,N'-bis(phenyl)-benzidine] (poly-TPD), (poly [(9,9-dioctylfluorenyl-2,7-diyl)-co-(4,4'-(N-(4-sec-butylphenyl)diphenylamine))] (TFB), di-[4-(N,N-di-p-tolyl-amino)-phenyl]cyclohexane (TAPC), 3,5-di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl) biphenyl-4-amine. Alternatively, the HTL 220 may include the compound in Formula 12.

The EIL 260 may include at least one of an alkali metal, such as Li, an alkali halide compound, such as LiF, CsF, NaF, or $BaF_2$, and an organo-metallic compound, such as Liq, lithium benzoate, or sodium stearate, but it is not limited thereto. Alternatively, the EIL 260 may include a compound in Formula 14 as a host and an alkali metal as a dopant.

The EML 240 includes the dopant 242 of a boron derivative and the host 244 of a deuterated anthracene derivative and provides blue emission. Namely, at least one hydrogen in an anthracene derivative is substituted with deuterium, and it may be referred to as a deuterated anthracene derivative. The boron derivative is not substituted with deuterium, or a part of hydrogens of a boron derivative is substituted with deuterium. It may be referred to as a non-deuterated boron derivative or a partially-deuterated boron derivative.

In the EML 240, the host 244 is partially or wholly deuterated, and the dopant 242 is non-deuterated or partially deuterated.

The boron derivative as the dopant 242 may be represented by Formula 1-1 or 1-2.

[Formula 1-1]

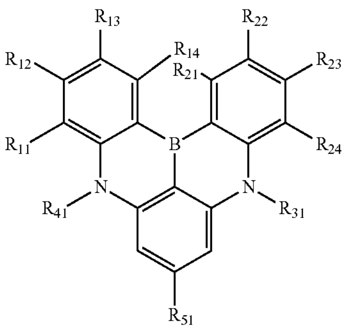

[Formula 1-2]

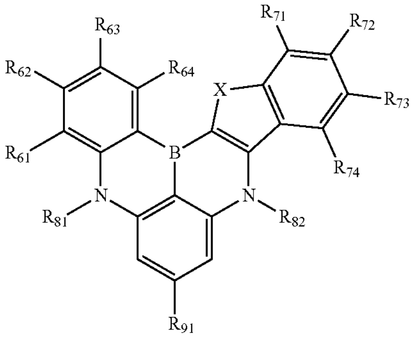

In Formula 1-1, each of $R_{11}$ to $R_{14}$ and each of $R_{21}$ to $R_{24}$ is selected from the group consisting of hydrogen, $C_1$ to $C_{10}$ alkyl group, $C_6$ to $C_{30}$ aryl group unsubstituted or substituted with $C_1$ to $C_{10}$ alkyl, $C_6$ to $C_{30}$ arylamino group unsubstituted or substituted with $C_1$ to $C_{10}$ alkyl, $C_5$ to $C_{30}$ heteroaryl group unsubstituted or substituted with $C_1$ to $C_{10}$ alkyl and $C_3$ to $C_{30}$ alicyclic group unsubstituted or substituted with $C_1$ to $C_{10}$ alkyl, or adjacent two of $R_{11}$ to $R_{14}$ and $R_{21}$ to $R_{24}$ are connected (combined, linked or joined) to each other to form a fused ring. Each of $R_{31}$ and $R_{41}$ is independently selected from the group consisting of hydrogen, $C_1$ to $C_{10}$ alkyl group, $C_6$ to $C_{30}$ aryl group unsubstituted or substituted with $C_1$ to $C_{10}$ alkyl, $C_6$ to $C_{30}$ arylamino group unsubstituted or substituted with $C_1$ to $C_{10}$ alkyl, $C_5$ to $C_{30}$ heteroaryl group unsubstituted or substituted with $C_1$ to $C_{10}$ alkyl and $C_3$ to $C_{30}$ alicyclic group unsubstituted or substituted with $C_1$ to $C_{10}$ alkyl. $R_{51}$ is selected from the group consisting of hydrogen, $C_1$ to $C_{10}$ alkyl group, $C_3$ to $C_{15}$ cycloalkyl group unsubstituted or substituted with $C_1$ to $C_{10}$ alkyl, $C_6$ to $C_{30}$ aryl group unsubstituted or substituted with $C_1$ to $C_{10}$ alkyl, $C_5$ to $C_{30}$ heteroaryl group unsubstituted or substituted with $C_1$ to $C_{10}$ alkyl, $C_6$ to $C_{30}$ arylamino group unsubstituted or substituted with $C_1$ to $C_{10}$ alkyl, $C_3$ to $C_{30}$ alicyclic group unsubstituted or substituted with $C_1$ to $C_{10}$ alkyl and $C_5$ to $C_{30}$ hetero-ring group (e.g., heteroalicyclic group) unsubstituted or substituted with $C_1$ to $C_{10}$ alkyl.

When each of $R_{31}$, $R_{41}$ and $R_{51}$ is $C_6$ to $C_{30}$ aryl group substituted with $C_1$ to $C_{10}$ alkyl, alkyl group may be connected to each other to form a fused ring.

For example, in Formula 1-1, each of $R_{11}$ to $R_{14}$, each of $R_{21}$ to $R_{24}$ and each of $R_{31}$ and $R_{41}$ may be independently selected from the group consisting of hydrogen, $C_1$ to $C_{10}$alkyl group, $C_6$ to $C_{30}$ aryl group unsubstituted or substituted with $C_1$ to $C_{10}$ alkyl and $C_5$ to $C_{30}$ heteroaryl group unsubstituted or substituted with $C_1$ to $C_{10}$ alkyl, and $R_{51}$ may be selected from the group consisting of $C_1$ to $C_{10}$ alkyl group, $C_5$ to $C_{30}$ heteroaryl group unsubstituted or substituted with $C_1$ to $C_{10}$ alkyl, $C_6$ to $C_{30}$ arylamino group unsubstituted or substituted with $C_1$ to $C_{10}$ alkyl and $C_5$ to $C_{30}$ hetero-ring group unsubstituted or substituted with $C_1$ to $C_{10}$ alkyl.

In an exemplary embodiment, in Formula 1-1, one of $R_{11}$ to $R_{14}$ and one of $R_{21}$ to $R_{24}$ may be $C_1$ to $C_{10}$ alkyl group, and the rest of $R_1$ to $R_{14}$ and the rest of $R_{21}$ to $R_{24}$ may be hydrogen. Each of $R_{31}$ and $R_{41}$ may be phenyl substituted with $C_1$ to $C_{10}$ alkyl or dibenzofuranyl substituted with $C_1$ to $C_{10}$ alkyl. $R_{51}$ may be alkyl group, diphenylamino group, heteroaryl group containing nitrogen, or hetero-ring group containing nitrogen. In this instance, $C_1$ to $C_{10}$ alkyl group may be tert-butyl.

Without other description, the fused ring may be C3 to C10 alicyclic ring.

In Formula 1-2, X is one of $NR_1$, $CR_2R_3$, O, S, Se, $SiR_4R_5$, and each of $R_1$, $R_2$, $R_3$, $R_4$ and $R_5$ is independently selected from the group consisting of hydrogen, $C_1$ to $C_{10}$ alkyl group, $C_6$ to $C_{30}$ aryl group, $C_5$ to $C_{30}$ heteroaryl group, $C_3$ to $C_{30}$ cycloalkyl group and $C_3$ to $C_{30}$ alicyclic group. Each of $R_{61}$ to $R_{64}$ is independently selected from the group consisting of hydrogen, deuterium, $C_1$ to $C_{10}$ alkyl group unsubstituted or substituted with deuterium, $C_6$ to $C_{30}$ aryl group unsubstituted or substituted with at least one of deuterium and $C_1$ to $C_{10}$ alkyl, $C_6$ to $C_{30}$ arylamino group unsubstituted or substituted with at least one of deuterium and $C_1$ to $C_{10}$ alkyl, $C_5$ to $C_{30}$ heteroaryl group unsubstituted or substituted with at least one of deuterium and $C_1$ to $C_{10}$ alkyl and $C_3$ to $C_{30}$ alicyclic group unsubstituted or substituted with at least one of deuterium and $C_1$ to $C_{10}$ alkyl, or adjacent two of $R_{61}$ to $R_{64}$ are connected to each other to form a fused ring. Each of $R_{71}$ to $R_{74}$ is independently selected from the group consisting of hydrogen, deuterium, $C_1$ to $C_{10}$ alkyl group and $C_3$ to $C_{30}$ alicyclic group. $R_{81}$ is selected from the group consisting of $C_6$ to $C_{30}$ aryl group unsubstituted or substituted with at least one of deuterium and $C_1$ to $C_{10}$ alkyl, $C_5$ to $C_{30}$ heteroaryl group unsubstituted or substituted with at least one of deuterium and $C_1$ to $C_{10}$ alkyl and $C_3$ to $C_{30}$ alicyclic group unsubstituted or substituted with at least one of deuterium and $C_1$ to $C_{10}$ alkyl, or is connected with $R_{61}$ to form a fused ring. $R_{82}$ is selected from the group consisting of $C_6$ to $C_{30}$ aryl group unsubstituted or substituted with at least one of deuterium and $C_1$ to $C_{10}$ alkyl, $C_5$ to $C_{30}$ heteroaryl group unsubstituted or substituted with at least one of deuterium and $C_1$ to $C_{10}$ alkyl and $C_3$ to $C_{30}$ alicyclic group unsubstituted or substituted with at least one of deuterium and $C_1$ to $C_{10}$ alkyl, and $R_{91}$ is selected from the group consisting of hydrogen, $C_1$ to $C_{10}$ alkyl group, $C_3$ to $C_{15}$ cycloalkyl group unsubstituted or substituted with $C_1$ to $C_{10}$ alkyl, $C_6$ to $C_{30}$ aryl group unsubstituted or substituted with $C_1$ to $C_{10}$ alkyl, $C_5$ to $C_{30}$ heteroaryl group unsubstituted or substituted with $C_1$ to $C_{10}$ alkyl, $C_6$ to $C_{30}$ arylamino group unsubstituted or substituted with $C_1$ to $C_{10}$ alkyl and $C_3$ to $C_{30}$ alicyclic group unsubstituted or substituted with $C_1$ to $C_{10}$ alkyl.

When each of $R_{81}$, $R_{82}$ and $R_{91}$ is $C_6$ to $C_{30}$ aryl group substituted with $C_1$ to $C_{10}$alkyl, alkyl group may be connected to each other to form a fused ring.

For example, in Formula 1-2, X may be O or S. Each of $R_{61}$ to $R_{64}$ may be independently selected from the group consisting of hydrogen, deuterium, $C_1$ to $C_{10}$ alkyl group and $C_6$ to $C_{30}$ arylamino group unsubstituted or substituted with deuterium, or adjacent two of $R_{61}$ to $R_{64}$ may be connected to form a fused ring. Each of $R_{71}$ to $R_{74}$ may be independently selected from the group consisting of hydrogen, deuterium and $C_1$ to $C_{10}$ alkyl. $R_{81}$ may be selected from the group consisting of $C_6$ to $C_{30}$ aryl group unsubstituted or substituted with at least one of deuterium and $C_1$ to $C_{10}$ alkyl and $C_5$ to $C_{30}$ heteroaryl group unsubstituted or substituted with at least one of deuterium and $C_1$ to $C_{10}$ alkyl, or may be connected with $R_{61}$ to form a fused ring. $R_{82}$ may be selected from the group consisting of $C_6$ to $C_{30}$ aryl group unsubstituted or substituted with at least one of deuterium and $C_1$ to $C_{10}$ alkyl and $C_5$ to $C_{30}$ heteroaryl group unsubstituted or substituted with at least one of deuterium and $C_1$ to $C_{10}$ alkyl, and $R_{91}$ may be selected from the group consisting of $C_1$ to $C_{10}$ alkyl group.

In an exemplary embodiment, in Formula 1-2, X may be O. Each of $R_{61}$ to $R_{64}$ may be independently selected from the group consisting of hydrogen, deuterium and diphenylamino, or adjacent two of $R_{61}$ to $R_{64}$ may be connected to form a fused ring. In this instance, diphenylamino and the fused ring may be deuterated. Each of $R_{71}$ to $R_{74}$ may be independently selected from the group consisting of hydrogen, deuterium and $C_1$ to $C_{10}$ alkyl. Each of $R_{81}$ and $R_{82}$ may be independently selected from the group consisting of phenyl unsubstituted or substituted with at least one of deuterium and $C_1$ to $C_{10}$ alkyl and dibenzofuranyl unsubstituted or substituted with at least one of deuterium and $C_1$ to $C_{10}$ alkyl. $R_{91}$ may be $C_1$ to $C_{10}$ alkyl group. In this instance, $C_1$ to $C_{10}$ alkyl group may be tert-butyl.

In further exemplary embodiment, in Formula 1-2, $R_{73}$ may be $C_1$ to $C_{10}$ alkyl group, and each of $R_{71}$, $R_{72}$ and $R_{74}$ may be independently hydrogen or deuterium.

In the boron derivative in Formula 1-2, other aromatic ring and hetero-aromatic ring except a benzene ring, which is combined to boron atom and two nitrogen atoms, may be deuterated. Namely, in Formula 1-2, $R_{91}$ may be not deuterium.

The deuterated anthracene derivative as the host 244 may be represented by Formula 2:

[Formula 2]

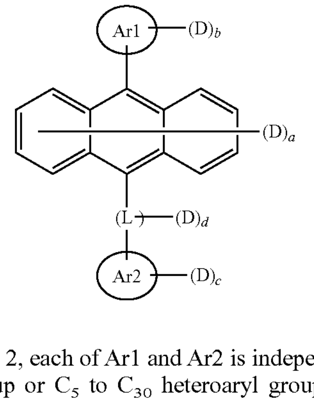

In Formula 2, each of Ar1 and Ar2 is independently $C_6$ to $C_{30}$ aryl group or $C_5$ to $C_{30}$ heteroaryl group, and L is a single bond or $C_6$ to $C_{30}$ arylene group. In addition, a is an integer of 0 to 8, each of b, c and d is independently an integer of 0 to 30, and at least one of a, b, c and d is a positive integer. (D denotes a deuterium atom, and each of a, b, c and d denotes a number of deuterium atoms.)

Ar1 and Ar2 may be same or different.

In Formula 2, Ar1 and Ar2 may be selected from the group consisting of phenyl, naphthyl, dibenzofuranyl, phenyl-dibenzofuranyl and a fused dibenzofuranyl, and L may be the single bond or phenylene.

For example, Ar1 may be selected from the group consisting of naphthyl, dibenzofuranyl, phenyl-dibenzofuranyl and a fused dibenzofuranyl, Ar2 may be selected from the group consisting of phenyl and naphthyl, and L may be the single bond or phenylene.

In an exemplary embodiment, in the deuterated anthracene derivative in Formula 2, 1-naphthanlene moiety may be directly connected to anthracene moiety, and 2-naphthalene moiety may be connected to anthracene moiety directly or through a phenylene linker. At least one hydrogen, preferably all hydrogen, of the anthracene derivative is substituted with deuterium.

For example, the boron derivative in Formula 1-1 or 1-2 as the dopant 242 may be one of the compounds in Formula 3.

[Formula 3]

1-1

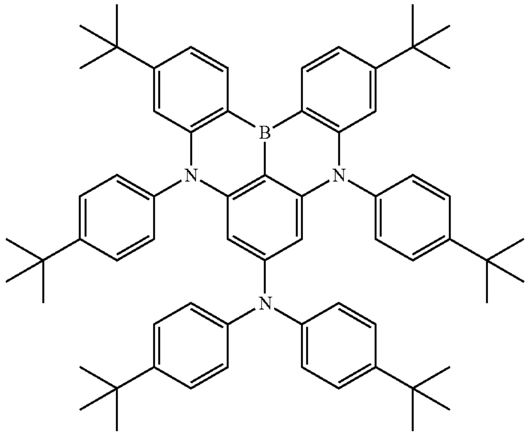

1-2

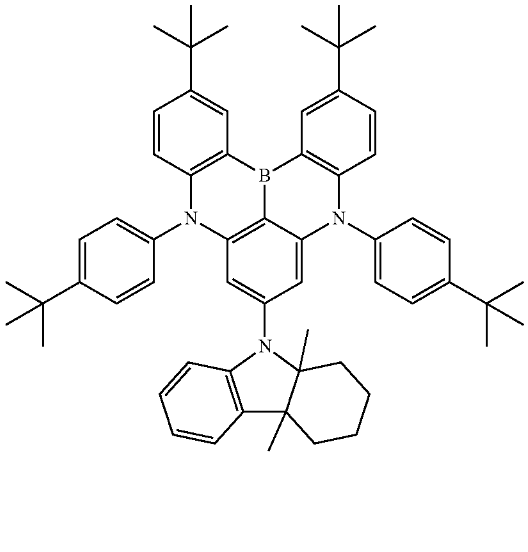

-continued
1-3
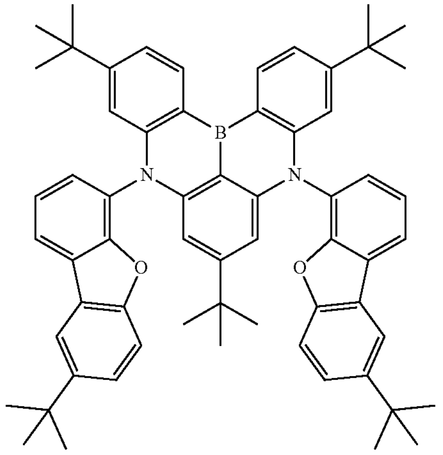
1-4
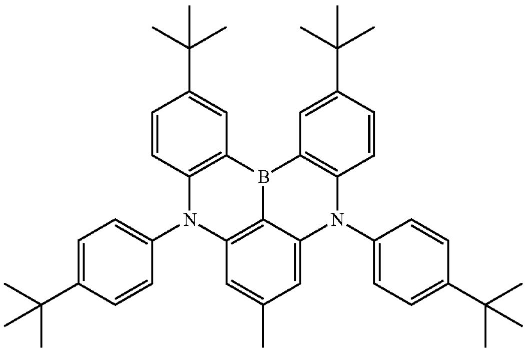
1-5
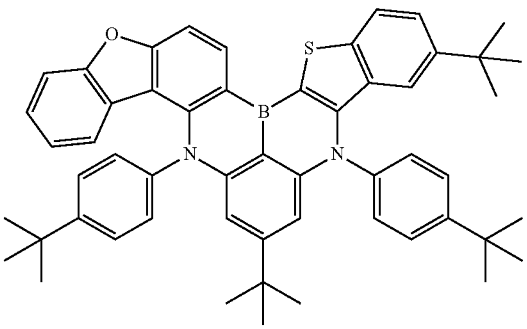
1-6
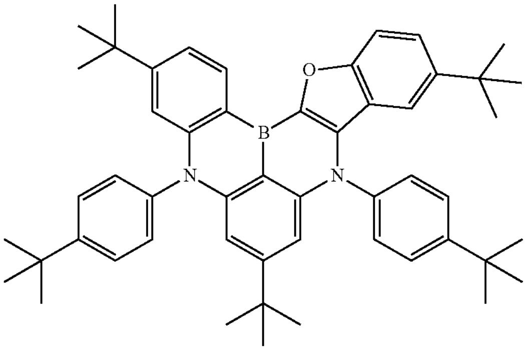
-continued
1-7
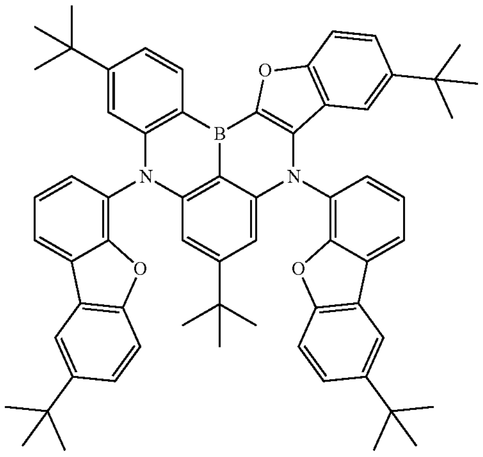
1-8
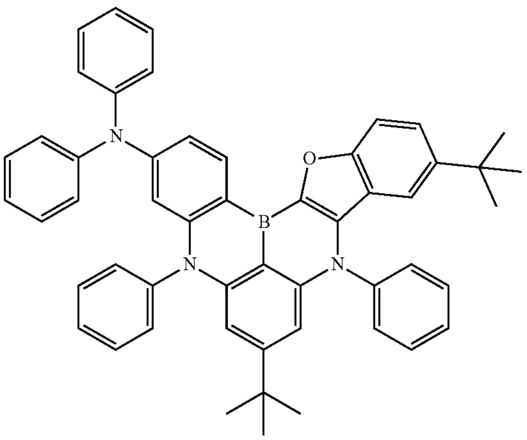
1-9
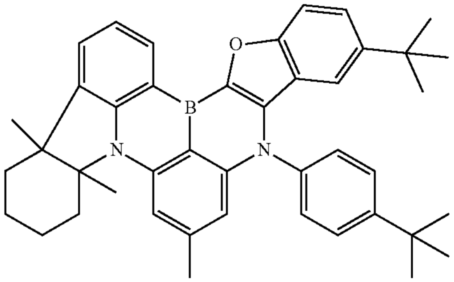
1-10
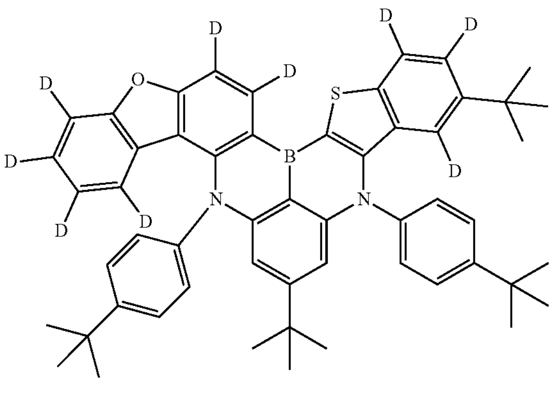

-continued
1-11
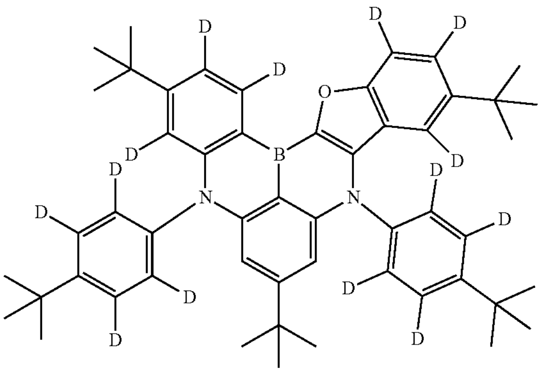
1-12
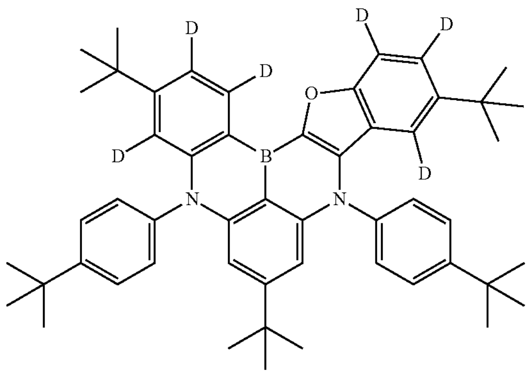
1-13
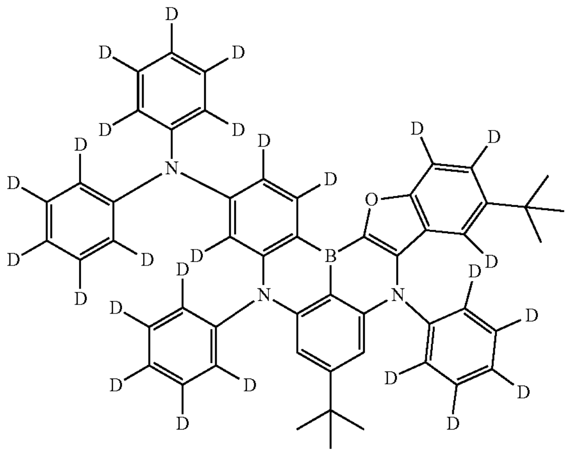
-continued
1-14
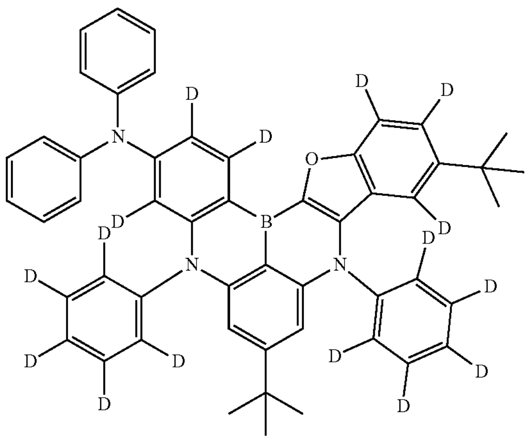
1-15
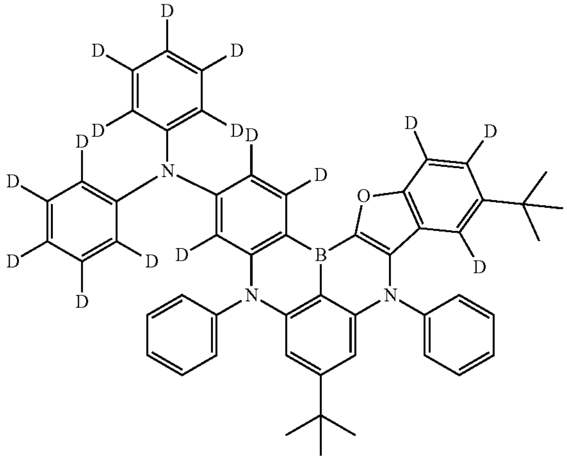
1-16
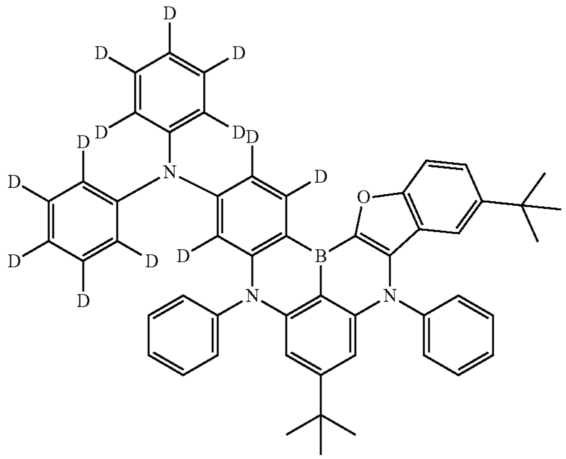

-continued 1-17

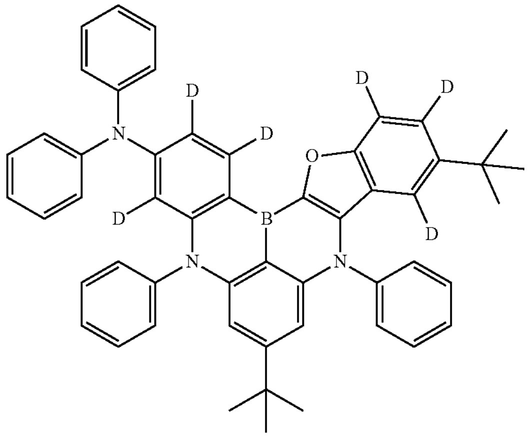

For example, the anthracene derivative in Formula 2 as the host 244 may be one of the compounds in Formula 4.

[Formula 4]

2-7

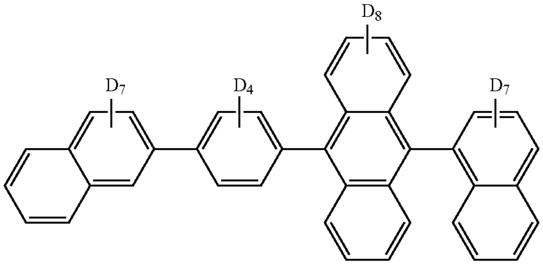

2-8

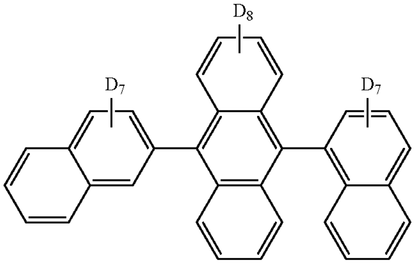

2-9

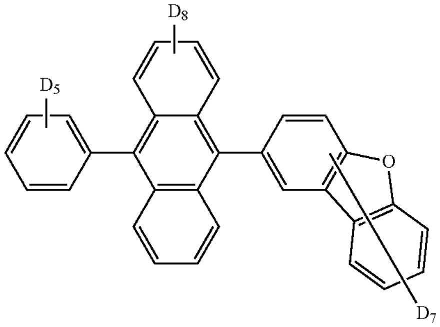

-continued 2-10

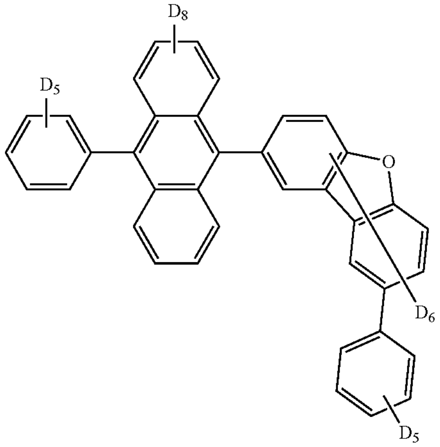

2-11

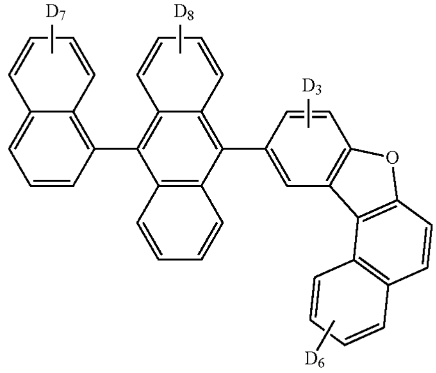

2-12

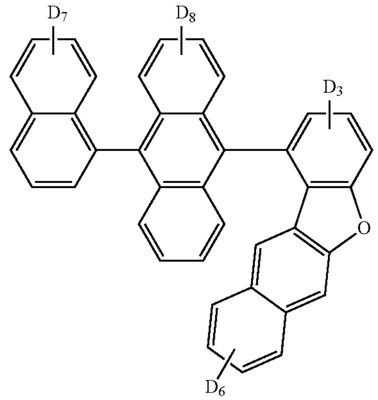

In the EML 240, the dopant 242 may have a weight % of about 0.1 to 10, preferably 1 to 5, but it is not limited thereto. The EML 240 may have a thickness of about 100 to 500 Å, preferably 100 to 300 Å, but it is not limited thereto.

In the OLED D of the present disclosure, since the EML 240 includes the dopant 242 being the boron derivative and the host 244 being the deuterated anthracene derivative, the emitting efficiency and the lifespan of the OLED D and the organic light emitting display device 100 are improved.

In addition, when the EML 240 includes the boron derivative as the dopant 242 having an asymmetric structure as Formula 1-2, the emitting efficiency and the lifespan of the OLED D and the organic light emitting display device 100 are further improved.

Moreover, when the EML 240 includes the boron derivative as the dopant 242, in which other aromatic ring and hetero-aromatic ring except a benzene ring being combined to boron atom and two nitrogen atoms are partially or wholly deuterated, the emitting efficiency and the lifespan of the OLED D and the organic light emitting display device 100 are further improved.

Furthermore, when the anthracene derivative as the host 244 includes two naphthalene moieties connected to the anthracene moiety and is partially or wholly deuterated, the emitting efficiency and the lifespan of the OLED D and the organic light emitting display device 100 including the anthracene derivative are further improved.

Synthesis of the Dopant

1. Synthesis of the Compound 1-1

(1) The Compound I1-1c

[Reaction Formula 1-1]

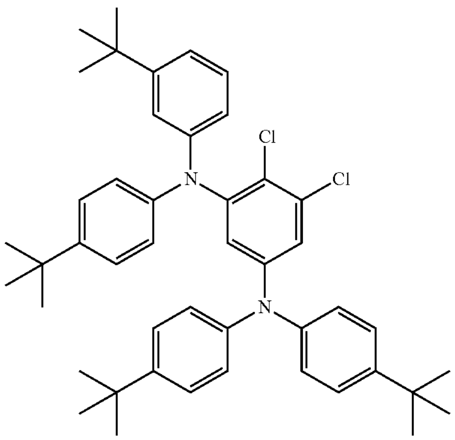

I1-1a

+

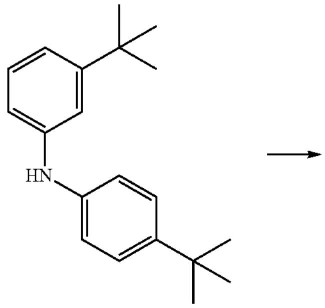

I1-1b

-continued

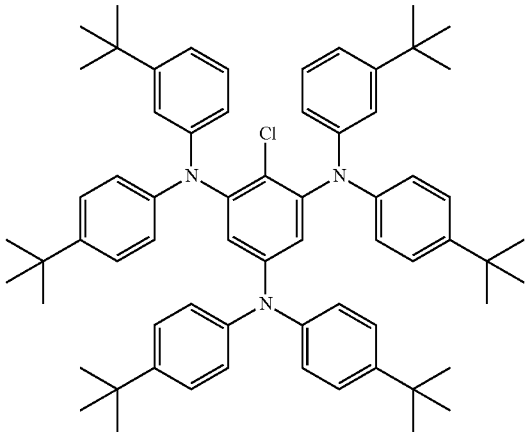

I1-1c

The compound I1-1a (69.2 g, 98 mmol), the compound I1-1b (27.6 g, 98 mmol), palladium acetate (0.45 g, 2 mmol), sodium tert-butoxide (18.9 g, 196 mmol), tri-tert-butylphosphine (0.8 g, 4 mmol), and toluene (300 mL) were added into 500 mL flask and were refluxed and stirred for 5 hours. After completion of reaction, the mixture was filtered, and residual solution was concentrated. The mixture was separated by a column chromatography to obtain the compound I1-1c (58.1 g). (yield 84%).

(2) The Compound 1-1

[Reaction Formula 1-2]

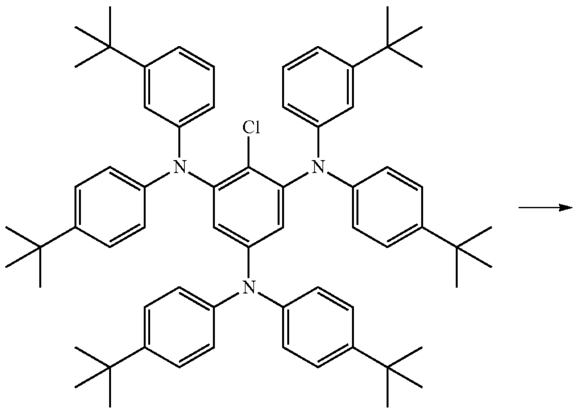

I1-1c

-continued

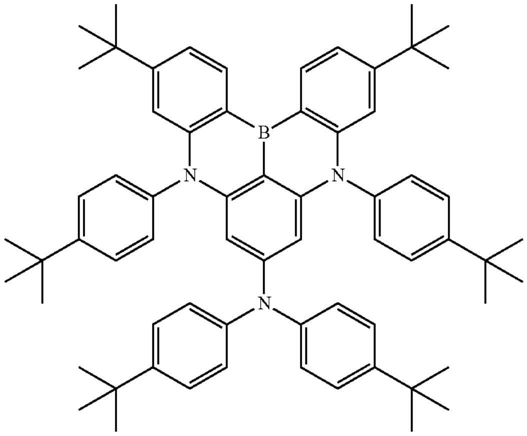

1-1

The compound I1-1c (11.9 g, 12.5 mmol) and tert-butylbenzene (60 ml) were added into 500 mL flask. In the temperature of −78° C., n-butyl-lithium in heptane (45 mL, 37.5 mmol) was dropwisely added into the mixture, and the mixture was stirred under the temperature of 60° C. for 3 hours. Heptane was removed by blowing nitrogen at 60° C. Boron tribromide (6.3 g, 25 mmol) was dropwisely added at −78° C. The mixture was stirred at room temperature for 1 hour, and N,N-diisopropylethylamine (3.2 g, 25 mmol) was dropwisely added at 0° C. The mixture was stirred at 120° C. for 2 hours. After completion of the reaction, an aqueous sodium acetate solution was added and stirred at room temperature. After extraction with ethyl acetate, the organic layer was concentrated. The mixture was separated by column chromatography to obtain the compound 1-1 (2.3 g). (yield 20%)

2. Synthesis of the Compound 1-4

(1) The Compound I1-4c

[Reaction Formula 2-1]

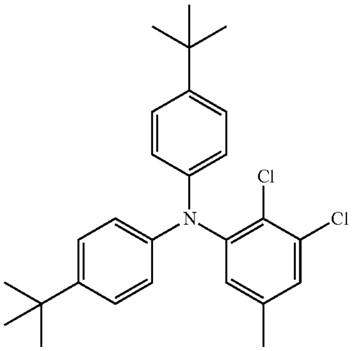

I1-4a

+

-continued

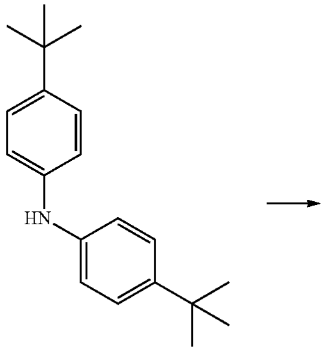

I1-4b

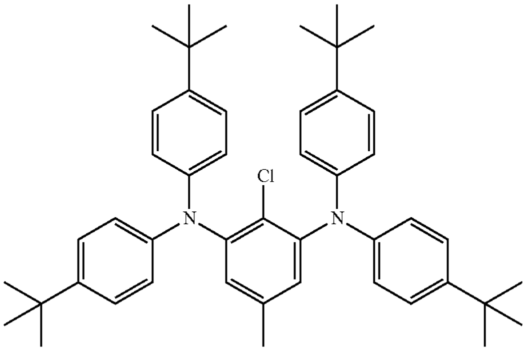

I1-4c

The compound I1-4a (43.1 g, 98 mmol), the compound I1-4b (27.6 g, 98 mmol), palladium acetate (0.45 g, 2 mmol), sodium tert-butoxide (18.9 g, 196 mmol), tri-tert-butylphosphine (0.8 g, 4 mmol), and toluene (300 mL) were added into 500 mL flask and were refluxed and stirred for 5 hours. After completion of reaction, the mixture was filtered, and residual solution was concentrated. The mixture was separated by a column chromatography to obtain the compound I1-4c (57.1 g). (yield 85%).

(2) The Compound 1-4

[Reaction Formula 2-2]

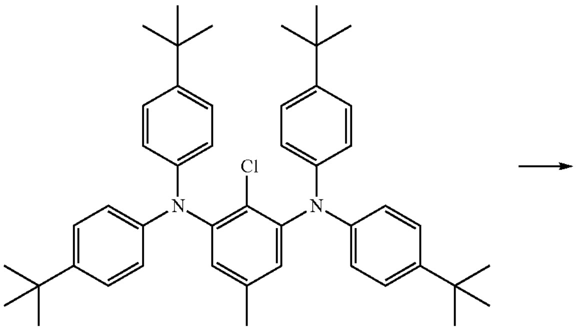

I1-4c

-continued

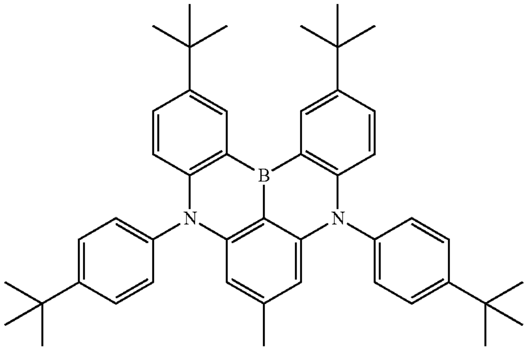

1-4

The compound I1-4c (8.6 g, 12.5 mmol) and tert-butylbenzene (60 ml) were added into 500 mL flask. In the temperature of −78° C., n-butyl-lithium (45 mL, 37.5 mmol) was dropwisely added into the mixture, and the mixture was stirred under the temperature of 60° C. for 3 hours. Heptane was removed by blowing nitrogen at 60° C. Boron tribromide (6.3 g, 25 mmol) was dropwisely added at −78° C. The mixture was stirred at room temperature for 1 hour, and N,N-diisopropylethylamine (3.2 g, 25 mmol) was dropwisely added at 0° C. The mixture was stirred at 120° C. for 2 hours. After completion of the reaction, an aqueous sodium acetate solution was added and stirred at room temperature. After extraction with ethyl acetate, the organic layer was concentrated. The mixture was separated by column chromatography to obtain the compound 1-4 (1.9 g). (yield 23%)

3. Synthesis of the Compound 1-6

(1) The Compound I1-6c

[Reaction Formula 3-1]

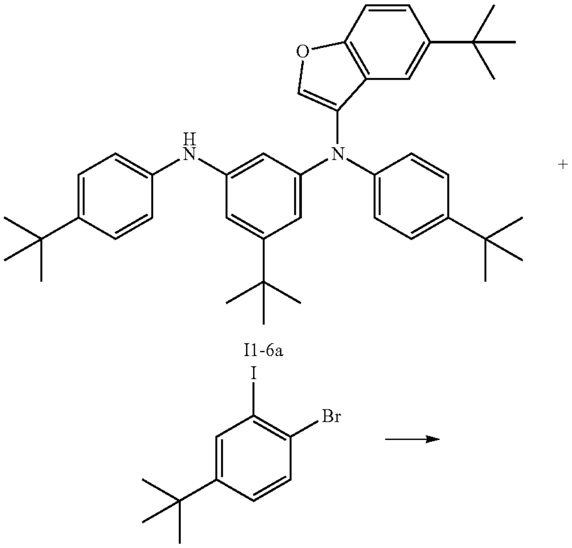

I1-6a

I1-6b

-continued

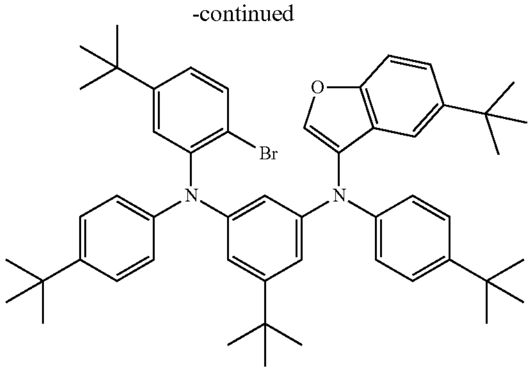

I1-6c

The compound I1-6a (58.9 g, 98 mmol), the compound I1-6b (33.2 g, 98 mmol), palladium acetate (0.45 g, 2 mmol), sodium tert-butoxide (18.9 g, 196 mmol), tri-tert-butylphosphine (0.8 g, 4 mmol), and toluene (300 mL) were added into 500 mL flask and were refluxed and stirred for 5 hours. After completion of reaction, the mixture was filtered, and residual solution was concentrated. The mixture was separated by a column chromatography to obtain the compound I1-6c (59.7 g). (yield 75%).

(2) The Compound 1-6

[Reaction Formula 3-2]

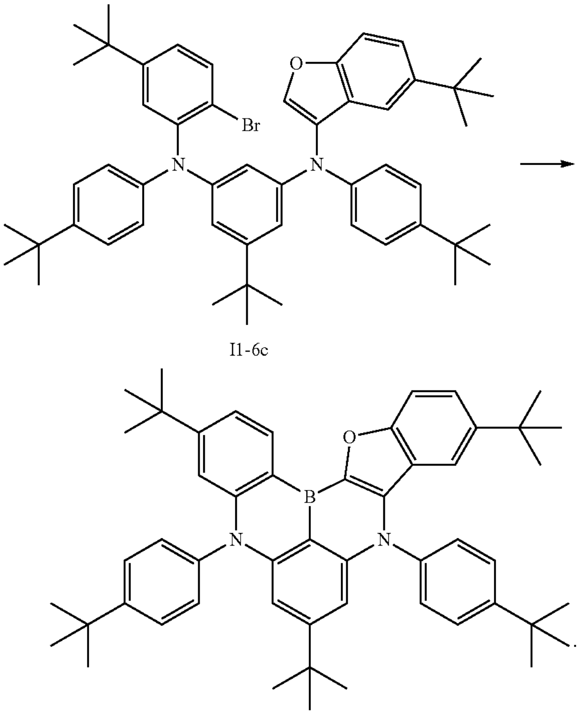

I1-6c 1-6

The compound I1-6c (10.1 g, 12.5 mmol) and tert-butylbenzene (60 ml) were added into 500 mL flask. In the temperature of −78° C., n-butyl-lithium (45 mL, 37.5 mmol) was dropwisely added into the mixture, and the mixture was stirred under the temperature of 60° C. for 3 hours. Heptane was removed by blowing nitrogen at 60° C. Boron tribromide (6.3 g, 25 mmol) was dropwisely added at −78° C. The mixture was stirred at room temperature for 1 hour, and N,N-diisopropylethylamine (3.2 g, 25 mmol) was dropwisely added at 0° C. The mixture was stirred at 120° C. for 2 hours. After completion of the reaction, an aqueous sodium acetate solution was added and stirred at room temperature. After extraction with ethyl acetate, the organic layer was concentrated. The mixture was separated by column chromatography to obtain the compound 1-6 (1.9 g). (yield 21%)

4. Synthesis of the Compound 1-8

(1) The Compound I1-8c

[Reaction Formula 4-1]

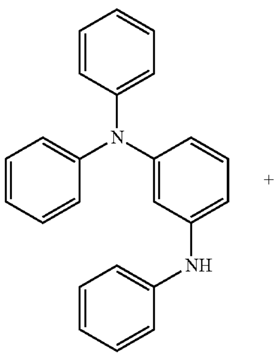

I1-8a

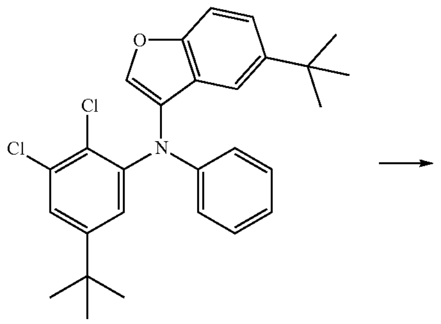

I1-8b

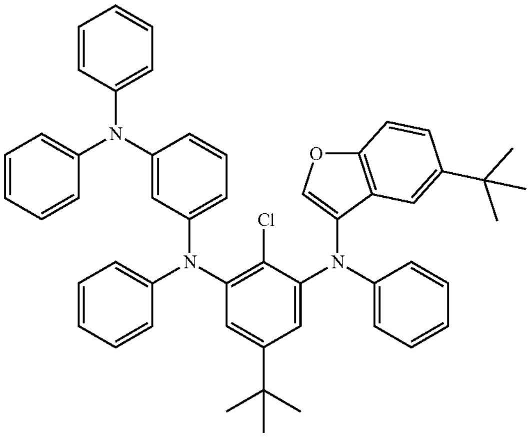

I1-8c

The compound I1-8a (33.0 g, 98 mmol), the compound I1-8b (45.7 g, 98 mmol), palladium acetate (0.45 g, 2 mmol), sodium tert-butoxide (18.9 g, 196 mmol), tri-tert-butylphosphine (0.8 g, 4 mmol), and toluene (300 mL) were added into 500 mL flask and were refluxed and stirred for 5 hours. After completion of reaction, the mixture was filtered, and residual solution was concentrated. The mixture was separated by a column chromatography to obtain the compound I1-8c (54.1 g). (yield 72%).

(2) The Compound 1-8

[Reaction Formula 4-2]

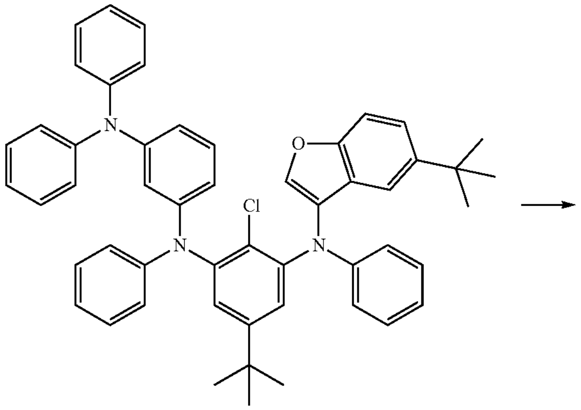

I1-8c

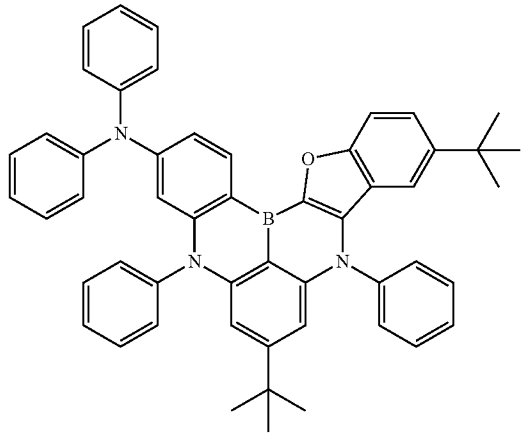

1-8

The compound I1-8c (9.6 g, 12.5 mmol) and tert-butylbenzene (60 ml) were added into 500 mL flask. In the temperature of −78° C., n-butyl-lithium (45 mL, 37.5 mmol) was dropwisely added into the mixture, and the mixture was stirred under the temperature of 60° C. for 3 hours. Heptane was removed by blowing nitrogen at 60° C. Boron tribromide (6.3 g, 25 mmol) was dropwisely added at −78° C. The mixture was stirred at room temperature for 1 hour, and N,N-diisopropylethylamine (3.2 g, 25 mmol) was dropwisely added at 0° C. The mixture was stirred at 120° C. for 2 hours. After completion of the reaction, an aqueous sodium acetate solution was added and stirred at room temperature. After extraction with ethyl acetate, the organic layer was concentrated. The mixture was separated by column chromatography to obtain the compound 1-8 (2.0 g). (yield 21%)

5. Synthesis of the Compound 1-11

(1) The Compound I1-11c

[Reaction Formula 5-1]

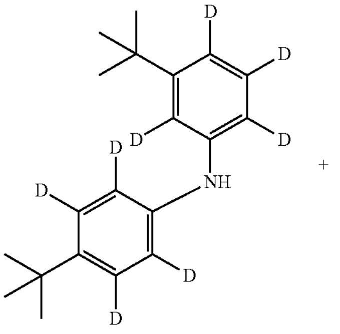

I1-11a

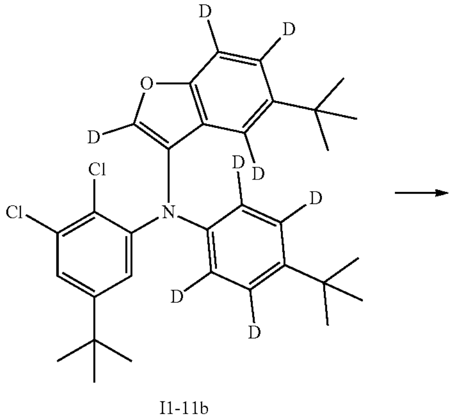

I1-11b

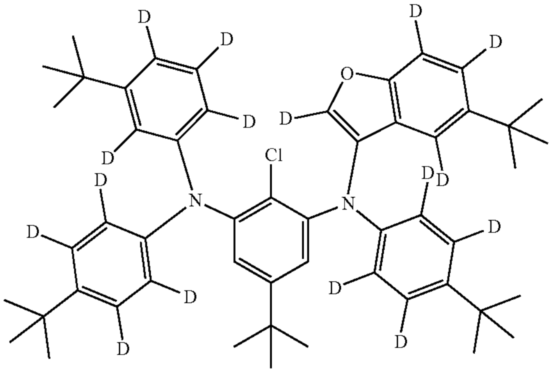

I1-11c

The compound I1-11a (28.4 g, 98 mmol), the compound I1-11b (52.0 g, 98 mmol), palladium acetate (0.45 g, 2 mmol), sodium tert-butoxide (18.9 g, 196 mmol), tri-tert-butylphosphine (0.8 g, 4 mmol), and toluene (300 mL) were added into 500 mL flask and were refluxed and stirred for 5 hours. After completion of reaction, the mixture was filtered, and residual solution was concentrated. The mixture was separated by a column chromatography to obtain the compound I1-11c (39.9 g). (yield 52%).

(2) The Compound 1-11

[Reaction Formula 5-2]

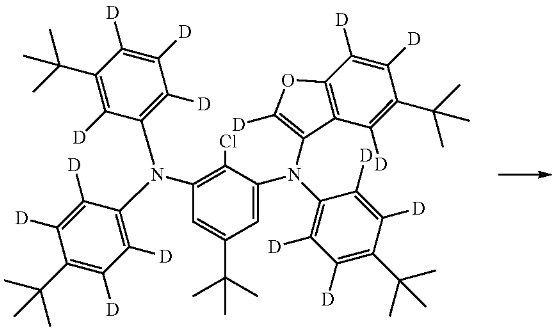

I11-3

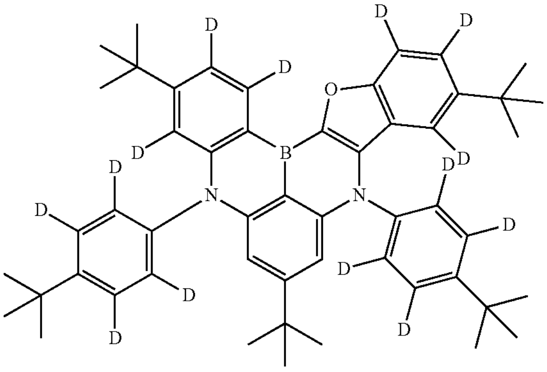

1-11

The compound I1-11c (9.8 g, 12.5 mmol) and tert-butylbenzene (60 ml) were added into 500 mL flask. In the temperature of −78° C., n-butyl-lithium (45 mL, 37.5 mmol) was dropwisely added into the mixture, and the mixture was stirred under the temperature of 60° C. for 3 hours. Heptane was removed by blowing nitrogen at 60° C. Boron tribromide (6.3 g, 25 mmol) was dropwisely added at −78° C. The mixture was stirred at room temperature for 1 hour, and N,N-diisopropylethylamine (3.2 g, 25 mmol) was dropwisely added at 0° C. The mixture was stirred at 120° C. for 2 hours. After completion of the reaction, an aqueous sodium acetate solution was added and stirred at room temperature. After extraction with ethyl acetate, the organic layer was concentrated. The mixture was separated by column chromatography to obtain the compound 1-11 (1.4 g). (yield 15%)

6. Synthesis of the Compound 1-12

(1) The Compound I1-12c

[Reaction Formula 6-1]

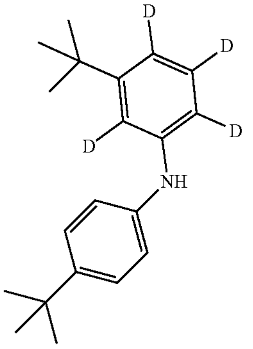

I1-12a

+

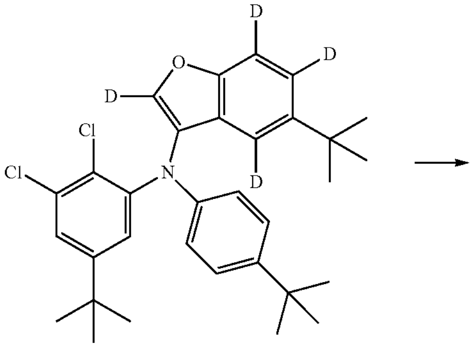

I1-12b

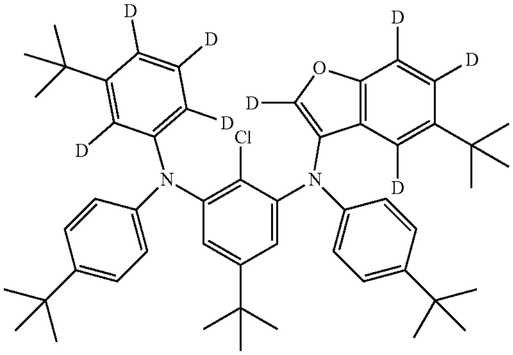

I1-12c

The compound I1-12a (28.0 g, 98 mmol), the compound I1-12b (51.6 g, 98 mmol), palladium acetate (0.45 g, 2 mmol), sodium tert-butoxide (18.9 g, 196 mmol), tri-tert-butylphosphine (0.8 g, 4 mmol), and toluene (300 mL) were added into 500 mL flask and were refluxed and stirred for 5 hours. After completion of reaction, the mixture was filtered, and residual solution was concentrated. The mixture was separated by a column chromatography to obtain the compound I1-12c (44.1 g). (yield 58%).

(2) The Compound 1-12

[Reaction Formula 6-2]

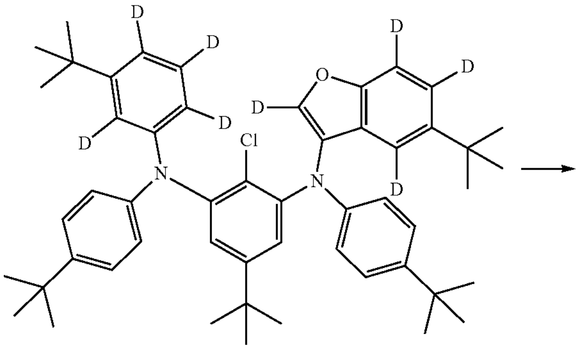

I1-12c

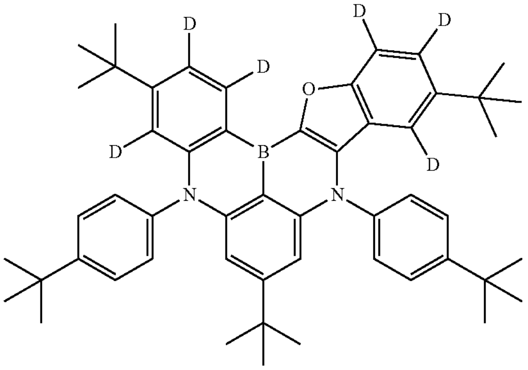

1-12

The compound I1-12c (9.7 g, 12.5 mmol) and tert-butylbenzene (60 ml) were added into 500 mL flask. In the temperature of −78° C., n-butyl-lithium (45 mL, 37.5 mmol) was dropwisely added into the mixture, and the mixture was stirred under the temperature of 60° C. for 3 hours. Heptane was removed by blowing nitrogen at 60° C. Boron tribromide (6.3 g, 25 mmol) was dropwisely added at −78° C. The mixture was stirred at room temperature for 1 hour, and N,N-diisopropylethylamine (3.2 g, 25 mmol) was dropwisely added at 0° C. The mixture was stirred at 120° C. for 2 hours. After completion of the reaction, an aqueous sodium acetate solution was added and stirred at room temperature. After extraction with ethyl acetate, the organic layer was concentrated. The mixture was separated by column chromatography to obtain the compound 1-12 (1.7 g). (yield 18%)

7. Synthesis of the Compound 1-13

(1) The Compound I1-13c

[Reaction Formula 7-1]

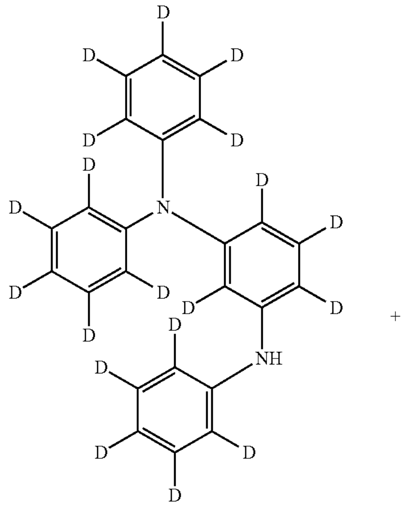

I1-13a

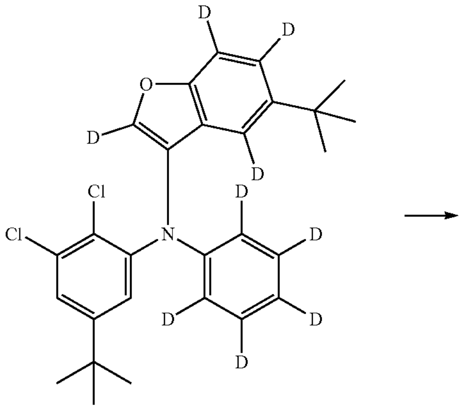

I1-13b

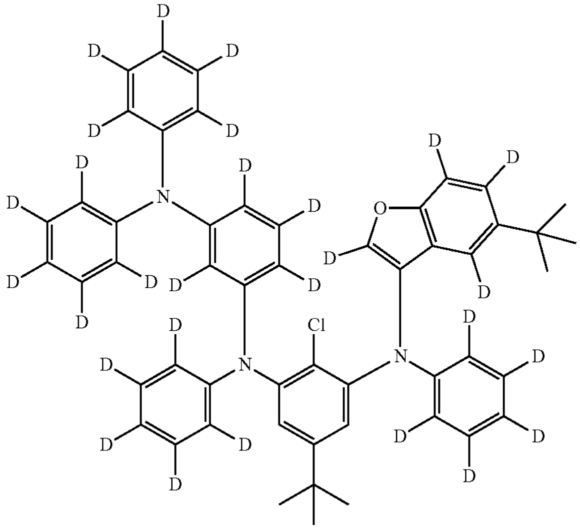

I1-13c

The compound I1-13a (34.8 g, 98 mmol), the compound I1-13b (46.6 g, 98 mmol), palladium acetate (0.45 g, 2 mmol), sodium tert-butoxide (18.9 g, 196 mmol), tri-tert-butylphosphine (0.8 g, 4 mmol), and toluene (300 mL) were added into 500 mL flask and were refluxed and stirred for 5 hours. After completion of reaction, the mixture was filtered, and residual solution was concentrated. The mixture was separated by a column chromatography to obtain the compound I1-13c (41.3 g). (yield 53%).

(2) The Compound 1-13

[Reaction Formula 7-2]

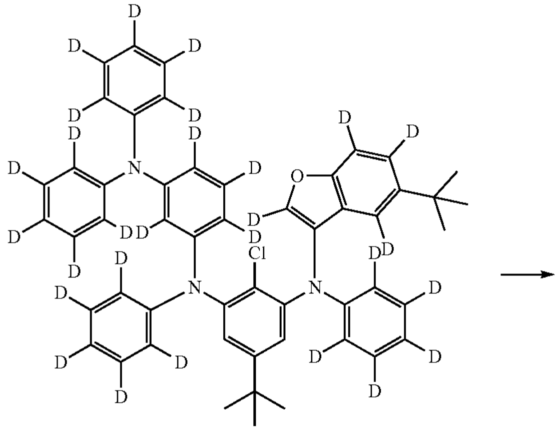

1-13C

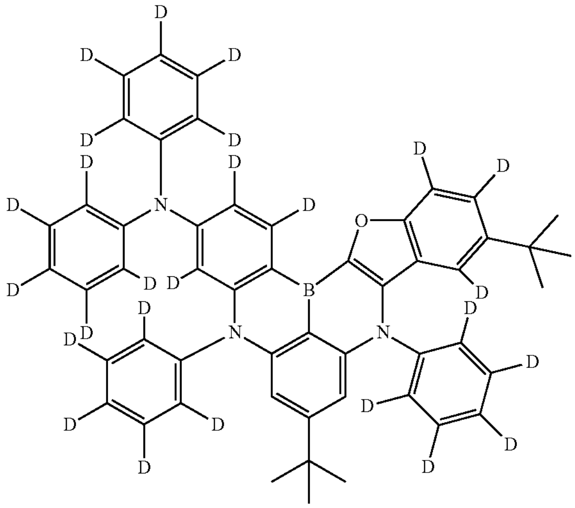

1-13

The compound I1-13c (9.9 g, 12.5 mmol) and tert-butylbenzene (60 ml) were added into 500 mL flask. In the temperature of −78° C., n-butyl-lithium (45 mL, 37.5 mmol) was dropwisely added into the mixture, and the mixture was stirred under the temperature of 60° C. for 3 hours. Heptane was removed by blowing nitrogen at 60° C. Boron tribromide (6.3 g, 25 mmol) was dropwisely added at −78° C. The mixture was stirred at room temperature for 1 hour, and N,N-diisopropylethylamine (3.2 g, 25 mmol) was dropwisely added at 0° C. The mixture was stirred at 120° C. for 2 hours. After completion of the reaction, an aqueous sodium acetate solution was added and stirred at room temperature. After extraction with ethyl acetate, the organic layer was concentrated. The mixture was separated by column chromatography to obtain the compound 1-13 (1.4 g). (yield 15%)

8. Synthesis of the Compound 1-17

(1) The Compound I1-17c

[Reaction Formula 8-1]

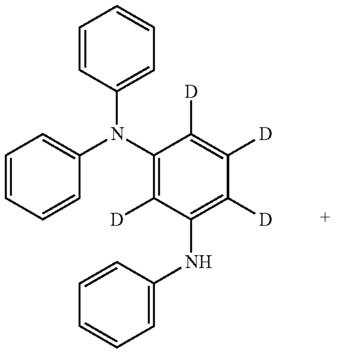

I1-17a

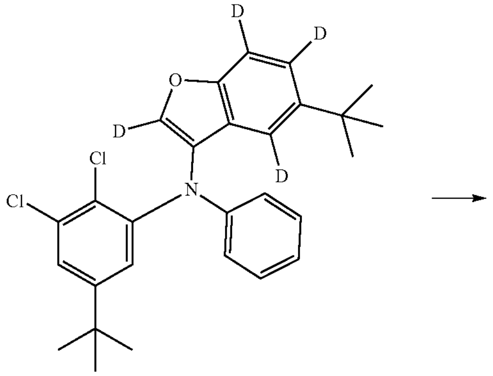

I1-17b

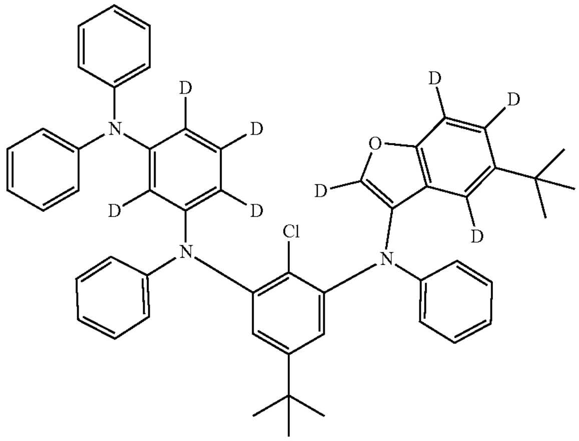

I1-17c

The compound I1-17a (33.4 g, 98 mmol), the compound I1-17b (46.1 g, 98 mmol), palladium acetate (0.45 g, 2 mmol), sodium tert-butoxide (18.9 g, 196 mmol), tri-tert-butylphosphine (0.8 g, 4 mmol), and toluene (300 mL) were added into 500 mL flask and were refluxed and stirred for 5 hours. After completion of reaction, the mixture was filtered, and residual solution was concentrated. The mixture was separated by a column chromatography to obtain the compound I1-17c (47.1 g). (yield 62%).

(2) The Compound 1-17

[Reaction Formula 8-2]

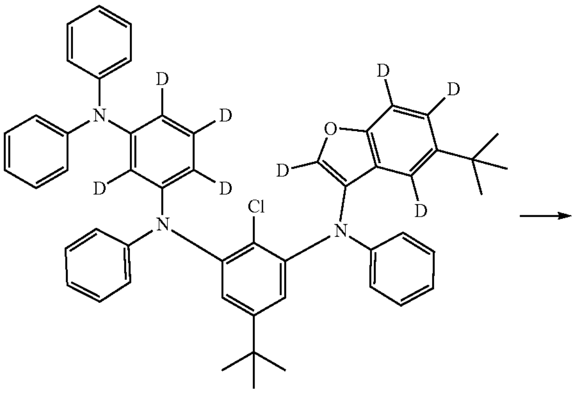

I1-17c

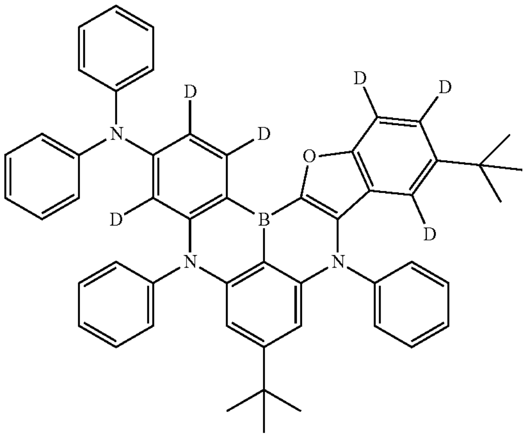

1-17

The compound I1-18c (9.7 g, 12.5 mmol) and tert-butylbenzene (60 ml) were added into 500 mL flask. In the temperature of −78° C., n-butyl-lithium (45 mL, 37.5 mmol) was dropwisely added into the mixture, and the mixture was stirred under the temperature of 60° C. for 3 hours. Heptane was removed by blowing nitrogen at 60° C. Boron tribromide (6.3 g, 25 mmol) was dropwisely added at −78° C. The mixture was stirred at room temperature for 1 hour, and N,N-diisopropylethylamine (3.2 g, 25 mmol) was dropwisely added at 0° C. The mixture was stirred at 120° C. for 2 hours. After completion of the reaction, an aqueous sodium acetate solution was added and stirred at room temperature. After extraction with ethyl acetate, the organic layer was concentrated. The mixture was separated by column chromatography to obtain the compound 1-17 (1.6 g). (yield 17%)

Synthesis of the Host

1. Synthesis of Compound 2-1

[Reaction Formula 9]

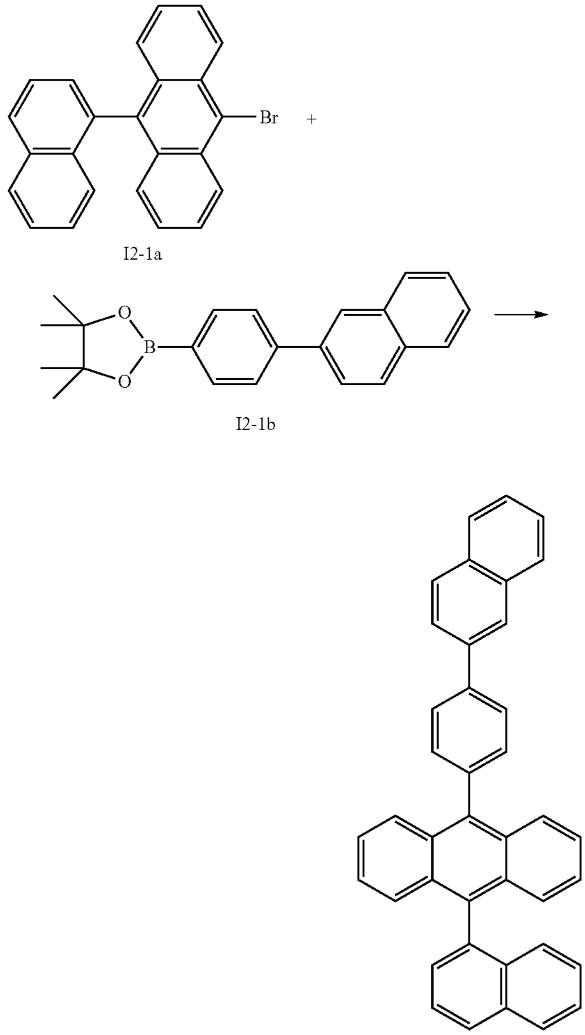

I2-1a

I2-1b 2-1

The compound 12-1a (2.0 g, 5.2 mmol), the compound 12-1b (1.5 g, 5.7 mmol), tris(dibenzylideneacetone)dipalladium(0) (0.24 g, 0.26 mmol), and toluene (50 mL) were added into a 250 mL reactor in a dry box. After the reactor is removed from the dry box, and sodium carbonate anhydrous (2M, 20 mL) was added int the mixture. The reactant was stirred and heated at 90° C. overnight. The reaction was monitored by high-performance liquid chromatography (HPLC). After the mixture was cooled to room temperature, the organic layer was separated from the mixture. The aqueous layer was washed with dichloromethane, and the organic layer was concentrated by rotary evaporation to obtain a gray powder. The gray powder was subjected to purification using alumina, precipitation using hexane, and column chromatography using silica gel to obtain the compound 2-1 (2.3 g) as a white powder. (yield 86%)

2. Synthesis of Compound 2-2

[Reaction Formula 10]

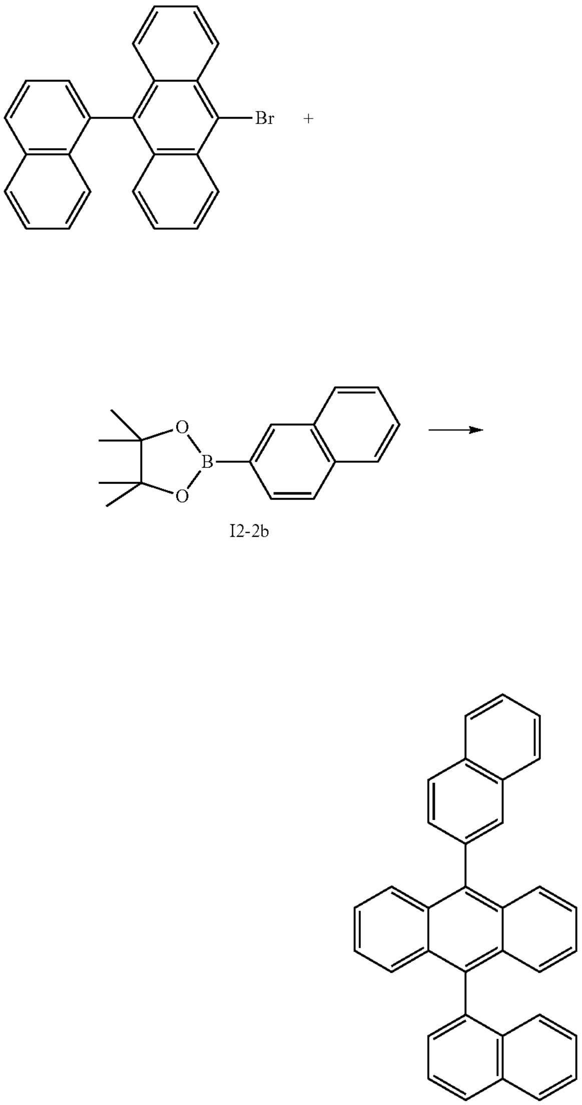

I2-2b 2-2

The compound 12-2a (2.0 g, 5.2 mmol), the compound 12-2b (1.5 g, 5.7 mmol), tris(dibenzylideneacetone)dipalladium(0) (0.24 g, 0.26 mmol), and toluene (50 mL) were added into a 250 mL reactor in a dry box. After the reactor is removed from the dry box, and sodium carbonate anhydrous (2M, 20 mL) was added int the mixture. The reactant was stirred and heated at 90° C. overnight. The reaction was monitored by high-performance liquid chromatography (HPLC). After the mixture was cooled to room temperature, the organic layer was separated from the mixture. The aqueous layer was washed with dichloromethane, and the organic layer was concentrated by rotary evaporation to obtain a gray powder. The gray powder was subjected to purification using alumina, precipitation using hexane, and column chromatography using silica gel to obtain the compound 2-2 (2.0 g) as a white powder. (yield 89%).

3. Synthesis of Compound 2-3

[Reaction Formula 11]

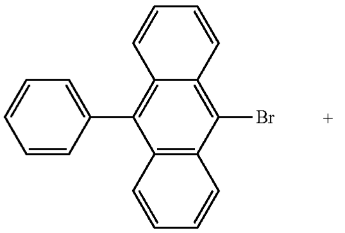

I2-3a

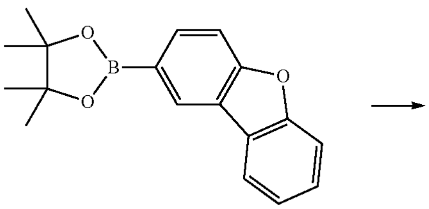

I2-3b

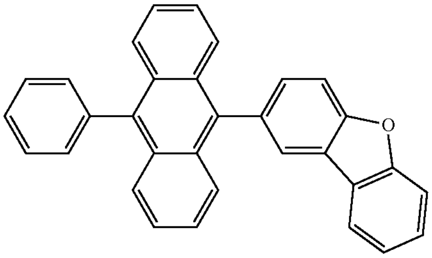

2-3

The compound I2-3a (2.0 g, 6.0 mmol), the compound 12-3b (1.9 g, 6.6 mmol), tris(dibenzylideneacetone)dipalladium(0) (0.3 g, 0.3 mmol), and toluene (50 mL) were added into a 250 mL reactor in a dry box. After the reactor is removed from the dry box, and sodium carbonate anhydrous (2M, 20 mL) was added int the mixture. The reactant was stirred and heated at 90° C. overnight. The reaction was monitored by high-performance liquid chromatography (HPLC). After the mixture was cooled to room temperature, the organic layer was separated from the mixture. The aqueous layer was washed with dichloromethane, and the organic layer was concentrated by rotary evaporation to obtain a gray powder. The gray powder was subjected to purification using alumina, precipitation using hexane, and column chromatography using silica gel to obtain the compound 2-3 (2.0 g) as a white powder. (yield 79%)

4. Synthesis of Compound 2-4

[Reaction Formula 12]

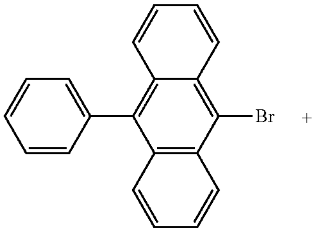

I2-4a

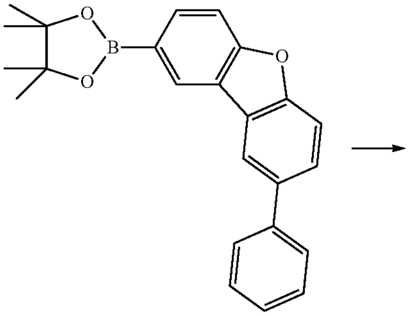

I2-4b

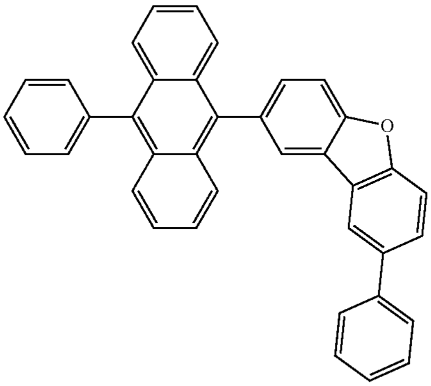

2-4

The compound 12-4a (2.0 g, 6.0 mmol), the compound 12-4b (2.4 g, 6.6 mmol), tris(dibenzylideneacetone)dipalladium(0) (0.3 g, 0.3 mmol), and toluene (50 mL) were added into a 250 mL reactor in a dry box. After the reactor is removed from the dry box, and sodium carbonate anhydrous (2M, 20 mL) was added int the mixture. The reactant was stirred and heated at 90° C. overnight. The reaction was monitored by high-performance liquid chromatography (HPLC). After the mixture was cooled to room temperature, the organic layer was separated from the mixture. The aqueous layer was washed with dichloromethane, and the organic layer was concentrated by rotary evaporation to obtain a gray powder. The gray powder was subjected to purification using alumina, precipitation using hexane, and column chromatography using silica gel to obtain the compound 2-4 (2.0 g) as a white powder. (yield 67%)

5. Synthesis of Compound 2-5

[Reaction Formula 13]

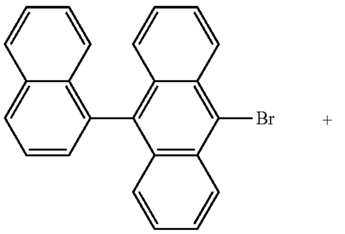

I2-5a

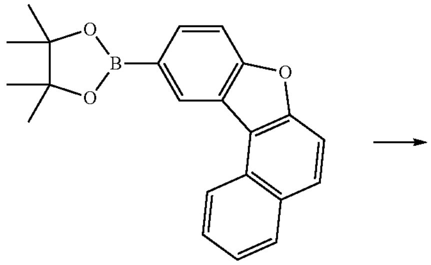

I2-5b

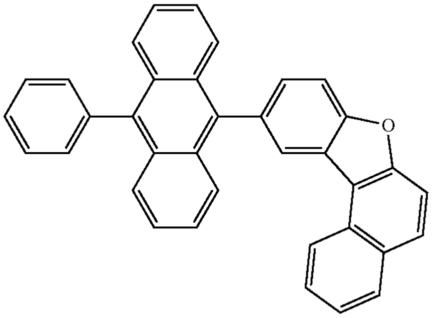

2-5

The compound 12-5a (2.0 g, 5.2 mmol), the compound 12-5b (2.0 g, 5.7 mmol), tris(dibenzylideneacetone)dipalladium(0) (0.24 g, 0.26 mmol), and toluene (50 mL) were added into a 250 mL reactor in a dry box. After the reactor is removed from the dry box, and sodium carbonate anhydrous (2M, 20 mL) was added int the mixture. The reactant was stirred and heated at 90° C. overnight. The reaction was monitored by high-performance liquid chromatography (HPLC). After the mixture was cooled to room temperature, the organic layer was separated from the mixture. The aqueous layer was washed with dichloromethane, and the organic layer was concentrated by rotary evaporation to obtain a gray powder. The gray powder was subjected to purification using alumina, precipitation using hexane, and column chromatography using silica gel to obtain the compound 2-5 (2.0 g) as a white powder. (yield 81%)

6. Synthesis of Compound 2-6

[Reaction Formula 14]

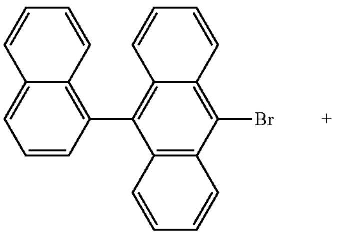

I2-6a

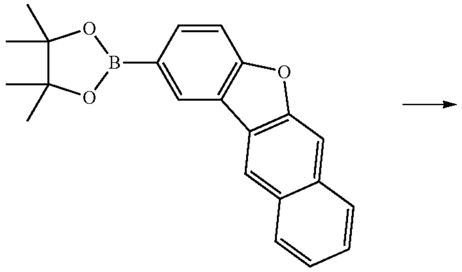

I2-6b

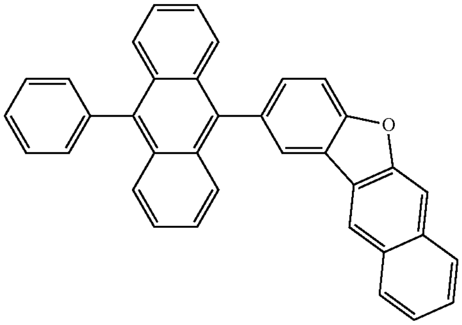

2-6

The compound 12-6a (2.0 g, 5.2 mmol), the compound 12-6b (2.0 g, 5.7 mmol), tris(dibenzylideneacetone)dipalladium(0) (0.24 g, 0.26 mmol), and toluene (50 mL) were added into a 250 mL reactor in a dry box. After the reactor is removed from the dry box, and sodium carbonate anhydrous (2M, 20 mL) was added int the mixture. The reactant was stirred and heated at 90° C. overnight. The reaction was monitored by high-performance liquid chromatography (HPLC). After the mixture was cooled to room temperature, the organic layer was separated from the mixture. The aqueous layer was washed with dichloromethane, and the organic layer was concentrated by rotary evaporation to obtain a gray powder. The gray powder was subjected to purification using alumina, precipitation using hexane, and column chromatography using silica gel to obtain the compound 2-6 (2.0 g) as a white powder. (yield 81%)

7. Synthesis of Compound 2-7

[Reaction Formula 15]

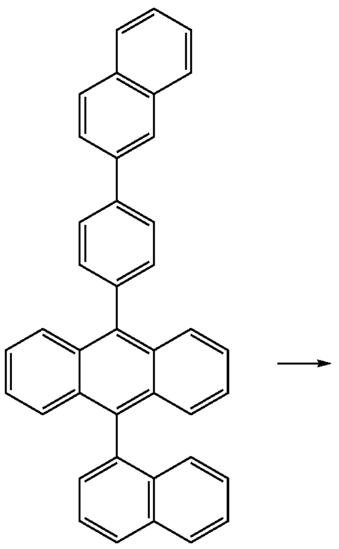

2-1

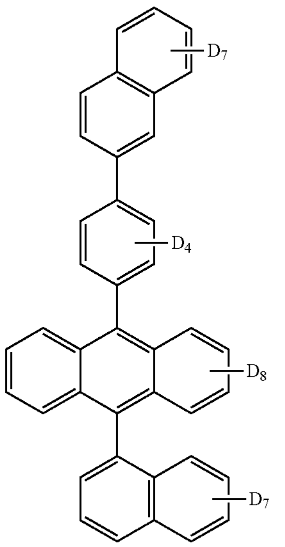

2-7

Under nitrogen condition, aluminum chloride (0.5 g, 3.6 mmol) was added into perdeuterobenzene solution (100 mL), where the compound 2-1 (5.0 g, 9.9 mmol) was dissolved. After the product by the mixture was stirred at room temperature for 6 hours, $D_2O$ (50 mL) was added. After the organic layer was separated, the aqueous layer was washed with dichloromethane (30 mL). The obtained organic layer was dried using magnesium sulfate, and volatiles were removed by rotary evaporation. Thereafter, the crude product was purified through column chromatography to obtain the compound 2-7 (4.5 g) as a white powder. (yield 85%)

8. Synthesis of Compound 2-8

[Reaction Formula 16]

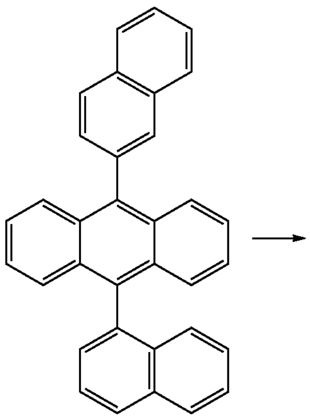

2-2

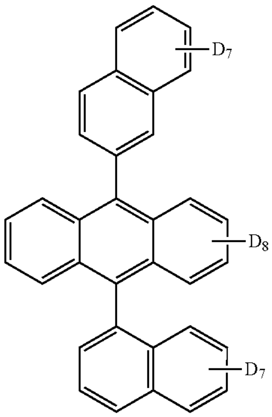

2-8

Under nitrogen condition, aluminum chloride (0.9 g, 4.3 mmol) was added into perdeuterobenzene solution (120 mL), where the compound 2-2 (5.0 g, 11.6 mmol) was dissolved. After the product by the mixture was stirred at room temperature for 6 hours, $D_2O$ (70 mL) was added. After the organic layer was separated, the aqueous layer was washed with dichloromethane (50 mL). The obtained organic layer was dried using magnesium sulfate, and volatiles were removed by rotary evaporation. Thereafter, the crude product was purified through column chromatography to obtain the compound 2-8 (4.0 g) as a white powder. (yield 76%)

9. Synthesis of Compound 2-9

[Reaction Formula 17]

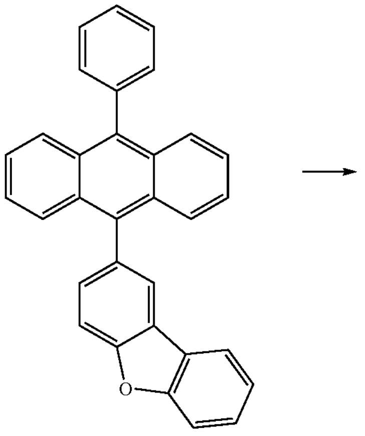

2-3

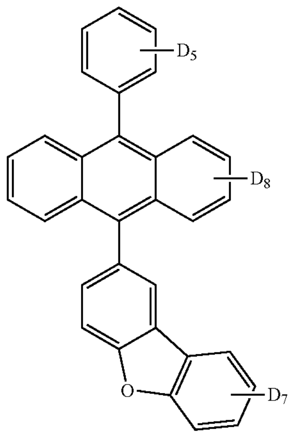

2-9

Under nitrogen condition, aluminum chloride (0.9 g, 4.3 mmol) was added into perdeuterobenzene solution (120 mL), where the compound 2-3 (5.0 g, 11.9 mmol) was dissolved. After the product by the mixture was stirred at room temperature for 6 hours, $D_2O$ (70 mL) was added. After the organic layer was separated, the aqueous layer was washed with dichloromethane (50 mL). The obtained organic layer was dried using magnesium sulfate, and volatiles were removed by rotary evaporation. Thereafter, the crude product was purified through column chromatography to obtain the compound 2-9 (3.0 g) as a white powder. (yield 57%)

10. Synthesis of Compound 2-10

[Reaction Formula 18]

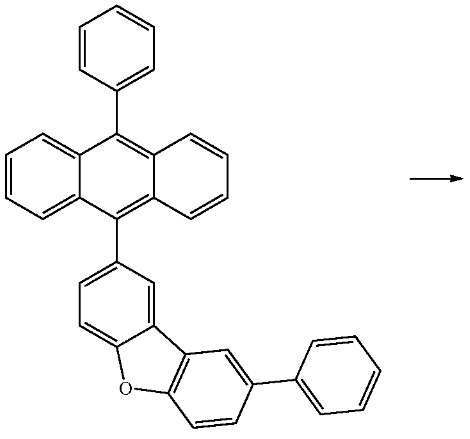

2-4

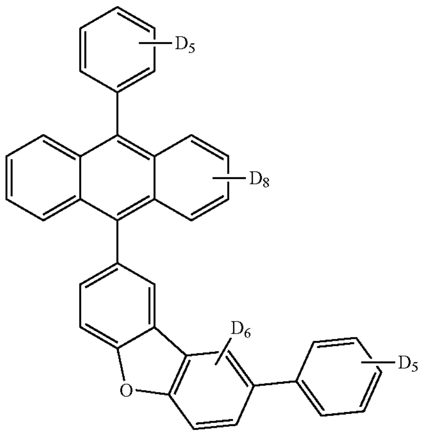

2-10

Under nitrogen condition, aluminum chloride (0.9 g, 4.3 mmol) was added into perdeuterobenzene solution (120 mL), where the compound 2-4 (5.0 g, 10.1 mmol) was dissolved. After the product by the mixture was stirred at room temperature for 6 hours, $D_2O$ (70 mL) was added. After the organic layer was separated, the aqueous layer was washed with dichloromethane (50 mL). The obtained organic layer was dried using magnesium sulfate, and volatiles were removed by rotary evaporation. Thereafter, the crude product was purified through column chromatography to obtain the compound 2-10 (3.5 g) as a white powder. (yield 67%)

11. Synthesis of Compound 2-11

[Reaction Formula 19]

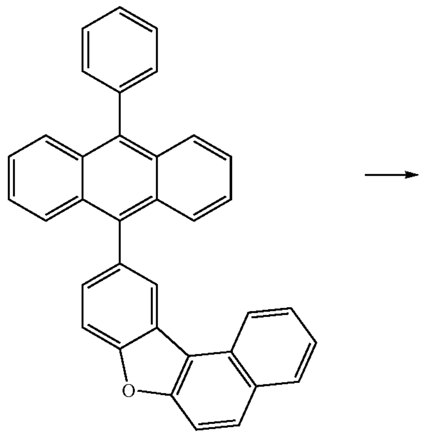

2-5

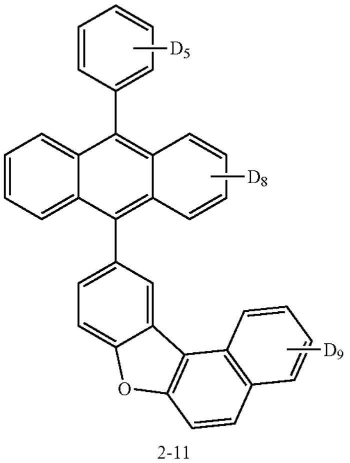

2-11

Under nitrogen condition, aluminum chloride (0.9 g, 4.3 mmol) was added into perdeuterobenzene solution (120 mL), where the compound 2-5 (5.0 g, 10.6 mmol) was dissolved. After the product by the mixture was stirred at room temperature for 6 hours, $D_2O$ (70 mL) was added. After the organic layer was separated, the aqueous layer was washed with dichloromethane (50 mL). The obtained organic layer was dried using magnesium sulfate, and volatiles were removed by rotary evaporation. Thereafter, the crude product was purified through column chromatography to obtain the compound 2-11 (4.0 g) as a white powder. (yield 77%)

12. Synthesis of Compound 2-12

[Reaction Formula 20]

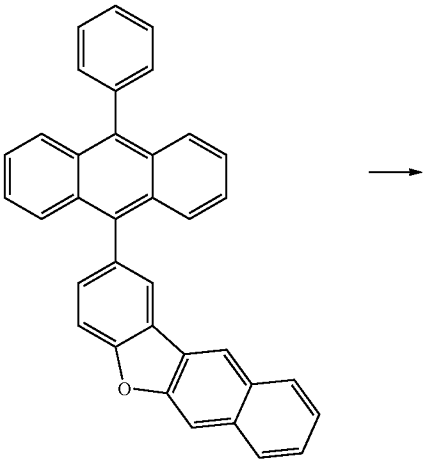

2-6

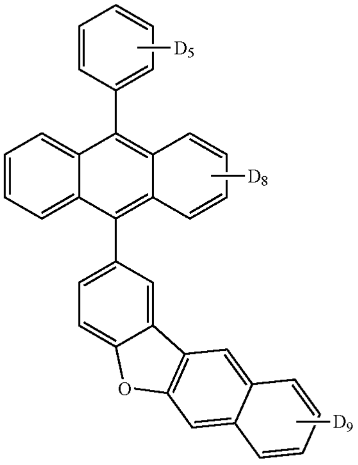

2-12

Under nitrogen condition, aluminum chloride (0.9 g, 4.3 mmol) was added into perdeuterobenzene solution (120 mL), where the compound 2-6 (5.0 g, 10.6 mmol) was dissolved. After the product by the mixture was stirred at room temperature for 6 hours, $D_2O$ (70 mL) was added. After the organic layer was separated, the aqueous layer was washed with dichloromethane (50 mL). The obtained organic layer was dried using magnesium sulfate, and volatiles were removed by rotary evaporation. Thereafter, the crude product was purified through column chromatography to obtain the compound 2-12 (4.3 g) as a white powder. (yield 82%)

The EBL 230 includes an amine derivative as an electron blocking material 232. The electron blocking material 232 may be represented by Formula 5:

[Formula 5]

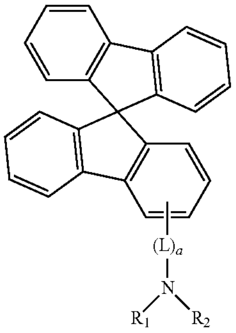

In Formula 5, L is arylene group, and a is 0 or 1. Each of $R_1$ and $R_2$ is independently selected from the group consisting of unsubstituted or substituted $C_6$ to $C_{30}$ aryl group and unsubstituted or substituted $C_5$ to $C_{30}$ heteroaryl group.

In this instance, each of $C_6$ to $C_{30}$ aryl group and $C_5$ to $C_{30}$ heteroaryl group may be substituted with $C_1$ to $C_{10}$ alkyl or $C_6$ to $C_{30}$ aryl. Namely, In Formula 5, each of $R_1$ and $R_2$ is independently selected from the group consisting of $C_6$ to $C_{30}$ aryl group unsubstituted or substituted with $C_1$ to $C_{10}$ alkyl or $C_6$ to $C_{30}$ aryl and $C_5$ to $C_{30}$ heteroaryl group unsubstituted or substituted with $C_1$ to $C_{10}$ alkyl or $C_6$ to $C_{30}$ aryl.

For example, L may be phenylene, and each of $R_1$ and $R_2$ may be selected from the group consisting of biphenyl, fluorenyl, carbazolyl, phenylcarbazolyl, carbazolylphenyl, dibenzothiophenyl and dibenzofuranyl. $C_6$ to $C_{30}$ aryl group and/or $C_5$ to $C_{30}$ heteroaryl group as $R_1$ and/or $R_2$ may be substituted by $C_1$ to $C_{10}$ alkyl or $C_6$ to $C_{30}$ aryl (e.g., phenyl)

Namely, the electron blocking material may be an amine derivative substituted with spirofluorene (e.g., "spirofluorene-substituted amine derivative").

The electron blocking material 232 of Formula 5 may be one of the followings of Formula 6:

[Formula 6]

EBL-1

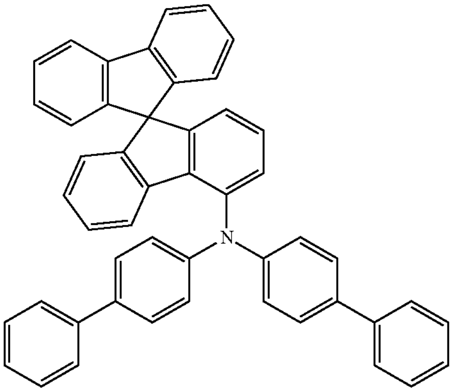

-continued

EBL-2

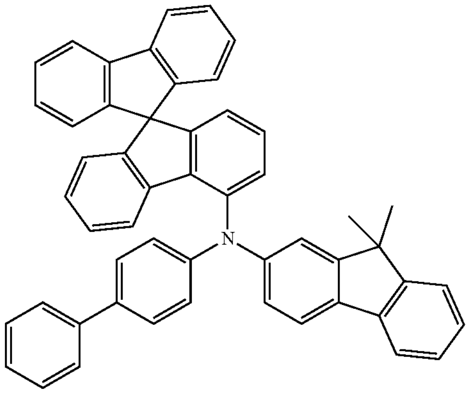

EBL-3

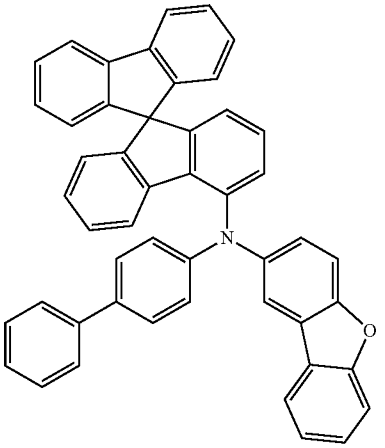

EBL-4

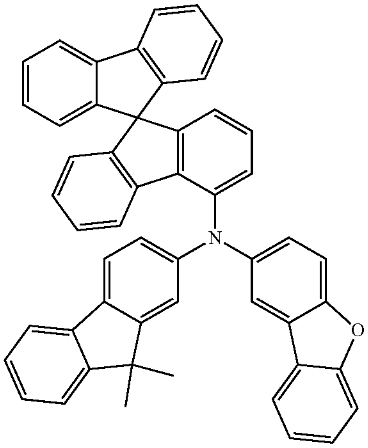

-continued
EBL-5
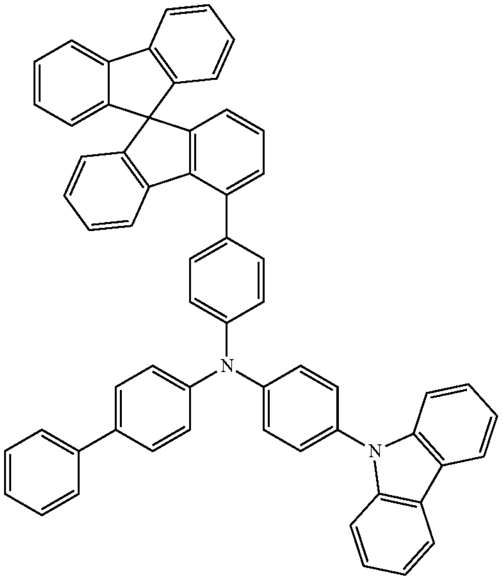
EBL-6
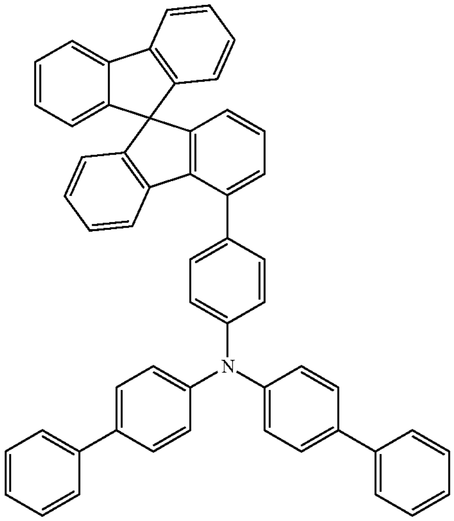
EBL-7
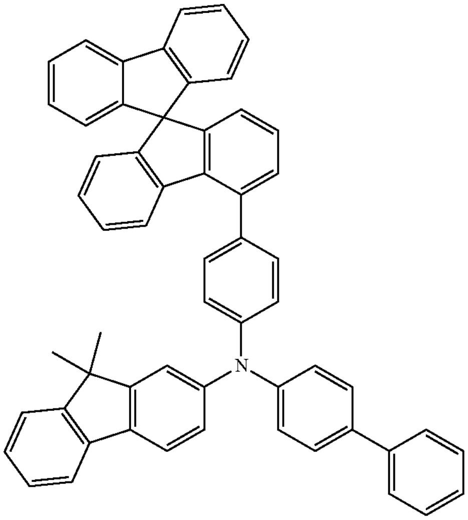
-continued
EBL-8
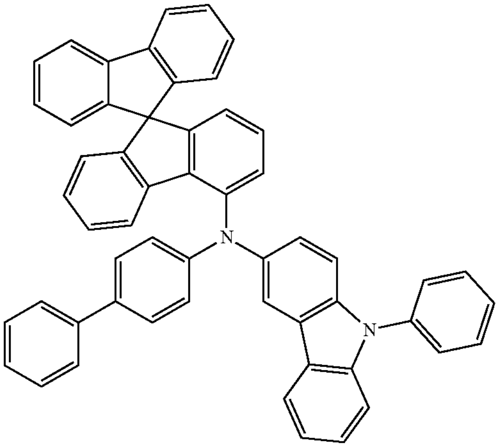
EBL-9
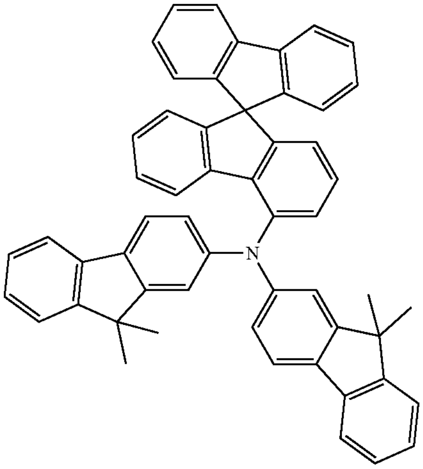
EBL-10
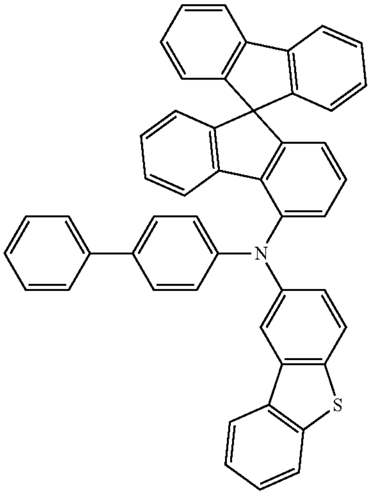

-continued

EBL-11

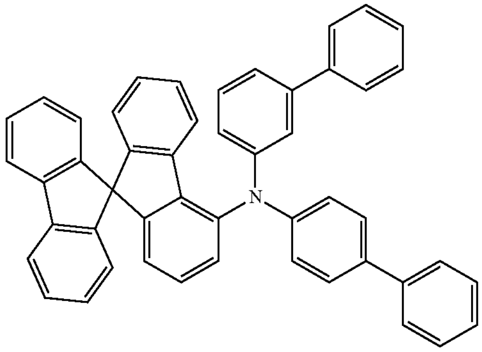

The HBL 250 includes a hole blocking material 252.

For example, the hole blocking material 252 may be an azine derivative represented by Formula 7:

[Formula 7]

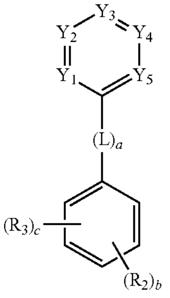

In Formula 7, each of $Y_1$ to $Y_5$ is independently $CR_1$ or N, and one to three of $Y_1$ to $Y_5$ is N. $R_1$ is independently hydrogen or $C_6$ to $C_{30}$ aryl group. L is $C_6$ to $C_{30}$ arylene group, and $R_2$ is $C_6$ to $C_{50}$ aryl group or $C_5$ to $C_{550}$ hetero aryl group. $R_3$ is $C_1$ to $C_{10}$ alkyl group, or adjacent two of $R_3$ form a fused ring. In addition, a is 0 or 1, b is 1 or 2, and c is an integer of 0 to 4.

The hole blocking material 252 of Formula 7 may be one of the followings of Formula 8:

[Formula 8]

E1

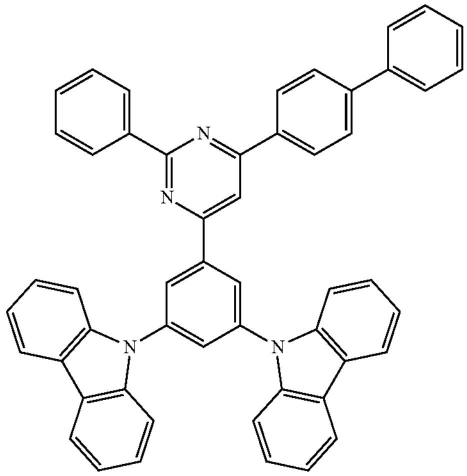

-continued

E2

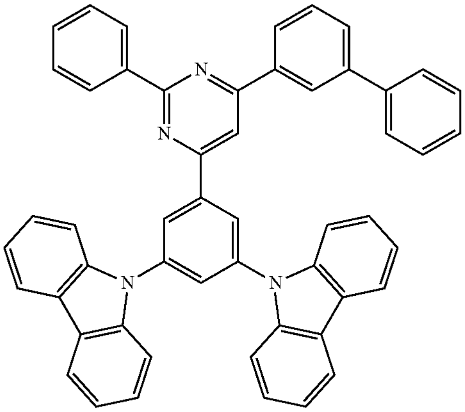

E3

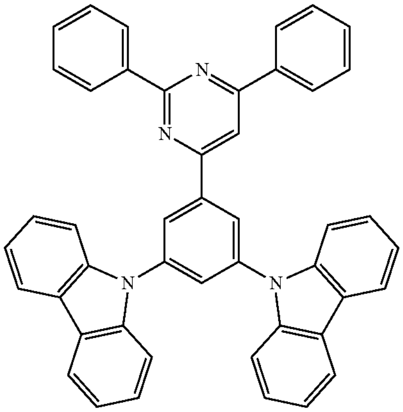

E4

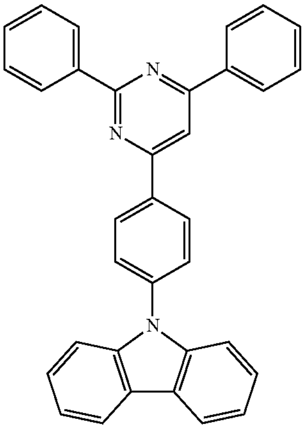

-continued
E5
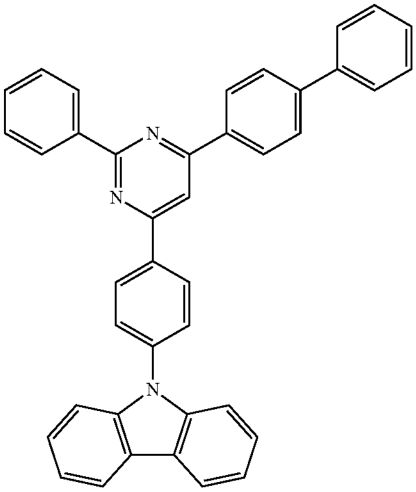
E6
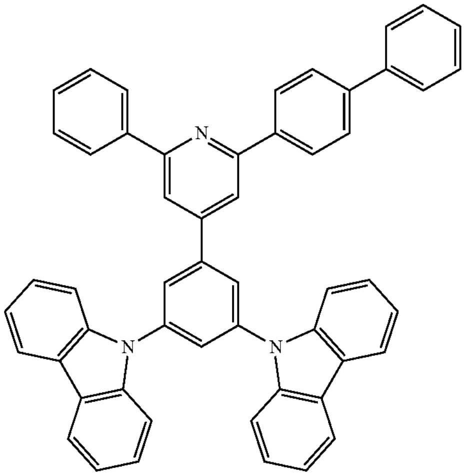
E7
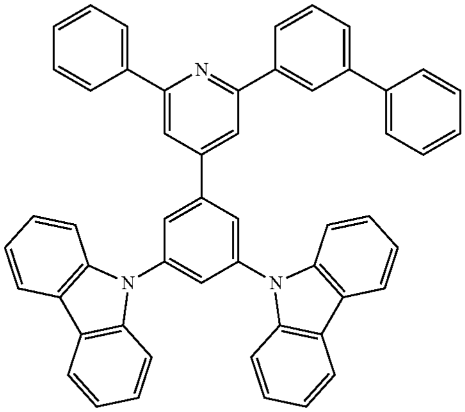
-continued
E8
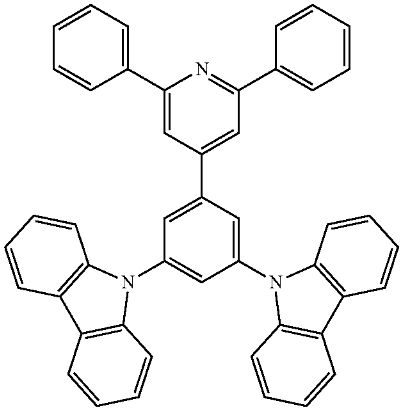
E9
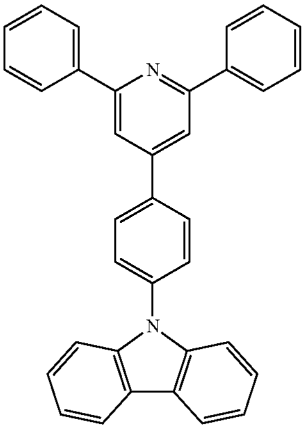
E10
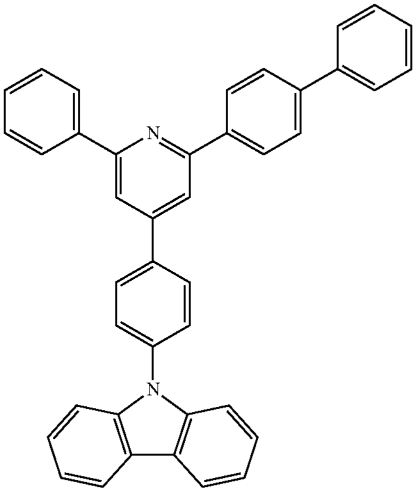

-continued
E11
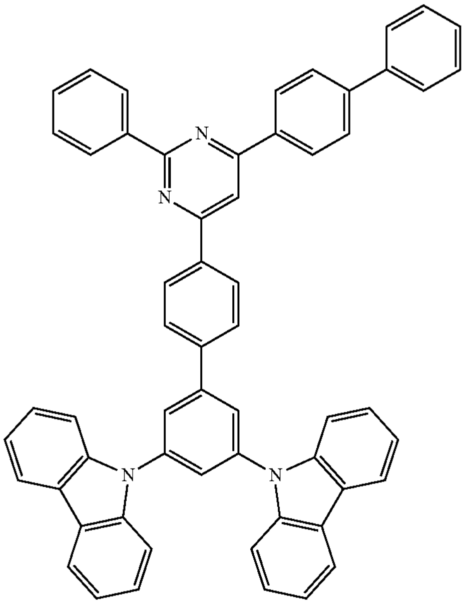
E12
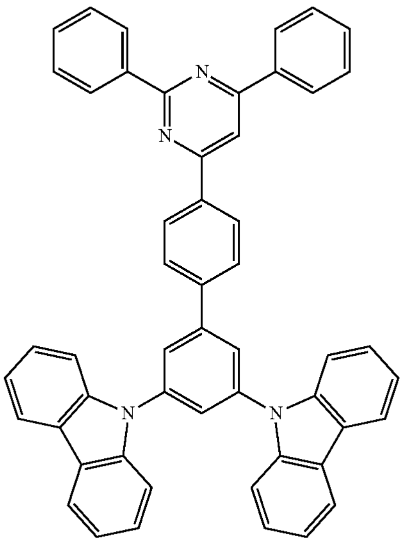
-continued
E13
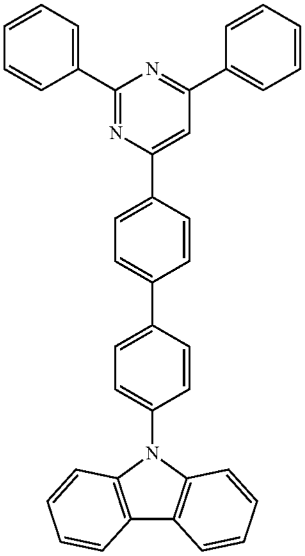
E14
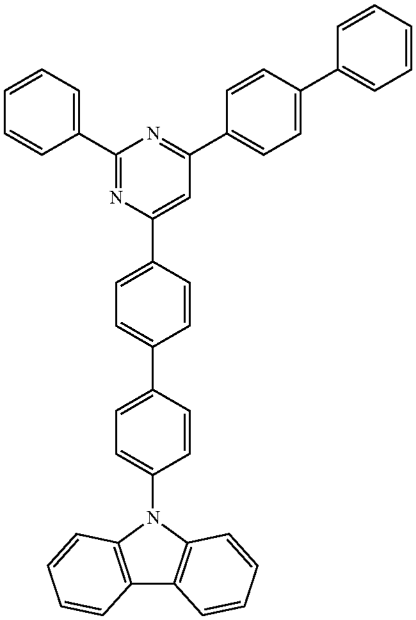
E15
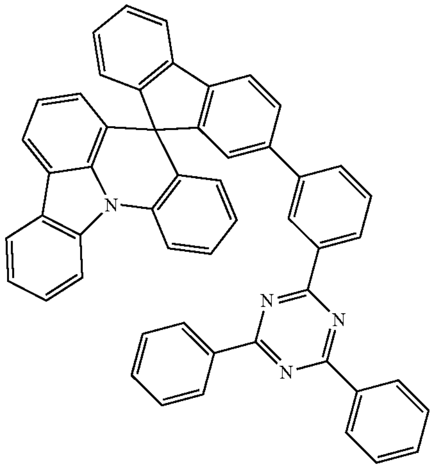

-continued
E16
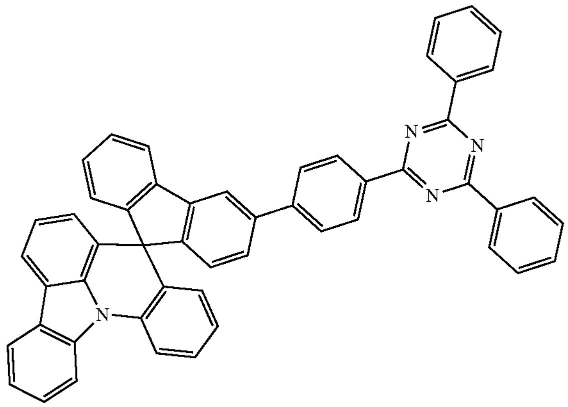
E17
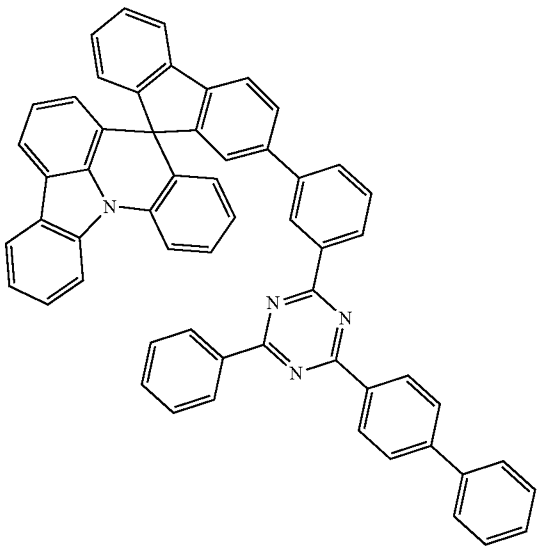
E18
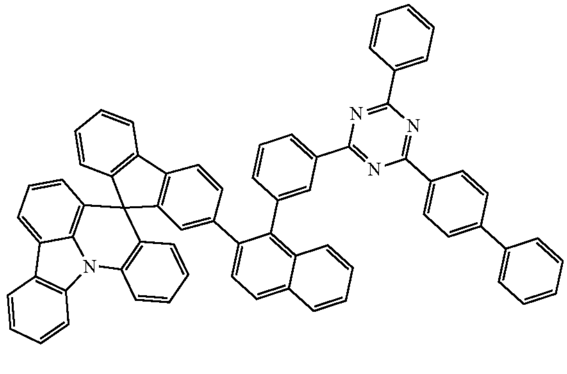
-continued
E19
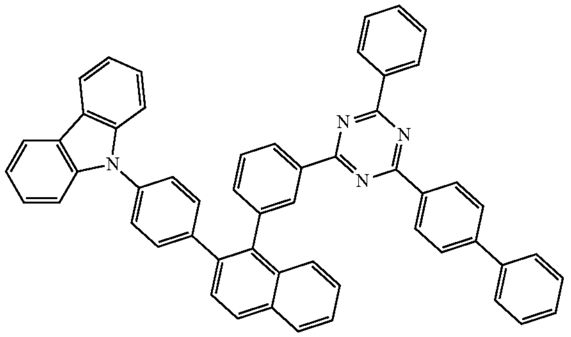
E20
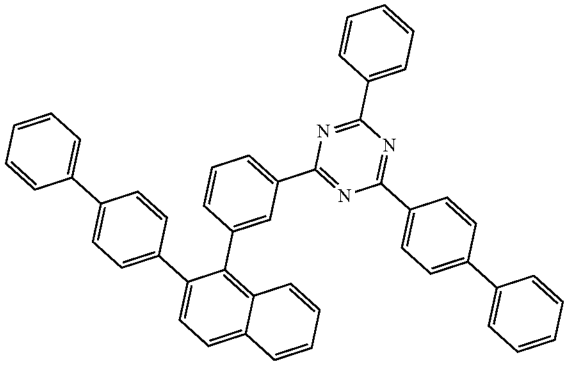
E21
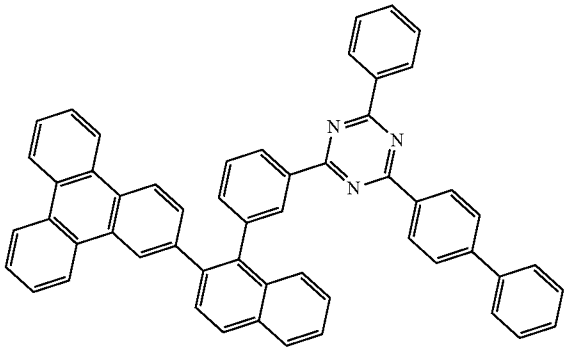
E22
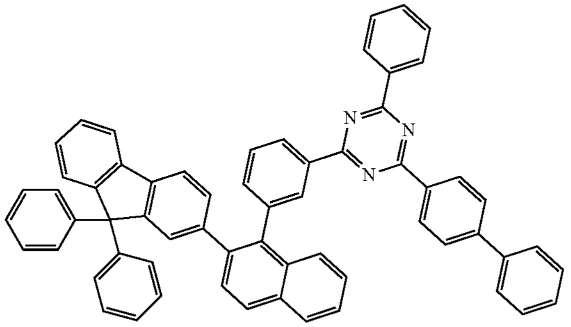

-continued

E23

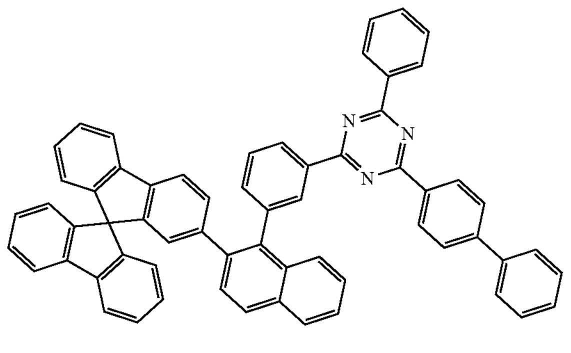

Alternatively, the hole blocking material 252 of the HBL 250 may be a benzimidazole derivative represented by Formula 9:

[Formula 9]

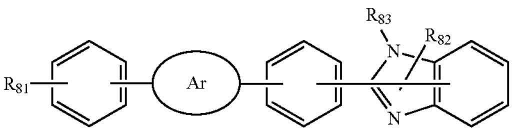

In Formula 9, Ar is $C_{10}$ to $C_{30}$ arylene group, $R_{81}$ is $C_6$ to $C_{30}$ aryl group unsubstituted or substituted with $C_1$ to $C_{10}$ alkyl group or $C_5$ to $C_{30}$ heteroaryl group unsubstituted or substituted with $C_1$ to $C_{10}$ alkyl group, and each of $R_{82}$ and $R_{83}$ is independently hydrogen, $C_1$ to $C_{10}$ alkyl group or $C_6$ to $C_{30}$ aryl group.

For example, Ar may be naphthylene or anthracenylene, $R_{81}$ may be benzimidazolyl group or phenyl. $R_{82}$ may be methyl, ethyl or phenyl, and $R_{83}$ may be hydrogen, methyl or phenyl.

The hole blocking material 252 of Formula 9 may be one of the followings of Formula 10:

[Formula 10]

F1

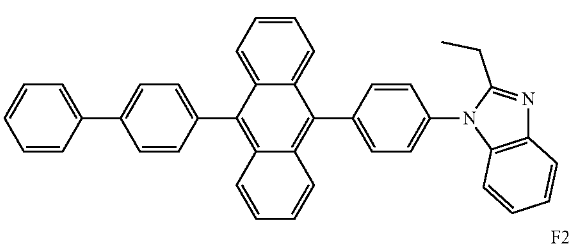

F2

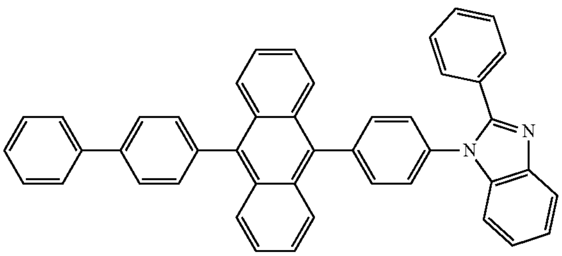

-continued

F3

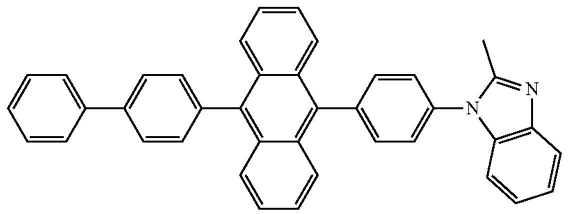

F4

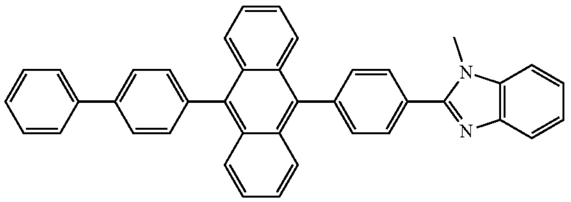

F5

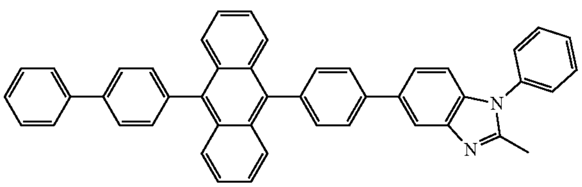

F6

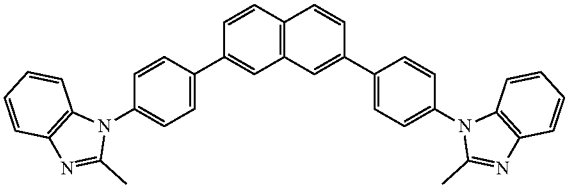

The hole blocking material 252 of the HBL 250 may include one of the compound in Formula 7 and the compound in Formula 9.

In this instance, a thickness of the EML 240 may be greater than that of each of the EBL 230 and the HBL 250 and may be smaller than that of the HTL 220. For example, the EML 240 may have a thickness of about 150 to 250 Å, each of the EBL 230 and the HBL 250 may have a thickness of about 50 to 150 Å, and the HTL 220 may have a thickness of about 900 to 1100 Å. The EBL 230 and the HBL 250 may have the same thickness.

Alternatively, the hole blocking material 252 of the HBL 250 may include both of the compound in Formula 7 and the compound in Formula 9. For example, in the HBL 250, the compound in Formula 7 and the compound in Formula 9 may have the same weight %.

In this instance, a thickness of the EML 240 may be greater than that of the EBL 230 and may be smaller than that of the HBL 250. In addition, the thickness of the HBL 250 may be smaller than that of the HTL 220. For example, the EML 240 may have a thickness of about 200 to 300 Å, and the EBL 230 may have a thickness of about 50 to 150 Å. The HBL 250 may have a thickness of about 250 to 350 Å, and the HTL 220 may have a thickness of about 800 to 1000 Å.

The compound in Formulas 7 and/or 9, i.e., the hole blocking material 252, has excellent hole blocking property and excellent electron transporting property. Accordingly, the HBL 250 may serve as a hole blocking layer as well as an electron transporting layer (ETL). In this instance, the HBL 250 may directly contact the EIL 260 without the ETL. Alternatively, the HBL 250 may directly contact the second electrode 164 without the ETL and the EIL 260.

In the OLED D, the EML 240 includes the dopant 242, which is the boron derivative, and the host 244, which is the deuterated anthracene derivative. As a result, the OLED D and the organic light emitting display device 100 have advantages in the emitting efficiency and the lifespan.

When the boron derivative as the dopant 242 has an asymmetric structure as Formula 1-2, the emitting efficiency and the lifespan of the OLED D and the organic light emitting display device 100 are further improved.

In addition, when the boron derivative as the dopant 242, in which other aromatic ring and hetero-aromatic ring except a benzene ring being combined to boron atom and two nitrogen atoms are partially or wholly deuterated, is included, the emitting efficiency and the lifespan of the OLED D and the organic light emitting display device 100 are further improved.

Moreover, when the anthracene derivative as the host 244 includes two naphthalene moieties connected to the anthracene moiety and is partially or wholly deuterated, the emitting efficiency and the lifespan of the OLED D and the organic light emitting display device 100 including the anthracene derivative are further improved.

Furthermore, since the EBL 230 includes the compound in Formula 5 as the electron blocking material 232 and the HBL 250 includes at least one of the compound in Formula 7 and the compound in Formula 9 as the hole blocking material 252, the lifespan of the OLED D and the organic light emitting display device 100 are further improved. [Organic light emitting diode 1]

The anode (ITO, 0.5 mm), the HIL (Formula 12 (97 wt %) and Formula 13 (3 wt %), 100 Å), the HTL (Formula 12, 1000 Å), the EBL (Formula 14, 100 Å), the EML (host (98 wt %) and dopant (2 wt %), 200 Å), the HBL (Formula 15, 100 Å), the EIL (Formula 16 (98 wt %) and Li (2 wt %), 200 Å) and the cathode (A1, 500 Å) was sequentially deposited. An encapsulation film is formed by using an UV curable epoxy and a moisture getter to form the OLED.

[Formula 12]

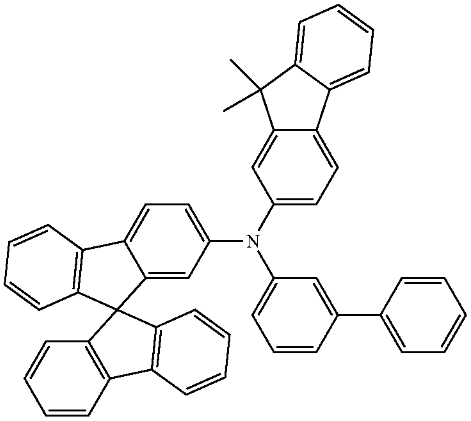

-continued

[Formula 13]

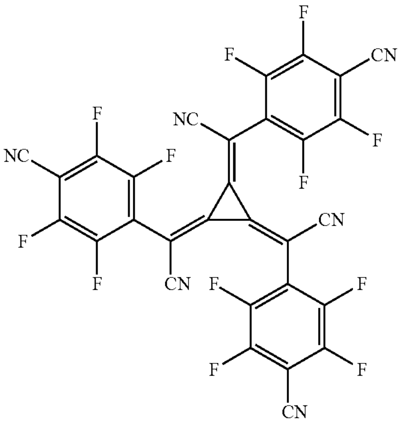

[Formula 14]

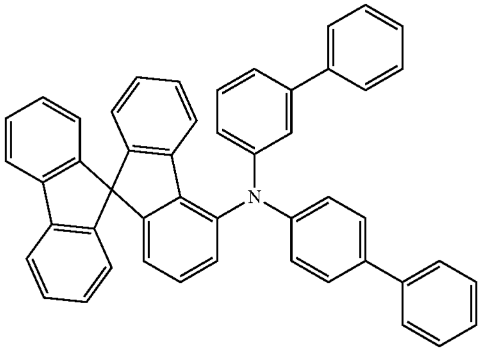

[Formula 15]

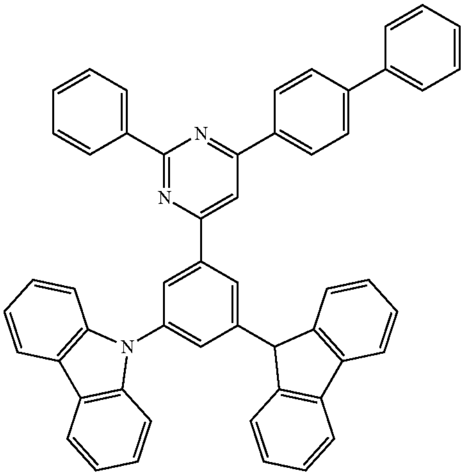

[Formula 16]

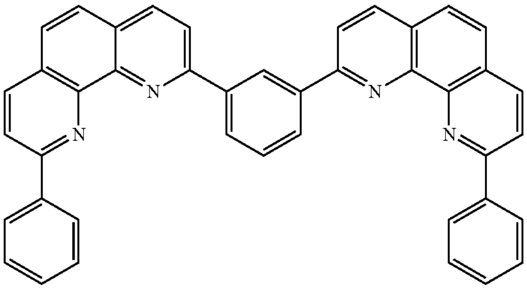

1. Comparative Examples (1) Comparative Examples 1 to 8 to Ref8)

The compound 2-1 is used as the host, and the compounds 1-1, 1-4, 1-6, 1-8, 1-11, 1-12, 1-13 and 1-17 in Formula 3 are respectively used as the dopant to form the EML.

(2) Comparative Examples 9 to 16 (Ref9 to Ref16)

The compound 2-2 is used as the host, and the compounds 1-1, 1-4, 1-6, 1-8, 1-11, 1-12, 1-13 and 1-17 in Formula 3 are respectively used as the dopant to form the EML.

(3) Comparative Examples 17 to 24 (Ref17 to Ref24)

The compound 2-3 is used as the host, and the compounds 1-1, 1-4, 1-6, 1-8, 1-11, 1-12, 1-13 and 1-17 in Formula 3 are respectively used as the dopant to form the EML.

(4) Comparative Examples 25 to 32 (Ref25 to Ref32)

The compound 2-4 is used as the host, and the compounds 1-1, 1-4, 1-6, 1-8, 1-11, 1-12, 1-13 and 1-17 in Formula 3 are respectively used as the dopant to form the EML.

(5) Comparative Examples 33 to 40 (Ref33 to Ref40)

The compound 2-5 is used as the host, and the compounds 1-1, 1-4, 1-6, 1-8, 1-11, 1-12, 1-13 and 1-17 in Formula 3 are respectively used as the dopant to form the EML.

(6) Comparative Examples 41 to 48 (Ref41 to Ref48)

The compound 2-6 is used as the host, and the compounds 1-1, 1-4, 1-6, 1-8, 1-11, 1-12, 1-13 and 1-17 in Formula 3 are respectively used as the dopant to form the EML.

2. Examples (1) Examples 1 to 8 (Ex1 to Ex8)

The compound 2-7 in Formula 4 is used as the host, and the compounds 1-1, 1-4, 1-6, 1-8, 1-11, 1-12, 1-13 and 1-17 in Formula 3 are respectively used as the dopant to form the EML.

(2) Examples 9 to 16 (Ex9 to Ex16)

The compound 2-8 in Formula 4 is used as the host, and the compounds 1-1, 1-4, 1-6, 1-8, 1-11, 1-12, 1-13 and 1-17 in Formula 3 are respectively used as the dopant to form the EML.

(3) Examples 17 to 24 (Ex17 to Ex24)

The compound 2-9 in Formula 4 is used as the host, and the compounds 1-1, 1-4, 1-6, 1-8, 1-11, 1-12, 1-13 and 1-17 in Formula 3 are respectively used as the dopant to form the EML.

(4) Examples 25 to 32 (Ex25 to Ex32)

The compound 2-10 in Formula 4 is used as the host, and the compounds 1-1, 1-4, 1-6, 1-8, 1-11, 1-12, 1-13 and 1-17 in Formula 3 are respectively used as the dopant to form the EML.

(5) Examples 33 to 40 (Ex33 to Ex40)

The compound 2-11 in Formula 4 is used as the host, and the compounds 1-1, 1-4, 1-6, 1-8, 1-11, 1-12, 1-13 and 1-17 in Formula 3 are respectively used as the dopant to form the EML.

(6) Examples 41 to 48 (Ex41 to Ex48)

The compound 2-12 in Formula 4 is used as the host, and the compounds 1-1, 1-4, 1-6, 1-8, 1-11, 1-12, 1-13 and 1-17 in Formula 3 are respectively used as the dopant to form the EML.

The properties, i.e., the driving voltage (V), the external quantum efficiency (EQE), the color coordinate (CIE) and the lifespan (T95), of the OLEDs manufactured in Comparative Examples 1 to 48 and Examples 1 to 48 are measured and listed in Tables 1 to 6.

TABLE 1

| | Dopant | Host | V | EQE (%) | CIE(x, y) | $T_{95}$ (hr) |
|---|---|---|---|---|---|---|
| Ref 1 | 1-1 | 2-1 | 3.99 | 6.35 | (0.140, 0.061) | 63 |
| Ref 2 | 1-4 | 2-1 | 3.94 | 6.33 | (0.131, 0.089) | 68 |
| Ref 3 | 1-6 | 2-1 | 3.90 | 6.61 | (0.139, 0.074) | 88 |
| Ref 4 | 1-8 | 2-1 | 3.88 | 6.63 | (0.137, 0.079) | 82 |
| Ref 5 | 1-11 | 2-1 | 3.89 | 6.61 | (0.140, 0.074) | 101 |
| Ref 6 | 1-12 | 2-1 | 3.90 | 6.59 | (0.140, 0.073) | 95 |
| Ref 7 | 1-13 | 2-1 | 3.91 | 6.64 | (0.137, 0.080) | 94 |
| Ref 8 | 1-17 | 2-1 | 3.91 | 6.58 | (0.137, 0.079) | 89 |
| Ref 9 | 1-1 | 2-2 | 4.20 | 6.24 | (0.140, 0.060) | 69 |
| Ref 10 | 1-4 | 2-2 | 4.20 | 6.22 | (0.131, 0.090) | 74 |
| Ref 11 | 1-6 | 2-2 | 4.15 | 6.49 | (0.138, 0.074) | 96 |
| Ref 12 | 1-8 | 2-2 | 4.19 | 6.51 | (0.137, 0.079) | 106 |
| Ref 13 | 1-11 | 2-2 | 4.20 | 6.50 | (0.140, 0.074) | 110 |
| Ref 14 | 1-12 | 2-2 | 4.21 | 6.47 | (0.141, 0.074) | 103 |
| Ref 15 | 1-13 | 2-2 | 4.20 | 6.53 | (0.138, 0.080) | 102 |
| Ref 16 | 1-17 | 2-2 | 4.19 | 6.47 | (0.137, 0.079) | 96 |

TABLE 2

| | Dopant | Host | V | EQE (%) | CIE(x, y) | $T_{95}$ (hr) |
|---|---|---|---|---|---|---|
| Ref 17 | 1-1 | 2-3 | 3.80 | 6.21 | (0.140, 0.063) | 56 |
| Ref 18 | 1-4 | 2-3 | 3.79 | 6.17 | (0.130, 0.092) | 61 |
| Ref 19 | 1-6 | 2-3 | 3.80 | 6.45 | (0.139, 0.076) | 79 |
| Ref 20 | 1-8 | 2-3 | 3.78 | 6.47 | (0.138, 0.081) | 73 |
| Ref 21 | 1-11 | 2-3 | 3.78 | 6.46 | (0.141, 0.075) | 90 |
| Ref 22 | 1-12 | 2-3 | 3.78 | 6.44 | (0.141, 0.075) | 85 |
| Ref 23 | 1-13 | 2-3 | 3.80 | 6.49 | (0.136, 0.081) | 84 |
| Ref 24 | 1-17 | 2-3 | 3.79 | 6.42 | (0.136, 0.081) | 79 |
| Ref 25 | 1-1 | 2-4 | 3.80 | 6.22 | (0.139, 0.062) | 56 |
| Ref 26 | 1-4 | 2-4 | 3.79 | 6.20 | (0.131, 0.092) | 60 |
| Ref 27 | 1-6 | 2-4 | 3.80 | 6.43 | (0.137, 0.081) | 80 |
| Ref 28 | 1-8 | 2-4 | 3.79 | 6.42 | (0.136, 0.084) | 73 |
| Ref 29 | 1-11 | 2-4 | 3.81 | 6.47 | (0.139, 0.076) | 91 |
| Ref 30 | 1-12 | 2-4 | 3.80 | 6.44 | (0.139, 0.077) | 84 |
| Ref 31 | 1-13 | 2-4 | 3.79 | 6.50 | (0.136, 0.084) | 83 |
| Ref 32 | 1-17 | 2-4 | 3.80 | 6.43 | (0.135, 0.087) | 80 |

TABLE 3

| | Dopant | Host | V | EQE (%) | CIE(x, y) | $T_{95}$ (hr) |
|---|---|---|---|---|---|---|
| Ref 33 | 1-1 | 2-5 | 3.65 | 6.15 | (0.140, 0.064) | 51 |
| Ref 34 | 1-4 | 2-5 | 3.61 | 6.12 | (0.130, 0.094) | 55 |
| Ref 35 | 1-6 | 2-5 | 3.62 | 6.10 | (0.138, 0.082) | 75 |
| Ref 36 | 1-8 | 2-5 | 3.60 | 6.12 | (0.138, 0.085) | 68 |
| Ref 37 | 1-11 | 2-5 | 3.62 | 6.10 | (0.141, 0.080) | 86 |
| Ref 38 | 1-12 | 2-5 | 3.63 | 6.15 | (0.141, 0.080) | 79 |
| Ref 39 | 1-13 | 2-5 | 3.62 | 6.15 | (0.136, 0.085) | 78 |
| Ref 40 | 1-17 | 2-5 | 3.63 | 6.16 | (0.136, 0.088) | 75 |
| Ref 41 | 1-1 | 2-6 | 3.65 | 6.16 | (0.140, 0.064) | 50 |
| Ref 42 | 1-4 | 2-6 | 3.60 | 6.13 | (0.130, 0.094) | 54 |
| Ref 43 | 1-6 | 2-6 | 3.61 | 6.11 | (0.138, 0.082) | 76 |
| Ref 44 | 1-8 | 2-6 | 3.59 | 6.11 | (0.138, 0.085) | 69 |
| Ref 45 | 1-11 | 2-6 | 3.61 | 6.11 | (0.141, 0.080) | 85 |
| Ref 46 | 1-12 | 2-6 | 3.62 | 6.14 | (0.141, 0.080) | 80 |
| Ref 47 | 1-13 | 2-6 | 3.61 | 6.14 | (0.136, 0.085) | 79 |
| Ref 48 | 1-17 | 2-6 | 3.62 | 6.15 | (0.136, 0.088) | 76 |

TABLE 4

| | Dopant | Host | V | EQE (%) | CIE(x, y) | $T_{95}$ (hr) |
|---|---|---|---|---|---|---|
| Ex 1 | 1-1 | 2-7 | 3.98 | 6.28 | (0.140, 0.060) | 95 |
| Ex 2 | 1-4 | 2-7 | 3.95 | 6.30 | (0.131, 0.089) | 102 |
| Ex 3 | 1-6 | 2-7 | 3.91 | 6.57 | (0.140, 0.074) | 133 |
| Ex 4 | 1-8 | 2-7 | 3.88 | 6.59 | (0.137, 0.080) | 123 |
| Ex 5 | 1-11 | 2-7 | 3.89 | 6.60 | (0.139, 0.074) | 151 |
| Ex 6 | 1-12 | 2-7 | 3.89 | 6.54 | (0.140, 0.072) | 142 |
| Ex 7 | 1-13 | 2-7 | 3.90 | 6.62 | (0.137, 0.079) | 141 |
| Ex 8 | 1-17 | 2-7 | 3.91 | 6.55 | (0.137, 0.079) | 133 |
| Ex 9 | 1-1 | 2-8 | 4.21 | 6.19 | (0.140, 0.061) | 103 |
| Ex 10 | 1-4 | 2-8 | 4.20 | 6.20 | (0.131, 0.089) | 111 |
| Ex 11 | 1-6 | 2-8 | 4.16 | 6.47 | (0.139, 0.074) | 144 |
| Ex 12 | 1-8 | 2-8 | 4.20 | 6.48 | (0.137, 0.078) | 159 |
| Ex 13 | 1-11 | 2-8 | 4.20 | 6.45 | (0.140, 0.074) | 165 |
| Ex 14 | 1-12 | 2-8 | 4.20 | 6.32 | (0.141, 0.073) | 154 |
| Ex 15 | 1-13 | 2-8 | 4.19 | 6.51 | (0.138, 0.079) | 153 |
| Ex 16 | 1-17 | 2-8 | 4.20 | 6.33 | (0.137, 0.078) | 144 |

TABLE 5

| | Dopant | Host | V | EQE (%) | CIE(x, y) | $T_{95}$ (hr) |
|---|---|---|---|---|---|---|
| Ex 17 | 1-1 | 2-9 | 3.81 | 6.21 | (0.139, 0.062) | 84 |
| Ex 18 | 1-4 | 2-9 | 3.80 | 6.19 | (0.131, 0.092) | 90 |
| Ex 19 | 1-6 | 2-9 | 3.79 | 6.42 | (0.137, 0.081) | 120 |
| Ex 20 | 1-8 | 2-9 | 3.78 | 6.41 | (0.136, 0.084) | 109 |
| Ex 21 | 1-11 | 2-9 | 3.80 | 6.45 | (0.139, 0.076) | 136 |
| Ex 22 | 1-12 | 2-9 | 3.81 | 6.42 | (0.139, 0.077) | 126 |
| Ex 23 | 1-13 | 2-9 | 3.80 | 6.49 | (0.136, 0.084) | 124 |
| Ex 24 | 1-17 | 2-9 | 3.80 | 6.41 | (0.135, 0.087) | 120 |
| Ex 25 | 1-1 | 2-10 | 3.80 | 6.21 | (0.139, 0.062) | 84 |
| Ex 26 | 1-4 | 2-10 | 3.79 | 6.22 | (0.131, 0.092) | 90 |
| Ex 27 | 1-6 | 2-10 | 3.80 | 6.42 | (0.137, 0.081) | 120 |
| Ex 28 | 1-8 | 2-10 | 3.79 | 6.41 | (0.136, 0.084) | 109 |
| Ex 29 | 1-11 | 2-10 | 3.81 | 6.45 | (0.139, 0.076) | 136 |
| Ex 30 | 1-12 | 2-10 | 3.80 | 6.45 | (0.139, 0.077) | 126 |
| Ex 31 | 1-13 | 2-10 | 3.79 | 6.49 | (0.136, 0.084) | 124 |
| Ex 32 | 1-17 | 2-10 | 3.80 | 6.42 | (0.135, 0.087) | 120 |

TABLE 6

| | Dopant | Host | V | EQE (%) | CIE(x, y) | $T_{95}$ (hr) |
|---|---|---|---|---|---|---|
| Ex 33 | 1-1 | 2-11 | 3.64 | 6.14 | (0.140, 0.064) | 76 |
| Ex 34 | 1-4 | 2-11 | 3.62 | 6.11 | (0.130, 0.094) | 82 |
| Ex 35 | 1-6 | 2-11 | 3.61 | 6.09 | (0.138, 0.082) | 112 |
| Ex 36 | 1-8 | 2-11 | 3.61 | 6.11 | (0.138, 0.085) | 102 |
| Ex 37 | 1-11 | 2-11 | 3.61 | 6.11 | (0.141, 0.080) | 129 |
| Ex 38 | 1-12 | 2-11 | 3.62 | 6.14 | (0.141, 0.080) | 119 |
| Ex 39 | 1-13 | 2-11 | 3.63 | 6.13 | (0.136, 0.085) | 117 |
| Ex 40 | 1-17 | 2-11 | 3.64 | 6.15 | (0.136, 0.088) | 112 |

TABLE 6-continued

| | Dopant | Host | V | EQE (%) | CIE(x, y) | $T_{95}$ (hr) |
|---|---|---|---|---|---|---|
| Ex 41 | 1-1 | 2-12 | 3.64 | 6.15 | (0.140, 0.064) | 75 |
| Ex 42 | 1-4 | 2-12 | 3.61 | 6.14 | (0.130, 0.094) | 81 |
| Ex 43 | 1-6 | 2-12 | 3.60 | 6.12 | (0.138, 0.082) | 114 |
| Ex 44 | 1-8 | 2-12 | 3.58 | 6.12 | (0.138, 0.085) | 103 |
| Ex 45 | 1-11 | 2-12 | 3.60 | 6.12 | (0.141, 0.080) | 127 |
| Ex 46 | 1-12 | 2-12 | 3.61 | 6.13 | (0.141, 0.080) | 120 |
| Ex 47 | 1-13 | 2-12 | 3.60 | 6.15 | (0.136, 0.085) | 118 |
| Ex 48 | 1-17 | 2-12 | 3.61 | 6.14 | (0.136, 0.088) | 114 |

As shown in Tables 1 to 6, in comparison to the OLEDs of to Ref48, each of which includes a non-deuterated anthracene derivative, e.g., the compounds 2-1 to 2-6, as a host, the emitting efficiency and the lifespan of the OLEDs of Ex1 to Ex48, each of which includes a deuterated anthracene derivative, e.g., the compounds 2-7 to 2-12, as a host are significantly improved.

In addition, in comparison to the OLEDs of Ex17 to Ex48, the emitting efficiency and the lifespan of the OLEDs of Ex1 to Ex8, each of which includes the compound 2-7 as a host, and the OLEDs of Ex9 to Ex16, each of which includes the compound 2-8 as a host, are increased. Namely, when the anthracene derivative, in which one naphthalene moiety, i.e., 1-naphthyl, is directly connected to one side of the anthracene moiety and another naphthalene moiety, i.e., 2-naphthyl, is connected to the other side of the anthracene moiety directly or through a linker, being deuterated is included as a host, the emitting efficiency and the lifespan of the OLED are increased.

In comparison to the OLEDs of Ex1 to Ex8, each of which includes the compound 2-7 as a host, the OLEDs of Ex9 to Ex16, each of which includes the compound 2-8, provides sufficient lifespan. On the other hand, the driving voltage of the OLEDs of Ex1 to Ex8, each of which includes the compound 2-7, is lowered. Namely, when the anthracene derivative, in which one naphthalene moiety, i.e., 1-naphthyl, is directly connected to one side of the anthracene moiety and another naphthalene moiety, i.e., 2-naphthyl, is connected to the other side of the anthracene moiety directly or through a linker, being deuterated is included as a host, the OLED has advantages in all of the driving voltage, the emitting efficiency and the lifespan.

In addition, in comparison to the OLEDs, which includes the boron derivative, e.g., the compound 1-1 or 1-4, having the symmetric structure, the emitting efficiency and the lifespan of the OLED, which includes the boron derivative, e.g., the compound 1-6 or 1-8, having the asymmetric structure, are improved.

Moreover, in the OLED, which includes the boron derivative, e.g., the compound 1-11, 1-12, 1-13 or 1-17, having the asymmetric structure and being deuterated, the emitting efficiency and the lifespan are further improved.

Furthermore, when each of the HIL and the HTL includes the compound in Formula 5 and the EBL includes the compound in Formula 7, the properties of the OLED are improved.

[Organic Light Emitting Diode 2]

The anode (ITO, 0.5 mm), the HIL (Formula 12 (97 wt %) and Formula 13 (3 wt %), 100 Å), the HTL (Formula 12, 1000 Å), the EBL (100 Å), the EML (host (98 wt %) and dopant (2 wt %), 200 Å), the HBL (100 Å), the EIL (Formula 16 (98 wt %) and Li (2 wt %), 200 Å) and the cathode (Al, 500 Å) was sequentially deposited. An encapsulation film is formed by using an UV curable epoxy and a moisture getter to form the OLED.

3. Comparative Examples (1) Comparative Example 49 (Ref49)

The compound "Ref. EBL" in Formula 17 is used to form the EBL, and the compound 1-6 in Formula 3 as the dopant and the compound 2-1 as the host are used to form the EML. The compound "Ref. HBL" in Formula 18 is used to form the HBL.

(2) Comparative Example 50 (Ref50)

The compound "Ref. EBL" in Formula 17 is used to form the EBL, and the compound 1-6 in Formula 3 as the dopant and the compound 2-3 as the host are used to form the EML. The compound "Ref. HBL" in Formula 18 is used to form the HBL.

(3) Comparative Example 51 (Ref51)

The compound "Ref. EBL" in Formula 17 is used to form the EBL, and the compound 1-8 in Formula 3 as the dopant and the compound 2-1 as the host are used to form the EML. The compound "Ref. HBL" in Formula 18 is used to form the HBL.

(4) Comparative Example 52 (Ref52)

The compound "Ref. EBL" in Formula 17 is used to form the EBL, and the compound 1-8 in Formula 3 as the dopant and the compound 2-3 as the host are used to form the EML. The compound "Ref. HBL" in Formula 18 is used to form the HBL.

(5) Comparative Example 53 (Ref53)

The compound "Ref. EBL" in Formula 17 is used to form the EBL, and the compound 1-11 in Formula 3 as the dopant and the compound 2-1 as the host are used to form the EML. The compound "Ref. HBL" in Formula 18 is used to form the HBL.

(6) Comparative Example 54 (Ref54)

The compound "Ref. EBL" in Formula 17 is used to form the EBL, and the compound 1-11 in Formula 3 as the dopant and the compound 2-3 as the host are used to form the EML. The compound "Ref. HBL" in Formula 18 is used to form the HBL.

(7) Comparative Example 55 (Ref55)

The compound "Ref. EBL" in Formula 17 is used to form the EBL, and the compound 1-13 in Formula 3 as the dopant and the compound 2-1 as the host are used to form the EML. The compound "Ref. HBL" in Formula 18 is used to form the HBL.

(8) Comparative Example 56 (Ref56)

The compound "Ref. EBL" in Formula 17 is used to form the EBL, and the compound 1-13 in Formula 3 as the dopant and the compound 2-3 as the host are used to form the EML. The compound "Ref. HBL" in Formula 18 is used to form the HBL.

4. Examples (1) Examples 49 to 51 (Ex49 to Ex51)

The compound "Ref. EBL" in Formula 17 is used to form the EBL, and the compound 1-6 in Formula 3 as the dopant and the compound 2-7 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(2) Examples 52 to 54 (Ex52 to Ex54)

The compound EBL-1 in Formula 6 is used to form the EBL, and the compound 1-6 in Formula 3 as the dopant and the compound 2-7 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(3) Examples 55 to 57 (Ex55 to Ex57)

The compound EBL-2 in Formula 6 is used to form the EBL, and the compound 1-6 in Formula 3 as the dopant and the compound 2-7 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(4) Examples 58 to 60 (Ex58 to Ex60)

The compound "Ref. EBL" in Formula 17 is used to form the EBL, and the compound 1-6 in Formula 3 as the dopant and the compound 2-9 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(5) Examples 61 to 63 (Ex61 to Ex63)

The compound EBL-1 in Formula 6 is used to form the EBL, and the compound 1-6 in Formula 3 as the dopant and the compound 2-9 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(6) Examples 64 to 66 (Ex64 to Ex66)

The compound EBL-2 in Formula 6 is used to form the EBL, and the compound 1-6 in Formula 3 as the dopant and the compound 2-9 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(7) Examples 67 to 69 (Ex67 to Ex69)

The compound "Ref. EBL" in Formula 17 is used to form the EBL, and the compound 1-8 in Formula 3 as the dopant and the compound 2-7 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(8) Examples 70 to 72 (Ex70 to Ex72)

The compound EBL-1 in Formula 6 is used to form the EBL, and the compound 1-8 in Formula 3 as the dopant and the compound 2-7 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(9) Examples 73 to 75 (Ex73 to Ex75)

The compound EBL-2 in Formula 6 is used to form the EBL, and the compound 1-8 in Formula 3 as the dopant and the compound 2-7 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(10) Examples 76 to 78 (Ex76 to Ex78)

The compound “Ref. EBL” in Formula 17 is used to form the EBL, and the compound 1-8 in Formula 3 as the dopant and the compound 2-9 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(11) Examples 79 to 81 (Ex79 to Ex81)

The compound EBL-1 in Formula 6 is used to form the EBL, and the compound 1-8 in Formula 3 as the dopant and the compound 2-9 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(12) Examples 82 to 84 (Ex82 to Ex84)

The compound EBL-2 in Formula 6 is used to form the EBL, and the compound 1-8 in Formula 3 as the dopant and the compound 2-9 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(13) Examples 85 to 87 (Ex85 to Ex87)

The compound “Ref. EBL” in Formula 17 is used to form the EBL, and the compound 1-11 in Formula 3 as the dopant and the compound 2-7 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(14) Examples 88 to 90 (Ex88 to Ex90)

The compound EBL-1 in Formula 6 is used to form the EBL, and the compound 1-11 in Formula 3 as the dopant and the compound 2-7 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(15) Examples 91 to 93 (Ex91 to Ex93)

The compound EBL-2 in Formula 6 is used to form the EBL, and the compound 1-11 in Formula 3 as the dopant and the compound 2-7 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(16) Examples 94 to 96 (Ex94 to Ex96)

The compound “Ref. EBL” in Formula 17 is used to form the EBL, and the compound 1-11 in Formula 3 as the dopant and the compound 2-9 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(17) Examples 97 to 99 (Ex97 to Ex99)

The compound EBL-1 in Formula 6 is used to form the EBL, and the compound 1-11 in Formula 3 as the dopant and the compound 2-9 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(18) Examples 100 to 102 (Ex100 to Ex102)

The compound EBL-2 in Formula 6 is used to form the EBL, and the compound 1-11 in Formula 3 as the dopant and the compound 2-9 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(19) Examples 103 to 105 (Ex103 to Ex105)

The compound “Ref. EBL” in Formula 17 is used to form the EBL, and the compound 1-13 in Formula 3 as the dopant and the compound 2-7 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(20) Examples 106 to 108 (Ex106 to Ex108)

The compound EBL-1 in Formula 6 is used to form the EBL, and the compound 1-13 in Formula 3 as the dopant and the compound 2-7 in Formula 4 as the host are used to form the EML. The compound “Ref. HBL” in Formula 18, the compound E1 (“HBL-1-1”) in Formula 8, the compound F1 (“HBL-2-1”) in Formula 10 are respectively used to form the HBL.

(21) Examples 109 to 111 (Ex109 to Ex111)

The compound EBL-2 in Formula 6 is used to form the EBL, and the compound 1-13 in Formula 3 as the dopant and the compound 2-7 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(22) Examples 112 to 114 (Ex112 to Ex114)

The compound "Ref. EBL" in Formula 17 is used to form the EBL, and the compound 1-13 in Formula 3 as the dopant and the compound 2-9 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(23) Examples 115 to 117 (Ex115 to Ex117)

The compound EBL-1 in Formula 6 is used to form the EBL, and the compound 1-13 in Formula 3 as the dopant and the compound 2-9 in Formula 4 as the host are used to form the EML. The compound "Ref. HBL" in Formula 18, the compound E1 ("HBL-1-1") in Formula 8, the compound F1 ("HBL-2-1") in Formula 10 are respectively used to form the HBL.

(24) Examples 118 to 120 (Ex118 to Ex120)

The compound EBL-2 in Formula 6 is used to form the EBL, and the compound 1-13 in Formula 3 as the dopant and the compound 2-9 in Formula 4 as the host are used to form the EML. The compound "Ref" in Formula 18, the compound E1 ("HBL-1-1") in Formula 8, the compound F1 ("HBL-2-1") in Formula 10 are respectively used to form the HBL.

[Formula 17]

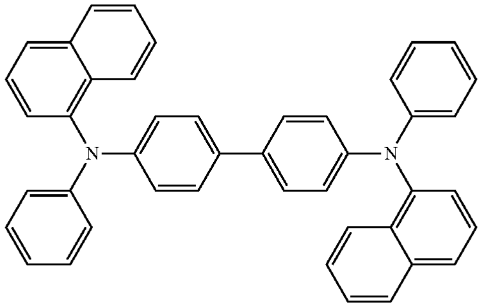

Ref. EBL

[Formula 18]

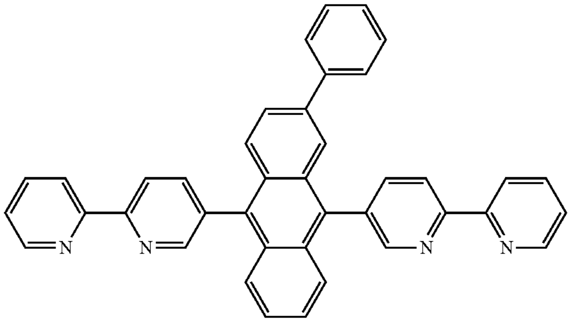

Ref. HBL

The properties, i.e., the driving voltage (V), the external quantum efficiency (EQE), the color coordinate (CIE) and the lifespan (T95), of the OLEDs manufactured in Comparative Examples 49 to 56 and Examples 49 to 120 are measured and listed in Tables 7 to 14.

TABLE 7

| | EBL | D | H | HBL | V | EQE (%) | CIE(x) | CIE(y) | $T_{95}$ (hr) |
|---|---|---|---|---|---|---|---|---|---|
| Ref49 | Ref. | 1-6 | 2-1 | Ref. | 3.93 | 3.11 | 0.140 | 0.076 | 26 |
| Ex49 | Ref. | 1-6 | 2-7 | Ref. | 3.95 | 3.09 | 0.140 | 0.075 | 45 |
| Ex50 | Ref. | 1-6 | 2-7 | HBL-1-1 | 3.95 | 3.14 | 0.141 | 0.074 | 54 |
| Ex51 | Ref. | 1-6 | 2-7 | HBL-2-1 | 3.91 | 3.19 | 0.140 | 0.075 | 61 |
| Ex52 | EBL-1 | 1-6 | 2-7 | Ref. | 3.96 | 6.13 | 0.140 | 0.076 | 122 |
| Ex53 | EBL-1 | 1-6 | 2-7 | HBL-1-1 | 3.91 | 6.27 | 0.140 | 0.074 | 161 |
| Ex54 | EBL-1 | 1-6 | 2-7 | HBL-2-1 | 3.91 | 6.38 | 0.140 | 0.074 | 190 |
| Ex55 | EBL-2 | 1-6 | 2-7 | Ref. | 3.93 | 6.45 | 0.139 | 0.077 | 110 |
| Ex56 | EBL-2 | 1-6 | 2-7 | HBL-1-1 | 3.92 | 6.58 | 0.140 | 0.074 | 150 |
| Ex57 | EBL-2 | 1-6 | 2-7 | HBL-2-1 | 3.92 | 6.70 | 0.140 | 0.074 | 177 |

TABLE 8

| | EBL | D | H | HBL | V | EQE (%) | CIE(x) | CIE(y) | $T_{95}$ (hr) |
|---|---|---|---|---|---|---|---|---|---|
| Ref50 | Ref. | 1-6 | 2-3 | Ref. | 3.82 | 3.01 | 0.139 | 0.076 | 28 |
| Ex50 | Ref. | 1-6 | 2-9 | Ref. | 3.84 | 3.03 | 0.138 | 0.061 | 38 |
| Ex59 | Ref. | 1-6 | 2-9 | HBL-1-1 | 3.81 | 3.09 | 0.137 | 0.080 | 49 |
| Ex60 | Ref. | 1-6 | 2-9 | HBL-2-1 | 3.82 | 3.19 | 0.138 | 0.061 | 58 |
| Ex61 | EBL-1 | 1-6 | 2-9 | Ref. | 3.85 | 6.05 | 0.138 | 0.081 | 112 |
| Ex62 | EBL-1 | 1-6 | 2-9 | HBL-1-1 | 3.79 | 6.13 | 0.137 | 0.061 | 145 |
| Ex63 | EBL-1 | 1-6 | 2-9 | HBL-2-1 | 3.80 | 6.31 | 0.137 | 0.082 | 174 |
| Ex64 | EBL-2 | 1-6 | 2-9 | Ref. | 3.83 | 6.36 | 0.138 | 0.061 | 106 |
| Ex65 | EBL-2 | 1-6 | 2-9 | HBL-1-1 | 3.79 | 6.41 | 0.138 | 0.079 | 136 |
| Ex66 | EBL-2 | 1-6 | 2-9 | HBL-2-1 | 3.80 | 6.60 | 0.137 | 0.082 | 169 |

TABLE 9

| | EBL | D | H | HBL | V | EQE (%) | CIE(x) | CIE(y) | $T_{95}$ (hr) |
|---|---|---|---|---|---|---|---|---|---|
| Ref51 | Ref. | 1-8 | 2-1 | Ref. | 3.92 | 3.12 | 0.136 | 0.081 | 28 |
| Ex67 | Ref. | 1-8 | 2-7 | Ref. | 3.93 | 3.08 | 0.139 | 0.082 | 42 |
| Ex68 | Ref. | 1-8 | 2-7 | HBL-1-1 | 3.87 | 3.17 | 0.137 | 0.081 | 50 |
| Ex69 | Ref. | 1-8 | 2-7 | HBL-2-1 | 3.91 | 3.22 | 0.137 | 0.082 | 59 |
| Ex70 | EBL-1 | 1-8 | 2-7 | Ref. | 3.92 | 6.17 | 0.138 | 0.081 | 119 |
| Ex71 | EBL-1 | 1-8 | 2-7 | HBL-1-1 | 3.88 | 6.29 | 0.137 | 0.080 | 149 |
| Ex72 | EBL-1 | 1-8 | 2-7 | HBL-2-1 | 3.89 | 6.44 | 0.137 | 0.081 | 175 |
| Ex73 | EBL-2 | 1-8 | 2-7 | Ref. | 3.90 | 6.48 | 0.138 | 0.081 | 118 |
| Ex74 | EBL-2 | 1-8 | 2-7 | HBL-1-1 | 3.88 | 6.67 | 0.130 | 0.081 | 142 |
| Ex75 | EBL-2 | 1-8 | 2-7 | HBL-2-1 | 3.89 | 6.72 | 0.136 | 0.082 | 157 |

TABLE 10

| | EBL | D | H | HBL | V | EQE (%) | CIE(x) | CIE(y) | $T_{95}$ (hr) |
|---|---|---|---|---|---|---|---|---|---|
| Ref52 | Ref. | 1-3 | 2-3 | Ref. | 3.80 | 3.05 | 0.137 | 0.001 | 27 |
| Ex76 | Ref. | 1-8 | 2-9 | Ref. | 3.81 | 3.07 | 0.138 | 0.083 | 36 |
| Ex77 | Ref. | 1-8 | 2-9 | HBL-1-1 | 3.76 | 3.06 | 0.137 | 0.083 | 42 |
| Ex78 | Ref. | 1-8 | 2-9 | HBL-2-1 | 3.80 | 4.18 | 0.137 | 0.083 | 52 |
| Ex79 | EBL-1 | 1-8 | 2-9 | Ref. | 3.82 | 6.05 | 0.137 | 0.083 | 107 |
| Ex80 | EBL-1 | 1-8 | 2-9 | HBL-1-1 | 3.78 | 6.12 | 0.136 | 0.084 | 132 |
| Ex81 | EBL-1 | 1-8 | 2-9 | HBL-2-1 | 3.79 | 6.30 | 0.136 | 0.084 | 156 |
| Ex82 | EBL-2 | 1-8 | 2-9 | Ref. | 3.84 | 6.38 | 0.137 | 0.083 | 102 |
| Ex83 | EBL-2 | 1-8 | 2-9 | HBL-1-1 | 3.76 | 6.42 | 0.136 | 0.084 | 129 |
| Ex84 | EBL-2 | 1-8 | 2-9 | HBL-2-1 | 3.81 | 6.62 | 0.136 | 0.083 | 144 |

TABLE 11

| | EBL | D | H | HBL | V | EQE (%) | CIE(x) | CIE(y) | $T_{95}$ (hr) |
|---|---|---|---|---|---|---|---|---|---|
| Ref53 | Ref. | 1-11 | 2-1 | Ref. | 3.95 | 3.08 | 0.141 | 0.076 | 40 |
| Ex85 | Ref. | 1-11 | 2-7 | Ref. | 3.94 | 3.04 | 0,140 | 0.074 | 68 |
| Ex86 | Ref. | 1-11 | 2-7 | HPL-1-1 | 3.94 | 3.09 | 0.140 | 0.076 | 80 |
| Ex87 | Ref. | 1-11 | 2-7 | HBL-2-1 | 3.90 | 3.14 | 0.140 | 0.076 | 92 |
| Ex88 | EEL-1 | 1-11 | 2-7 | Pet | 3.93 | 6.10 | 0.140 | 0.076 | 203 |
| Ex89 | EBL-1 | 1-11 | 2-7 | HBL-1-1 | 3.94 | 6.18 | 0.140 | 0.076 | 241 |
| Ex90 | EBL-1 | 1-11 | 2-7 | HBL-2-1 | 3.90 | 6.28 | 0.140 | 0.076 | 275 |
| Ex91 | EBL-2 | 1-11 | 2-7 | Ref. | 3.93 | 6.39 | 0.140 | 0.076 | 165 |
| Ex92 | EBL-2 | 1-11 | 2-7 | HBL-1-1 | 3.92 | 6.54 | 0.139 | 0.076 | 225 |
| Ex93 | EBL-2 | 1-11 | 2-7 | HBL-2-1 | 3.91 | 6.72 | 0.140 | 0.074 | 266 |

TABLE 12

| | EBL | D | H | HBL | V | EQE (%) | CIE(x) | CIE(y) | $T_{95}$ (hr) |
|---|---|---|---|---|---|---|---|---|---|
| Ref54 | Ref. | 1-11 | 2-3 | Ref. | 3.83 | 2.99 | 0.140 | 0.077 | 42 |
| Ex94 | Ref. | 1-11 | 2-9 | Ref. | 3.82 | 2.98 | 0.138 | 0.083 | 57 |
| Ex95 | Ref. | 1-11 | 2-9 | HBL-1-1 | 3.82 | 3.04 | 0.137 | 0.080 | 74 |
| Ex96 | Ref. | 1-11 | 2-9 | HBL-2-1 | 3.84 | 3.20 | 0.138 | 0.023 | 87 |
| Ex97 | EBL-1 | 1-11 | 2-9 | Ref. | 3.82 | 5.96 | 0.138 | 0.083 | 171 |
| Ex98 | EBL-1 | 1-11 | 2-9 | HBL-1-1 | 3.82 | 6.08 | 0.137 | 0.080 | 221 |
| Ex99 | EBL-1 | 1-11 | 2-9 | HBL-2-1 | 3.85 | 6.44 | 0.138 | 0.083 | 261 |
| Ex100 | EBL-2 | 1-11 | 2-9 | Ref. | 3.80 | 6.40 | 0.138 | 0.081 | 150 |
| Ex101 | EBL-2 | 1-11 | 2-9 | HBL-1-1 | 3.80 | 6.27 | 0.138 | 0.079 | 204 |
| Ex102 | EBL-2 | 1-11 | 2-9 | HBL-2-1 | 3.80 | 6.54 | 0.138 | 0.076 | 254 |

TABLE 13

| | EBL | D | H | HBL | V | EQE (%) | CIE(x) | CIE(y) | $T_{95}$ (hr) |
|---|---|---|---|---|---|---|---|---|---|
| Ref55 | Ref. | 1-13 | 2-1 | Ref. | 3.90 | 3.11 | 0.138 | 0.002 | 42 |
| Ex103 | Ref. | 1-13 | 2-7 | Ref. | 3.95 | 3.01 | 0.139 | 0.084 | 63 |
| Ex104 | Ref. | 1-13 | 2-7 | HBL-1-1 | 3.85 | 3.14 | 0.137 | 0.083 | 74 |

TABLE 13-continued

| | EBL | D | H | HBL | V | EQE (%) | CIE(x) | CIE(y) | $T_{95}$ (hr) |
|---|---|---|---|---|---|---|---|---|---|
| Ex105 | Bet. | 1-13 | 2-7 | HBL-2-1 | 3.93 | 3.18 | 0.137 | 0.085 | 89 |
| Ex105 | EBL-1 | 1-13 | 2-7 | Ref. | 3.98 | 5.02 | 0.139 | 0.082 | 189 |
| Ex107 | EBL-1 | 1-13 | 2-7 | HBL-1-1 | 3.85 | 6.28 | 0.137 | 0.083 | 223 |
| Ex103 | EBL-1 | 1-13 | 2-7 | HBL-2-1 | 3.93 | 6.36 | 0.137 | 0.085 | 266 |
| Ex109 | EBL-2 | 1-13 | 2-7 | Ref. | 3.92 | 6.50 | 0.138 | 0.081 | 177 |
| Ex110 | EBL-2 | 1-13 | 2-7 | HBL-1-1 | 3.88 | 5.54 | 0.138 | 0.081 | 213 |
| Ex111 | EBL-2 | 1-13 | 2-7 | HBL-2-1 | 3.90 | 6.68 | 0.136 | 0.084 | 250 |

TABLE 14

| | EBL | D | H | HBL | V | EQE (%) | CIE(x) | CIE(y) | $T_{95}$ (hr) |
|---|---|---|---|---|---|---|---|---|---|
| Ref56 | Ref. | 1-13 | 2-3 | Ref. | 3.94 | 3.00 | 0.137 | 0.082 | 41 |
| Ex112 | Ref. | 1-13 | 2-9 | Ref. | 3.82 | 3.09 | 0.139 | 0.083 | 53 |
| Ex113 | Ref. | 1-13 | 2-9 | HBL-1-1 | 3.75 | 8.03 | 0.138 | 0.083 | 63 |
| Ex114 | Ref. | 1-13 | 2-9 | HBL-2-1 | 3.32 | 3.20 | 0.137 | 0.083 | 73 |
| Ex115 | EBL-1 | 1-13 | 2-9 | Ref. | 3.34 | 6.18 | 0.139 | 0.083 | 165 |
| Ex116 | EBL-1 | 1-13 | 2-9 | HBL-1-1 | 3.76 | 6.06 | 0.138 | 0.083 | 189 |
| Ex117 | EBL-1 | 1-13 | 2-9 | HBL-2-1 | 3.84 | 6.40 | 0.137 | 0.083 | 241 |
| Ex118 | EBL-2 | 1-13 | 2-9 | Ref. | 3.85 | 6.39 | 0.137 | 0.083 | 161 |
| Ex119 | EBL-2 | 1-13 | 2-9 | HBL-1-1 | 3.78 | 6.45 | 0.136 | 0.084 | 201 |
| Ex120 | EBL-2 | 1-13 | 2-9 | HBL-2-1 | 3.82 | 6.67 | 0.137 | 0.082 | 222 |

As shown in Tables 7 to 14, in comparison to the OLEDs of Ref49 to Ref56, each of which includes a non-deuterated anthracene derivative, e.g., the compounds 2-1 or 2-3, as a host, the emitting efficiency and the lifespan of the OLEDs of Ex49 to Ex120, each of which includes a deuterated anthracene derivative, e.g., the compounds 2-7 or 2-9, as a host are significantly improved.

In addition, in comparison to the OLEDs of Ex58 to Ex66, Ex76 to Ex84, Ex94 to Ex102 and Ex112 to Ex120, each of which includes the compound 2-9 as a host, the emitting efficiency and the lifespan of the OLEDs of Ex49 to Ex57, Ex67 to Ex75, Ex85 to Ex93 and Ex103 to Ex111, each of which includes the compound 2-7 as a host, are increased. Namely, when the anthracene derivative, in which one naphthalene moiety, i.e., 1-naphthyl, is directly connected to one side of the anthracene moiety and another naphthalene moiety, i.e., 2-naphthyl, is connected to the other side of the anthracene moiety directly or through a linker, being deuterated is included as a host, the emitting efficiency and the lifespan of the OLED are increased.

In addition, when the boron derivative, e.g., the compound 1-6, 1-8, 1-11 or 1-13, having the asymmetric structure is used as a dopant, the emitting efficiency and the lifespan of the OLED are improved.

Moreover, when the boron derivative, e.g., the compound 1-11, 1-12, 1-13 or 1-17, having the asymmetric structure and being deuterated is used as a dopant, the emitting efficiency and the lifespan of the OLED are further improved.

Furthermore, when the compound, e.g., the compound 1-6 or 1-11, in Formula 1-2, in which each of $R_{81}$ and $R_{82}$ is aryl (phenyl) substituted with alkyl (tert-butyl), is used as a dopant, the emitting efficiency and the lifespan of the OLED are further improved.

Further, when the HBL includes the compound in Formula 8 or the compound in Formula 10, the emitting efficiency and the lifespan of the OLED are improved.

Further, when the EBL includes the compound in Formula 6, the emitting efficiency and the lifespan of the OLED are significantly improved.

Further, with the compound 2-7 or 2-9 being the deuterated anthracene derivative and the compound 1-2 being the boron derivative in the EML, the compound in Formula 5 in the EBL and the compound in Formula 7 or 9 in the HBL, the emitting efficiency and the lifespan of the OLED are remarkably improved.

Figure 4:
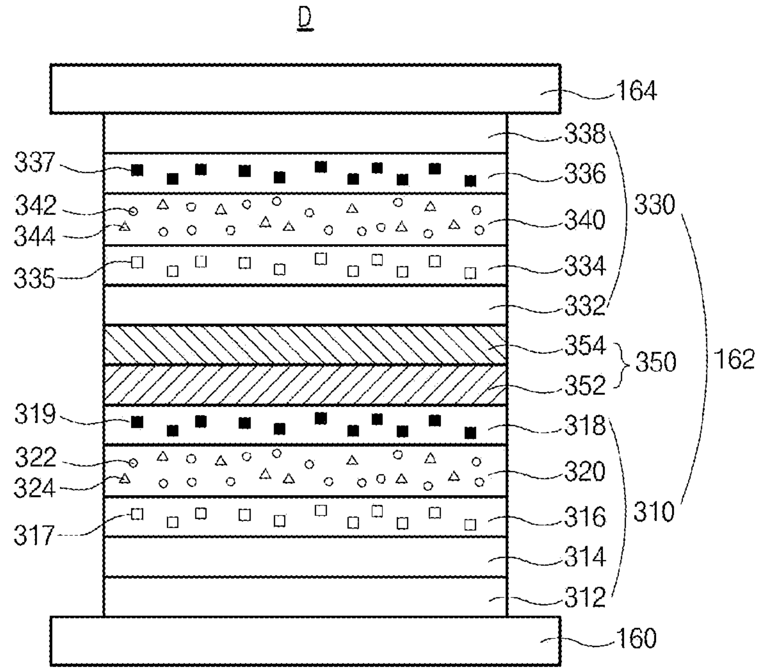
FIG. 4 is a schematic cross-sectional view illustrating an OLED having a tandem structure of two emitting parts according to the first embodiment of the present disclosure.

FIG. 4 is a schematic cross-sectional view illustrating an OLED having a tandem structure of two emitting parts according to the first embodiment of the present disclosure.

As shown in FIG. 4, the OLED D includes the first and second electrodes 160 and 164 facing each other and the organic emitting layer 162 between the first and second electrodes 160 and 164. The organic emitting layer 162 includes a first emitting part 310 including a first EML 320, a first EBL 316 and a first HBL 318, a second emitting part 330 including a second EML 340, a second EBL 334 and a second HBL 336, and a charge generation layer (CGL) 350 between the first and second emitting parts 310 and 330. The organic light emitting display device 100 (of FIG. 2) includes red, green and blue pixels, and the OLED D may be positioned in the blue pixel.

One of the first and second electrodes 160 and 164 is an anode, and the other one of the first and second electrodes 160 and 164 is a cathode. One of the first and second electrodes 160 and 164 is a transparent electrode (or a semi-transparent electrode) electrode, and the other one of the first and second electrodes 160 and 164 is a reflection electrode.

The CGL 350 is positioned between the first and second emitting parts 310 and 330, and the first emitting part 310, the CGL 350 and the second emitting part 330 are sequentially stacked on the first electrode 160. Namely, the first emitting part 310 is positioned between the first electrode 160 and the CGL 350, and the second emitting part 330 is positioned between the second electrode 164 and the CGL 350.

The first emitting part 310 may further include a first HTL 314 between the first electrode 160 and the first EBL 316 and an HIL 312 between the first electrode 160 and the first HTL 314.

The first EML 320 includes a dopant 322 of the boron derivative and a host 324 of the deuterated anthracene derivative and emits blue light. Namely, at least one of hydrogens in the anthracene derivative is substituted with deuterium. The boron derivative is not deuterated, or a part of hydrogens in the boron derivative is substituted with deuterium. The dopant 322 may be represented by Formula 1-1 or 1-2 and may be one of the compounds in Formula 3. The host 324 may be represented by Formula 2 and may be one of the compounds in Formula 4.

In the first EML 320, the host 324 may have a weight % of about 70 to 99.9, and the dopant 322 may have a weight % of about 0.1 to 30. To provide sufficient emitting efficiency, the dopant 322 may have a weight % of about 0.1 to 10, preferably about 1 to 5.

The first EBL 316 may include the compound in Formula 5 as an electron blocking material 317. The first HBL 318 may include at least one of the compound in Formula 7 and the compound in Formula 9 as a hole blocking material 319. For example, the first HBL 318 may include both of the compound in formula 7 and the compound in Formula 9 with the same weight %.

The second emitting part 330 may further include a second HTL 332 between the CGL 350 and the second EBL 334 and an EIL 338 between the second HBL 336 and the second electrode 164.

The second EML 340 includes a dopant 342 of the boron derivative and a host 344 of the deuterated anthracene derivative and emits blue light. Namely, at least one of hydrogens in the anthracene derivative is substituted with deuterium. The boron derivative is not deuterated, or a part of hydrogens in the boron derivative is substituted with deuterium.

In the second EML 340, the host 344 may have a weight % of about 70 to 99.9, and the dopant 342 may have a weight % of about 0.1 to 30. To provide sufficient emitting efficiency, the dopant 342 may have a weight % of about 0.1 to 10, preferably about 1 to 5.

The host 344 of the second EML 340 may be same as or different from the host 324 of the first EML 320, and the dopant 342 of the second EML 340 may be same as or different from the dopant 322 of the first EML 320.

The second EBL 334 may include the compound in Formula 5 as an electron blocking material 335. The second HBL 336 may include at least one of the compound in Formula 7 and the compound in Formula 9 as a hole blocking material 337. For example, the second HBL 336 may include both of the compound in Formula 7 and the compound in Formula 9 with the same weight %.

The CGL 350 is positioned between the first and second emitting parts 310 and 330. Namely, the first and second emitting parts 310 and 330 are connected through the CGL 350. The CGL 350 may be a P-N junction CGL of an N-type CGL 352 and a P-type CGL 354.

The N-type CGL 352 is positioned between the first HBL 318 and the second HTL 332, and the P-type CGL 354 is positioned between the N-type CGL 352 and the second HTL 332.

In the OLED D, each of the first and second EMLs 320 and 340 includes the dopant 322 and 342, which is the boron derivative, and the host 324 and 344, which is the deuterated anthracene derivative. As a result, the OLED D and the organic light emitting display device 100 have advantages in the emitting efficiency and the lifespan.

When the boron derivative as the dopant 322 and 342 has an asymmetric structure as Formula 1-2, the emitting efficiency and the lifespan of the OLED D and the organic light emitting display device 100 are further improved.

In addition, when the boron derivative as the dopant 322 and 342, in which other aromatic ring and hetero-aromatic ring except a benzene ring being combined to boron atom and two nitrogen atoms are partially or wholly deuterated, is included, the emitting efficiency and the lifespan of the OLED D and the organic light emitting display device 100 are further improved.

Moreover, when the anthracene derivative as the host 324 and 344 includes two naphthalene moieties connected to the anthracene moiety and is partially or wholly deuterated, the emitting efficiency and the lifespan of the OLED D and the organic light emitting display device 100 including the anthracene derivative are further improved.

Furthermore, since at least one of the first and second EBLs 316 and 334 includes the compound in Formula 5 as the electron blocking material and each of the first and second HBLs 318 and 336 includes at least one of the compound in Formula 7 and the compound in Formula 9 as the hole blocking material, the lifespan of the OLED D and the organic light emitting display device 100 are further improved.

Further, since the first and second emitting parts 310 and 330 for emitting blue light are stacked, the organic light emitting display device 100 provides an image having high color temperature.

Figure 5:
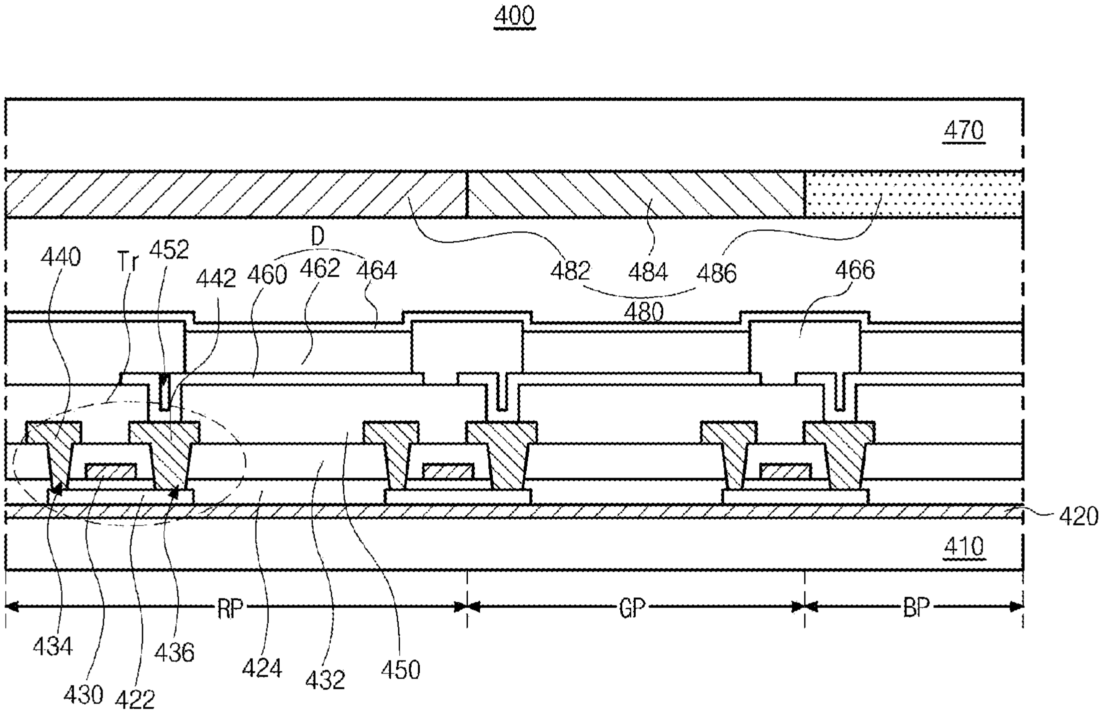
FIG. 5 is a schematic cross-sectional view illustrating an organic light emitting display device according to a second embodiment of the present disclosure.
Figure 6:
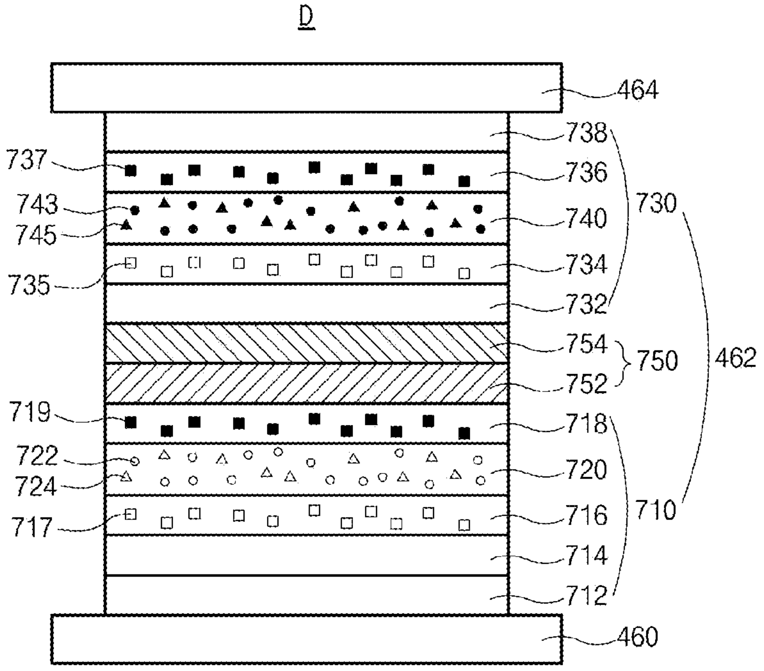
FIG. 6 is a schematic cross-sectional view illustrating an OLED having a tandem structure of two emitting parts according to the second embodiment of the present disclosure.
Figure 7:
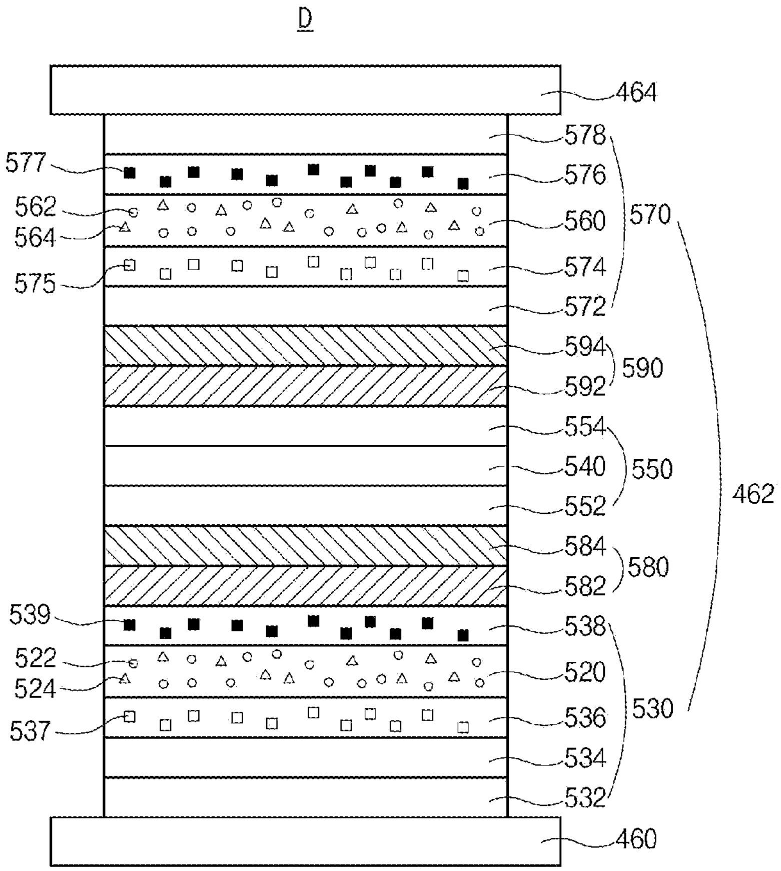
FIG. 7 is a schematic cross-sectional view illustrating an OLED having a tandem structure of three emitting parts according to the second embodiment of the present disclosure.

FIG. 5 is a schematic cross-sectional view illustrating an organic light emitting display device according to a second embodiment of the present disclosure, and FIG. 6 is a schematic cross-sectional view illustrating an OLED having a tandem structure of two emitting parts according to the second embodiment of the present disclosure. FIG. 7 is a schematic cross-sectional view illustrating an OLED having a tandem structure of three emitting parts according to the second embodiment of the present disclosure.

As shown in FIG. 5, the organic light emitting display device 400 includes a first substrate 410, where a red pixel RP, a green pixel GP and a blue pixel BP are defined, a second substrate 470 facing the first substrate 410, an OLED D, which is positioned between the first and second substrates 410 and 470 and providing white emission, and a color filter layer 480 between the OLED D and the second substrate 470.

Each of the first and second substrates 410 and 470 may be a glass substrate or a flexible substrate. For example, the flexible substrate may be one of a polyimide (PI) substrate, polyethersulfone (PES), polyethylenenaphthalate (PEN), polyethylene terephthalate (PET) and polycarbonate (PC).

A buffer layer 420 is formed on the first substrate, and the TFT Tr corresponding to each of the red, green and blue pixels RP, GP and BP is formed on the buffer layer 420. The buffer layer 420 may be omitted.

A semiconductor layer 422 is formed on the buffer layer 420. The semiconductor layer 422 may include an oxide semiconductor material or polycrystalline silicon.

A gate insulating layer 424 is formed on the semiconductor layer 422. The gate insulating layer 424 may be formed of an inorganic insulating material such as silicon oxide or silicon nitride.

A gate electrode 430, which is formed of a conductive material, e.g., metal, is formed on the gate insulating layer 424 to correspond to a center of the semiconductor layer 422.

An interlayer insulating layer 432, which is formed of an insulating material, is formed on the gate electrode 430. The interlayer insulating layer 432 may be formed of an inorganic insulating material, e.g., silicon oxide or silicon nitride, or an organic insulating material, e.g., benzocyclobutene or photo-acryl.

The interlayer insulating layer 432 includes first and second contact holes 434 and 436 exposing both sides of the semiconductor layer 422. The first and second contact holes 434 and 436 are positioned at both sides of the gate electrode 430 to be spaced apart from the gate electrode 430.

A source electrode 440 and a drain electrode 442, which are formed of a conductive material, e.g., metal, are formed on the interlayer insulating layer 432.

The source electrode 440 and the drain electrode 442 are spaced apart from each other with respect to the gate electrode 430 and respectively contact both sides of the semiconductor layer 422 through the first and second contact holes 434 and 436.

The semiconductor layer 422, the gate electrode 430, the source electrode 440 and the drain electrode 442 constitute the TFT Tr. The TFT Tr serves as a driving element. Namely, the TFT Tr may correspond to the driving TFT Td (of FIG. 1).

Although not shown, the gate line and the data line cross each other to define the pixel, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer (or a planarization layer) 450, which includes a drain contact hole 452 exposing the drain electrode 442 of the TFT Tr, is formed to cover the TFT Tr.

A first electrode 460, which is connected to the drain electrode 442 of the TFT Tr through the drain contact hole 452, is separately formed in each pixel and on the passivation layer 450. The first electrode 460 may be an anode and may be formed of a conductive material, e.g., a transparent conductive oxide (TCO), having a relatively high work function. For example, the first electrode 460 may be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 400 is operated in a bottom-emission type, the first electrode 460 may have a single-layered structure of the transparent conductive oxide. When the organic light emitting display device 400 is operated in a top-emission type, a reflection electrode or a reflection layer may be formed under the first electrode 460. For example, the reflection electrode or the reflection layer may be formed of, silver (Ag) or aluminum-palladium-copper (APC) alloy. In this instance, the first electrode 460 may have a triple-layered structure of ITO/Ag/ITO or ITO/APC/ITO.

A bank layer 466 is formed on the passivation layer 450 to cover an edge of the first electrode 460. Namely, the bank layer 466 is positioned at a boundary of the pixel and exposes a center of the first electrode 460 in the pixel. Since the OLED D emits the white light in the red, green and blue pixels RP, GP and BP, the organic emitting layer 462 may be formed as a common layer in the red, green and blue pixels RP, GP and BP without separation. The bank layer 466 may be formed to prevent a current leakage at an edge of the first electrode 460 and may be omitted.

An organic emitting layer 462 is formed on the first electrode 460.

Referring to FIG. 6, the OLED D includes the first and second electrodes 460 and 464 facing each other and the organic emitting layer 462 between the first and second electrodes 460 and 464. The organic emitting layer 462 includes a first emitting part 710 including a first EML 720, a first EBL 716 and a first HBL 718, a second emitting part 730 including a second EML 740, a second EBL 734 and a second HBL 736, and a charge generation layer (CGL) 750 between the first and second emitting parts 710 and 730.

The CGL 750 is positioned between the first and second emitting parts 710 and 730, and the first emitting part 710, the CGL 750 and the second emitting part 730 are sequentially stacked on the first electrode 460. Namely, the first emitting part 710 is positioned between the first electrode 460 and the CGL 750, and the second emitting part 730 is positioned between the second electrode 464 and the CGL 750.

The first emitting part 710 may further include a first HTL 714 between the first electrode 460 and the first EBL 716 and an HIL 712 between the first electrode 460 and the first HTL 714.

The first EML 720 includes a dopant 722 of the boron derivative and a host 724 of the deuterated anthracene derivative and emits blue light. Namely, at least one of hydrogens in the anthracene derivative is substituted with deuterium. The boron derivative is not deuterated, or a part of hydrogens in the boron derivative is substituted with deuterium. The dopant 722 may be represented by Formula 1-1 or 1-2 and may be one of the compounds in Formula 3. The host 724 may be represented by Formula 2 and may be one of the compounds in Formula 4.

In the first EML 720, the host 724 may have a weight % of about 70 to 99.9, and the dopant 722 may have a weight % of about 0.1 to 30. To provide sufficient emitting efficiency, the dopant 722 may have a weight % of about 0.1 to 10, preferably about 1 to 5.

The first EBL 716 may include the compound in Formula 5 as an electron blocking material 717. The first HBL 718 may include at least one of the compound in Formula 7 and the compound in Formula 9 as a hole blocking material 719. For example, the first HBL 718 may include both of the compound in formula 7 and the compound in Formula 9 with the same weight %.

The second emitting part 730 may further include a second HTL 732 between the CGL 750 and the second EBL 734 and an EIL 738 between the second HBL 736 and the second electrode 464.

The second EML 740 may be a yellow-green EML. For example, the second EML 740 may include a yellow-green dopant 743 and a host 745. The yellow-green dopant 743 may be one of a fluorescent compound, a phosphorescent compound and a delayed fluorescent compound.

In the second EML 740, the host 745 may have a weight % of about 70 to 99.9, and the yellow-green dopant 743 may have a weight % of about 0.1 to 30. To provide sufficient emitting efficiency, the yellow-green dopant 743 may have a weight % of about 0.1 to 10, preferably about 1 to 5.

The second EBL 734 may include the compound in Formula 5 as an electron blocking material 735. The second HBL 736 may include at least one of the compound in Formula 7 and the compound in Formula 9 as a hole blocking material 737. For example, the second HBL 736 may include both of the compound in formula 7 and the compound in Formula 9 with the same weight %.

The CGL 750 is positioned between the first and second emitting parts 710 and 730. Namely, the first and second emitting parts 710 and 730 are connected through the CGL 750. The CGL 750 may be a P-N junction CGL of an N-type CGL 752 and a P-type CGL 754.

The N-type CGL 752 is positioned between the first HBL 718 and the second HTL 732, and the P-type CGL 754 is positioned between the N-type CGL 752 and the second HTL 732.

In FIG. 6, the first EML 720, which is positioned between the first electrode 460 and the CGL 750, includes the host 722 of the anthracene derivative and the dopant 724 of the boron derivative, and the second EML 740, which is positioned between the second electrode 464 and the CGL 750, is the yellow-green EML. Alternatively, the first EML 720, which is positioned between the first electrode 460 and the CGL 750, may be the yellow-green EML, and the second EML 740, which is positioned between the second electrode 464 and the CGL 750, may include the host of the anthracene derivative and the dopant of the boron derivative to be a blue EML.

In the OLED D, the first EML 720 includes the dopant 722, each of which is the boron derivative, and the host 724, each of which is the deuterated anthracene derivative. As a result, the OLED D and the organic light emitting display device 400 have advantages in the emitting efficiency and the lifespan.

When the boron derivative as the dopant 722 has an asymmetric structure as. Formula 1-2, the emitting efficiency and the lifespan of the OLED D and the organic light emitting display device 400 are further improved.

In addition, when the boron derivative as the dopant 722, in which other aromatic ring and hetero-aromatic ring except a benzene ring being combined to boron atom and two nitrogen atoms are partially or wholly deuterated, is included, the emitting efficiency and the lifespan of the OLED D and the organic light emitting display device 400 are further improved.

Moreover, when the anthracene derivative as the host 724 includes two naphthalene moieties connected to the anthracene moiety and is partially or wholly deuterated, the emitting efficiency and the lifespan of the OLED D and the organic light emitting display device 400 including the anthracene derivative are further improved.

Furthermore, since at least one of the first and second EBLs 716 and 734 includes the compound in Formula 5 as the electron blocking material and each of the first and second HBLs 718 and 736 includes at least one of the compound in Formula 7 and the compound in Formula 9 as the hole blocking material, the lifespan of the OLED D and the organic light emitting display device 400 are further improved.

Further, the OLED D including the first emitting part 710 and the second emitting part 730, which provides a yellow-green emission, emits a white light.

Referring to FIG. 7, the organic emitting layer 462 includes a first emitting part 530 including a first EML 520, a first EBL 536 and a first HBL 538, a second emitting part 550 including a second EML 540, a third emitting part 570 including a third EML 560, a second EBL 574 and a second HBL 576, a first CGL 580 between the first and second emitting parts 530 and 550, and a second CGL 590 between the second and third emitting parts 550 and 570.

The first CGL 580 is positioned between the first and second emitting parts 530 and 550, and the second CGL 590 is positioned between the second and third emitting parts 550 and 570. Namely, the first emitting part 530, the first CGL 580, the second emitting part 550, the second CGL 590 and the third emitting part 570 are sequentially stacked on the first electrode 460. In other words, the first emitting part 530 is positioned between the first electrode 460 and the first CGL 580, the second emitting part 550 is positioned between the first and second CGLs 580 and 590, and the third emitting part 570 is positioned between the second electrode 464 and the second CGL 590.

The first emitting part 530 may include at least one of a first HTL 534 between the first electrode 460 and the first EBL 536 and an HIL 532 between the first electrode 460 and the first HTL 534. For example, the HIL 532, the first HTL 534 and the first EBL 536 may be sequentially stacked between the first electrode 460 and the first EML 520, and the first HBL 538 may be positioned between the first EML 520 and the first CGL 580.

The first EML 520 includes a dopant 522 of the boron derivative and a host 524 of the deuterated anthracene derivative and emits blue light. Namely, at least one of hydrogens in the anthracene derivative is substituted with deuterium. The boron derivative is not deuterated, or a part of hydrogens in the boron derivative is substituted with deuterium. The dopant 522 may be represented by Formula 1-1 or 1-2 and may be one of the compounds in Formula 3. The host 524 may be represented by Formula 2 and may be one of the compounds in Formula 4.

In the first EML 520, the host 524 may have a weight % of about 70 to 99.9, and the dopant 522 may have a weight % of about 0.1 to 30. To provide sufficient emitting efficiency, the dopant 522 may have a weight % of about 0.1 to 10, preferably about 1 to 5.

The first EBL 536 may include the compound in Formula 5 as an electron blocking material 537. The first HBL 538 may include at least one of the compound in Formula 7 and the compound in Formula 9 as a hole blocking material 539. For example, the first HBL 538 may include both of the compound in Formula 7 and the compound in Formula 9 with the same weight %.

The second emitting part 550 may further include a second HTL 552 and an electron transporting layer (ETL) 554. The second HTL 552 is positioned between the first CGL 580 and the second EML 540, and the ETL 554 is positioned between the second EML 540 and the second CGL 590.

The second EML 540 may be a yellow-green EML. For example, the second EML 540 may include a host and a yellow-green dopant.

Alternatively, the second EML 540 may include a host, a red dopant and a green dopant. In this instance, the second EML 540 may have a single-layered structure, or may have a double-layered structure of a lower layer including the host and the red dopant (or the green dopant) and an upper layer including the host and the green dopant (or the red dopant).

The second EML 540 may have a triple-layered structure of a first layer, which includes a host and a red dopant, a second layer, which includes a host and a yellow-green dopant, and a third layer, which includes a host and a green dopant.

The third emitting part 570 may further include at least one of a third HTL 572 under the second EBL 574 and an EIL 578 over the second HBL 576.

The third EML 560 includes a dopant 562 of the boron derivative and a host 564 of the deuterated anthracene derivative and emits blue light. Namely, at least one of hydrogens in the anthracene derivative is substituted with deuterium. The boron derivative is not deuterated, or a part of hydrogens in the boron derivative is substituted with deuterium. The dopant 562 may be represented by Formula 1-1 or 1-2 and may be one of the compounds in Formula 3. The host 564 may be represented by Formula 2 and may be one of the compounds in Formula 4.

In the third EML 560, the host 564 may have a weight % of about 70 to 99.9, and the dopant 562 may have a weight % of about 0.1 to 30. To provide sufficient emitting efficiency, the dopant 562 may have a weight % of about 0.1 to 10, preferably about 1 to 5.

The host 564 of the third EML 560 may be same as or different from the host 524 of the first EML 520, and the dopant 562 of the third EML 560 may be same as or different from the dopant 522 of the first EML 520.

The second EBL 574 may include the compound in Formula 5 as an electron blocking material 575. The second HBL 576 may include at least one of the compound in Formula 7 and the compound in Formula 9 as a hole blocking material 577. For example, the second HBL 576 may include both of the compound in formula 7 and the compound in Formula 9 with the same weight %.

The first CGL 580 is positioned between the first emitting part 530 and the second emitting part 550, and the second CGL 590 is positioned between the second emitting part 550 and the third emitting part 570. Namely, the first and second emitting parts 530 and 550 are connected through the first CGL 580, and the second and third emitting parts 550 and 570 are connected through the second CGL 590. The first CGL 580 may be a P-N junction CGL of a first N-type CGL 582 and a first P-type CGL 584, and the second CGL 590 may be a P-N junction CGL of a second N-type CGL 592 and a second P-type CGL 594.

In the first CGL 580, the first N-type CGL 582 is positioned between the first HBL 538 and the second HTL 552, and the first P-type CGL 584 is positioned between the first N-type CGL 582 and the second HTL 552.

In the second CGL 590, the second N-type CGL 592 is positioned between the ETL 554 and the third HTL 572, and the second P-type CGL 594 is positioned between the second N-type CGL 592 and the third HTL 572.

In the OLED D, each of the first and third EMLs 520 and 560 includes the dopant 522 and 562, each of which is the boron derivative and the host 524 and 564, each of which is the deuterated anthracene derivative. As a result, the OLED D and the organic light emitting display device 400 have advantages in the emitting efficiency and the lifespan.

When the boron derivative as the dopant 522 and 562 has an asymmetric structure as Formula 1-2, the emitting efficiency and the lifespan of the OLED D and the organic light emitting display device 400 are further improved.

In addition, when the boron derivative as the dopant 522 and 562, in which other aromatic ring and hetero-aromatic ring except a benzene ring being combined to boron atom and two nitrogen atoms are partially or wholly deuterated, is included, the emitting efficiency and the lifespan of the OLED D and the organic light emitting display device 400 are further improved.

Moreover, when the anthracene derivative as the host 524 and 564 includes two naphthalene moieties connected to the anthracene moiety and is partially or wholly deuterated, the emitting efficiency and the lifespan of the OLED D and the organic light emitting display device 400 including the anthracene derivative are further improved.

Furthermore, since at least one of the first and second EBLs 536 and 574 includes the compound in Formula 5 as the electron blocking material and each of the first and second HBLs 538 and 576 includes at least one of the compound in Formula 7 and the compound in Formula 9 as the hole blocking material, the lifespan of the OLED D and the organic light emitting display device 400 are further improved.

Further, the OLED D including the first and third emitting parts 530 and 570 with the second emitting part 550, which emits yellow-green light or red/green light, can emit white light.

In FIG. 7, the OLED D has a triple-stack structure of the first, second and third emitting parts 530, 550, and 570. Alternatively, the OLED D may further include additional emitting part and CGL.

Referring to FIG. 5 again, a second electrode 464 is formed over the substrate 410 where the organic emitting layer 462 is formed.

In the organic light emitting display device 400, since the light emitted from the organic emitting layer 462 is incident to the color filter layer 480 through the second electrode 464, the second electrode 464 has a thin profile for transmitting the light.

The first electrode 460, the organic emitting layer 462 and the second electrode 464 constitute the OLED D.

The color filter layer 480 is positioned over the OLED D and includes a red color filter 482, a green color filter 484 and a blue color filter 486 respectively corresponding to the red, green and blue pixels RP, GP and BP. The red color filter 482 may include at least one of red dye and red pigment, the green color filter 484 may include at least one of green dye and green pigment, and the blue color filter 486 may include at least one of blue dye and blue pigment.

Although not shown, the color filter layer 480 may be attached to the OLED D by using an adhesive layer. Alternatively, the color filter layer 480 may be formed directly on the OLED D.

An encapsulation film (not shown) may be formed to prevent penetration of moisture into the OLED D. For example, the encapsulation film may include a first inorganic insulating layer, an organic insulating layer and a second inorganic insulating layer sequentially stacked, but it is not limited thereto. The encapsulation film may be omitted.

A polarization plate (not shown) for reducing an ambient light reflection may be disposed over the top-emission type OLED D. For example, the polarization plate may be a circular polarization plate.

In the OLED of FIG. 5, the first and second electrodes 460 and 464 are a reflection electrode and a transparent (or semi-transparent) electrode, respectively, and the color filter layer 480 is disposed over the OLED D. Alternatively, when the first and second electrodes 460 and 464 are a transparent (or semi-transparent) electrode and a reflection electrode, respectively, the color filter layer 480 may be disposed between the OLED D and the first substrate 410.

A color conversion layer (not shown) may be formed between the OLED D and the color filter layer 480. The color conversion layer may include a red color conversion layer, a green color conversion layer and a blue color conversion layer respectively corresponding to the red, green and blue pixels RP, GP and BP. The white light from the OLED D is converted into the red light, the green light and the blue light by the red, green and blue color conversion layer, respectively. For example, the color conversion layer may include a quantum dot. Accordingly, the color purity of the organic light emitting display device 400 may be further improved.

The color conversion layer may be included instead of the color filter layer 480.

As described above, in the organic light emitting display device 400, the OLED D in the red, green and blue pixels RP, GP and BP emits the white light, and the white light from the organic light emitting diode D passes through the red color filter 482, the green color filter 484 and the blue color filter 486. As a result, the red light, the green light and the blue light are provided from the red pixel RP, the green pixel GP and the blue pixel BP, respectively.

In FIGS. 5 to 7, the OLED D emitting the white light is used for a display device. Alternatively, the OLED D may be formed on an entire surface of a substrate without at least one of the driving element and the color filter layer to be used for a lightening device. The display device and the lightening device each including the OLED D of the present disclosure may be referred to as an organic light emitting device.

Figure 8:
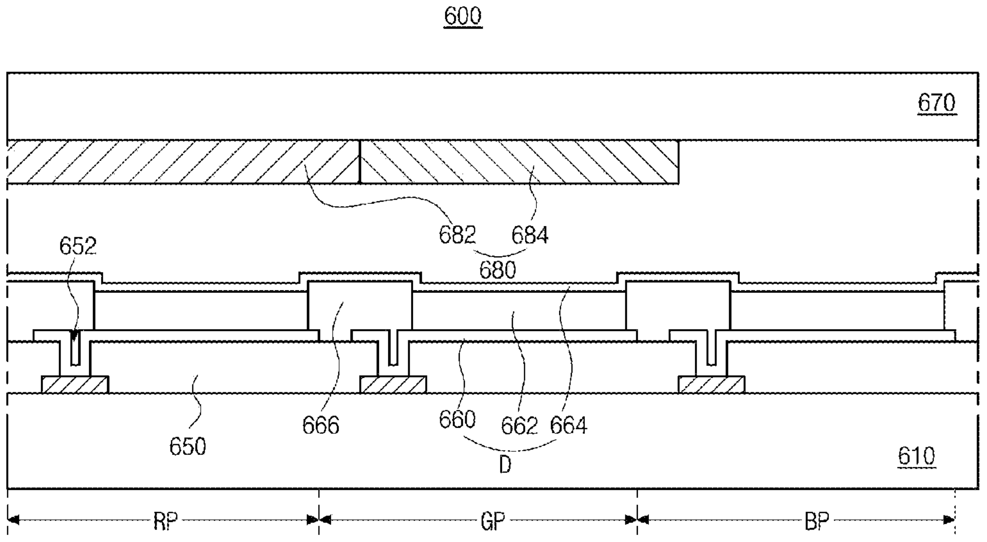
FIG. 8 is a schematic cross-sectional view illustrating an organic light emitting display device according to a third embodiment of the present disclosure.

FIG. 8 is a schematic cross-sectional view illustrating an organic light emitting display device according to a third embodiment of the present disclosure.

As shown in FIG. 8, the organic light emitting display device 600 includes a first substrate 610, where a red pixel RP, a green pixel GP and a blue pixel BP are defined, a second substrate 670 facing the first substrate 610, an OLED D, which is positioned between the first and second substrates 610 and 670 and providing white emission, and a color conversion layer 680 between the OLED D and the second substrate 670.

Although not shown, a color filter may be formed between the second substrate 670 and each color conversion layer 680.

Each of the first and second substrates 610 and 670 may be a glass substrate or a flexible substrate. For example, the flexible substrate may be one of a polyimide (PI) substrate, polyethersulfone (PES), polyethylenenaphthalate (PEN), polyethylene terephthalate (PET) and polycarbonate (PC).

A TFT Tr, which corresponding to each of the red, green and blue pixels RP, GP and BP, is formed on the first substrate 610, and a passivation layer 650, which has a drain contact hole 652 exposing an electrode, e.g., a drain electrode, of the TFT Tr is formed to cover the TFT Tr.

The OLED D including a first electrode 660, an organic emitting layer 662 and a second electrode 664 is formed on the passivation layer 650. In this instance, the first electrode 660 may be connected to the drain electrode of the TFT Tr through the drain contact hole 652.

A bank layer 666 is formed on the passivation layer 650 to cover an edge of the first electrode 660. Namely, the bank layer 666 is positioned at a boundary of the pixel and exposes a center of the first electrode 660 in the pixel. Since the OLED D emits the blue light in the red, green and blue pixels RP, GP and BP, the organic emitting layer 662 may be formed as a common layer in the red, green and blue pixels RP, GP and BP without separation. The bank layer 666 may be formed to prevent a current leakage at an edge of the first electrode 660 and may be omitted.

The OLED D emits a blue light and may have a structure shown in FIG. 3 or FIG. 4. Namely, the OLED D is formed in each of the red, green and blue pixels RP, GP and BP and provides the blue light.

The color conversion layer 680 includes a first color conversion layer 682 corresponding to the red pixel RP and a second color conversion layer 684 corresponding to the green pixel GP. For example, the color conversion layer 680 may include an inorganic color conversion material such as a quantum dot. The color conversion layer 680 is not presented in the blue pixel BP such that the OLED D in the blue pixel may directly face the second electrode 670.

The blue light from the OLED D is converted into the red light by the first color conversion layer 682 in the red pixel RP, and the blue light from the OLED D is converted into the green light by the second color conversion layer 684 in the green pixel GP.

Accordingly, the organic light emitting display device 600 can display a full-color image.

On the other hand, when the light from the OLED D passes through the first substrate 610, the color conversion layer 680 is disposed between the OLED D and the first substrate 610.

It will be apparent to those skilled in the art that various modifications and variations can be made in the embodiments of the present disclosure without departing from the spirit or scope of the present disclosure. Thus, it is intended that the modifications and variations cover this disclosure provided they come within the scope of the appended claims and their equivalents.

What is claimed is:

1. An organic light emitting device, comprising:

a substrate; and an organic light emitting diode positioned on the substrate, the organic light emitting diode including:

a first electrode;

a second electrode facing the first electrode;

a first emitting material layer including a first dopant of a boron derivative and a first host of an anthracene derivative and positioned between the first electrode and the second electrode;

a first electron blocking layer including an electron blocking material and positioned between the first electrode and the first emitting material layer; and a first hole blocking layer including a hole blocking material and positioned between the second electrode and the first emitting material layer, wherein the first dopant is represented by Formula 4:

[Formula 4]

1-11

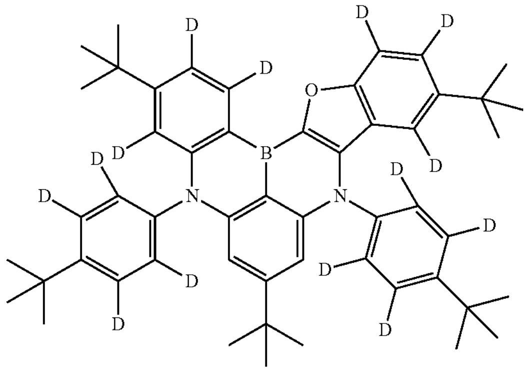

-continued
1-12
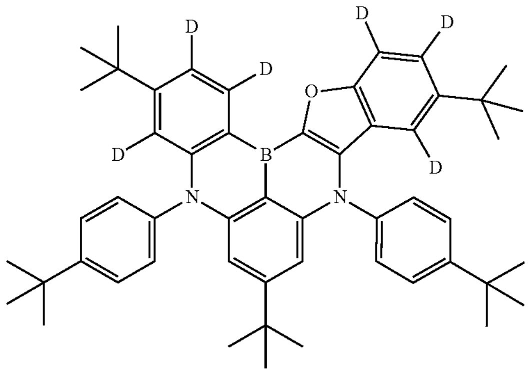
1-13
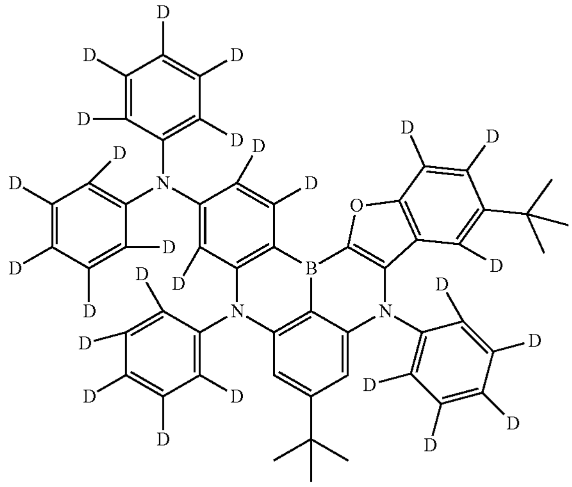
1-17
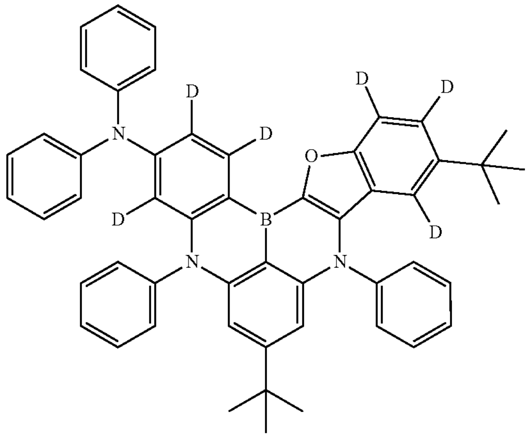
,
wherein the first host is one of compound in Formula 5:
[Formula 5]
2-7
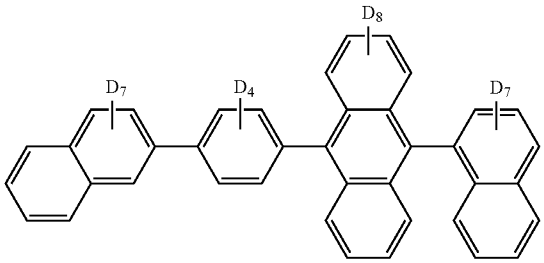
2-8
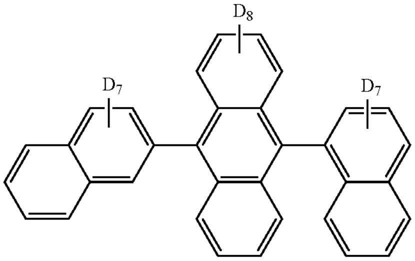
2-9
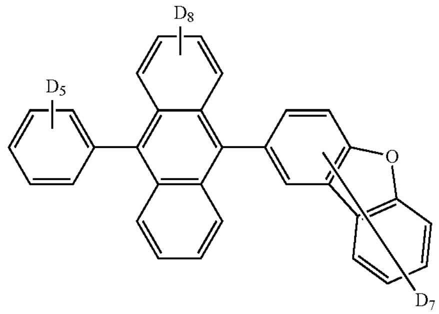
2-10
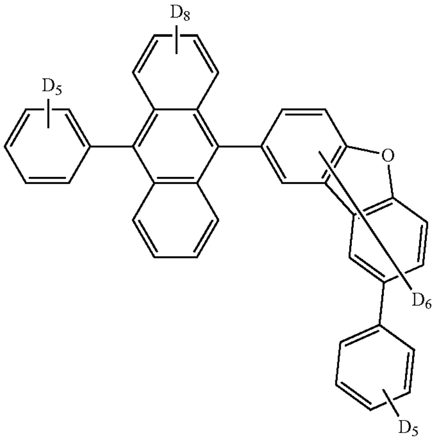

-continued 2-11

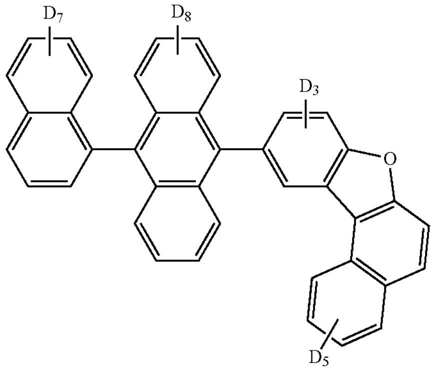

2-12

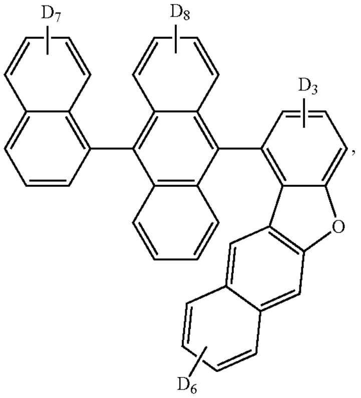

wherein the electron blocking material is represented by Formula 3:

[Formula 3]

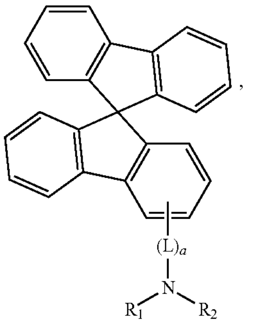

wherein in Formula 3, L is arylene group, and a is 0 or 1, and wherein each of $R_1$ and $R_2$ is independently selected from the group consisting of unsubstituted or substituted $C_6$ to $C_{30}$ aryl group and unsubstituted or substituted $C_5$ to $C_{30}$ heteroaryl group.

2. The organic light emitting device of claim 1, wherein the electron blocking material is one of compounds in Formula 6:

[Formula 6]

EBL-1

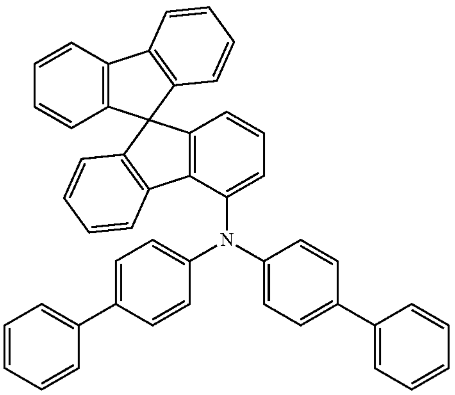

EBL-2

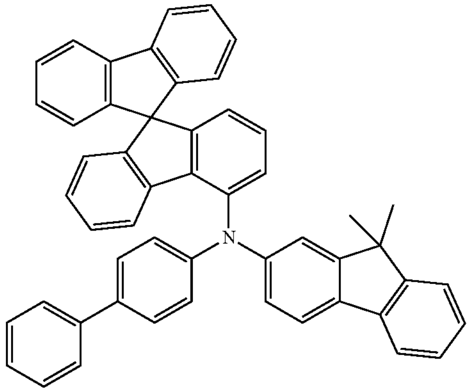

EBL-3

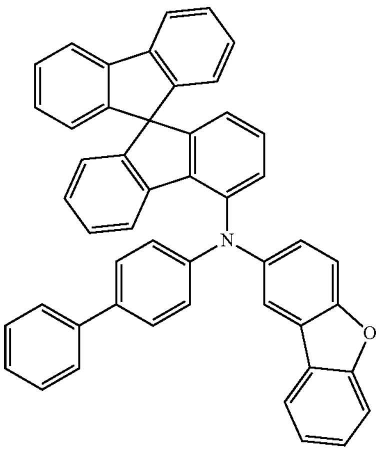

-continued
EBL-4
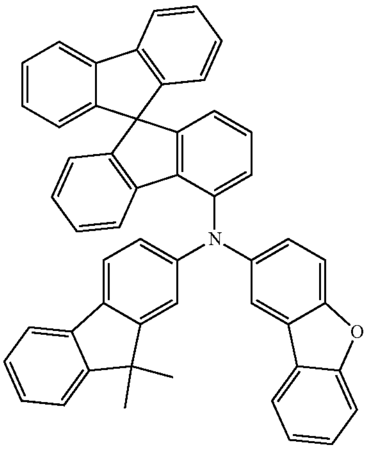
EBL-5
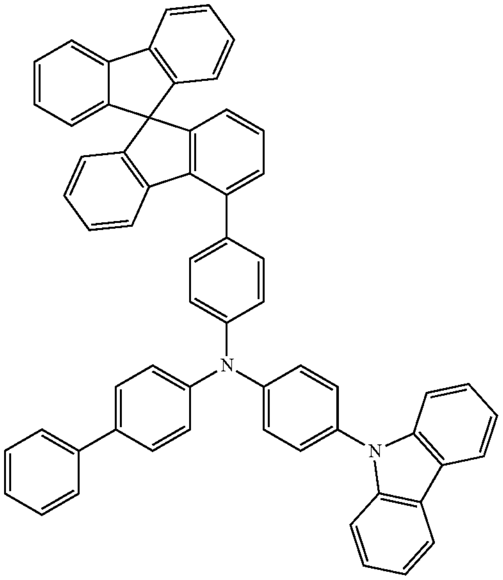
EBL-6
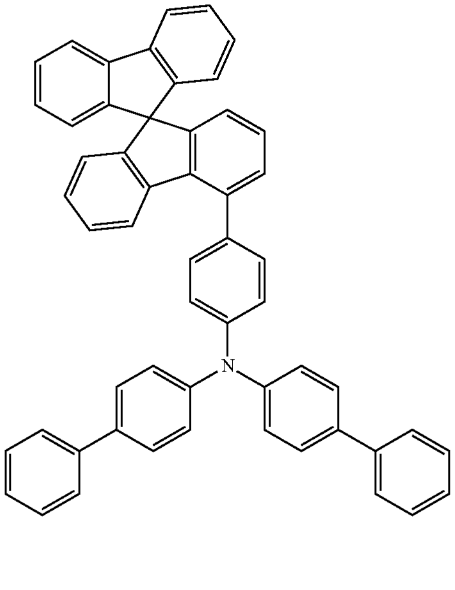
-continued
EBL-7
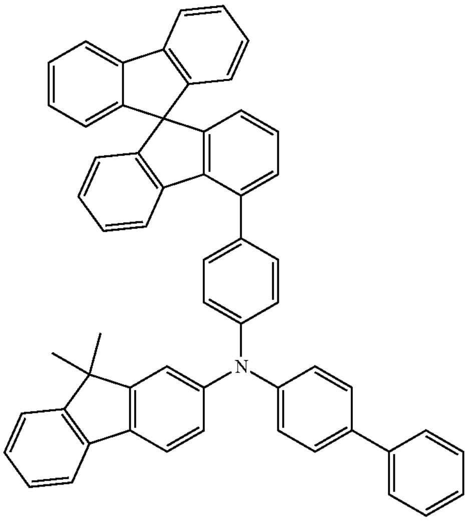
EBL-8
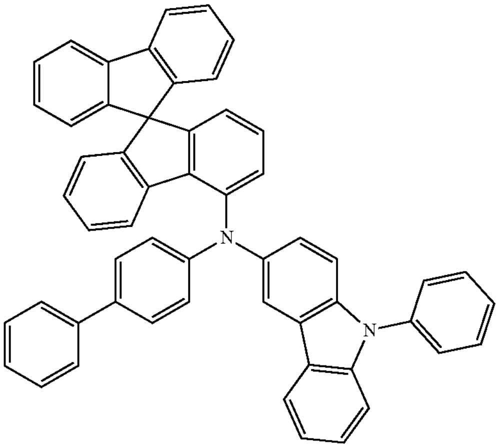
EBL-9
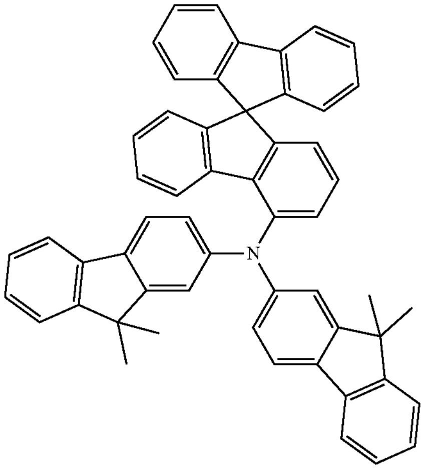

-continued

EBL-10

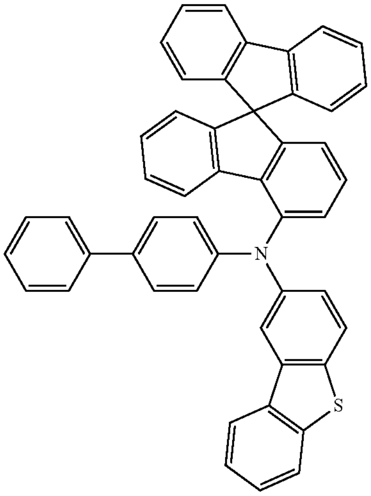

EBL-11

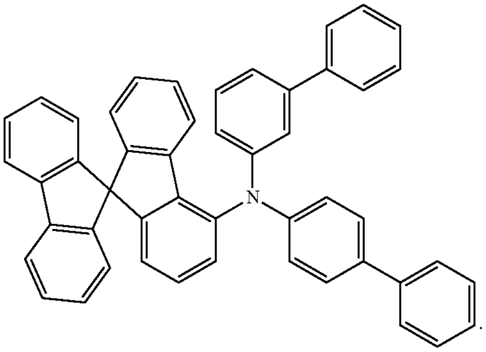

3. The organic light emitting device of claim 1, wherein the hole blocking material is represented by Formula 7:

[Formula 7]

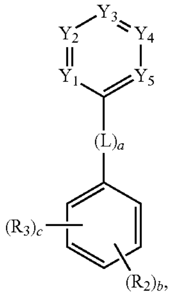

wherein each of $Y_1$ to $Y_5$ is independently $CR_1$ or N, and one to three of $Y_1$ to $Y_5$ is N, wherein $R_1$ is independently hydrogen or $C_6$ to $C_{30}$ aryl group, wherein L is $C_6$ to $C_{30}$ arylene group, and $R_2$ is $C_6$ to $C_{50}$ aryl group or $C_5$ to $C_{50}$ hetero aryl group, wherein $R_3$ is $C_1$ to $C_{10}$ alkyl group, or adjacent two of $R_3$ form a fused ring, and wherein a is 0 or 1, b is 1 or 2, and c is an integer of 0 to 4.

4. The organic light emitting device of claim 3, wherein the hole blocking material is one of compounds in Formula 8:

[Formula 8]

E1

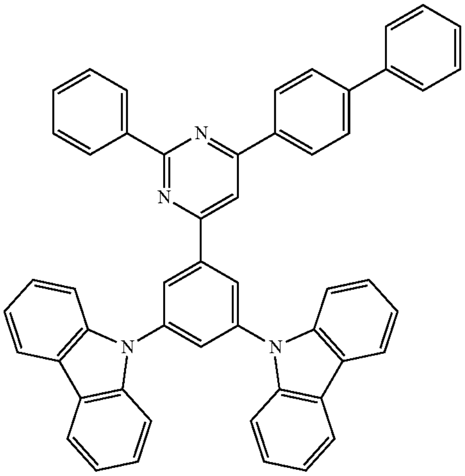

E2

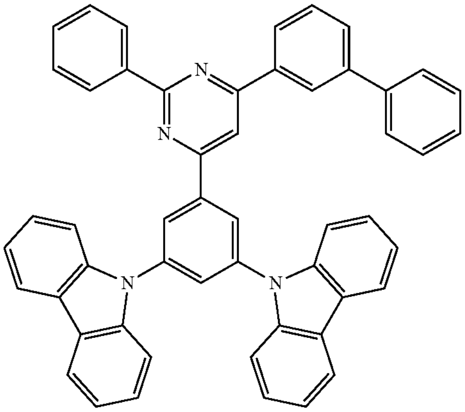

E3

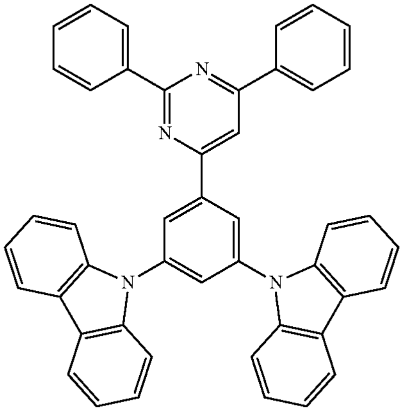

-continued
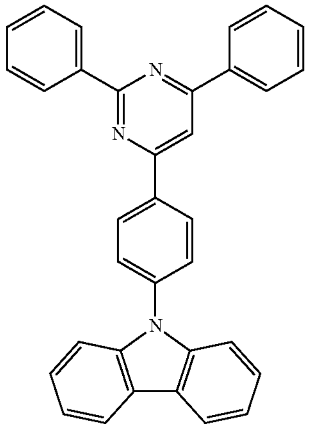
E4
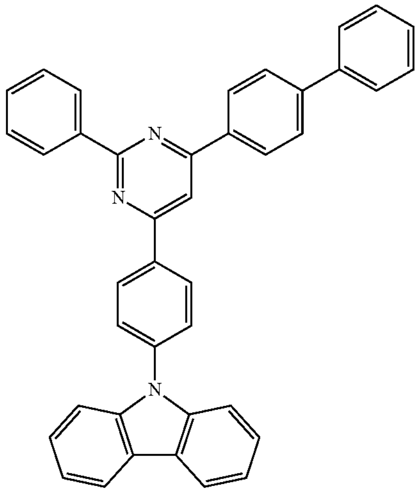
E5
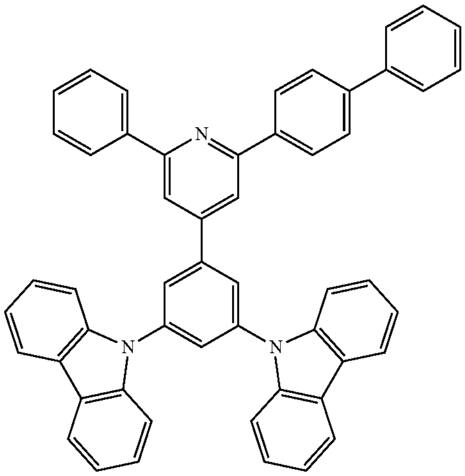
E6
-continued
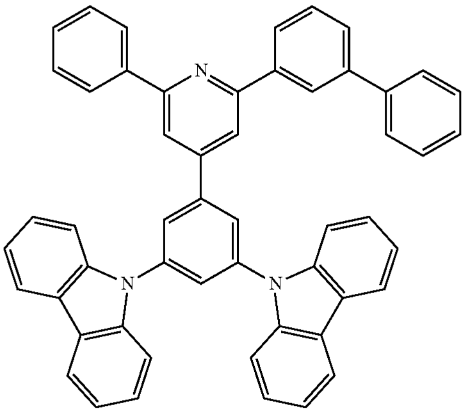
E7
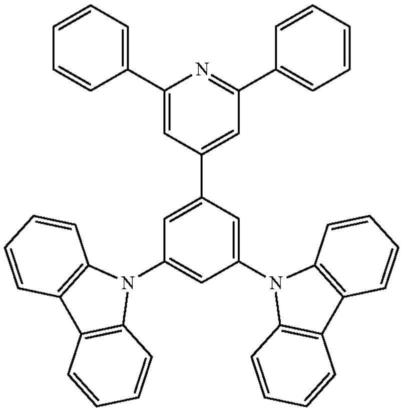
E8
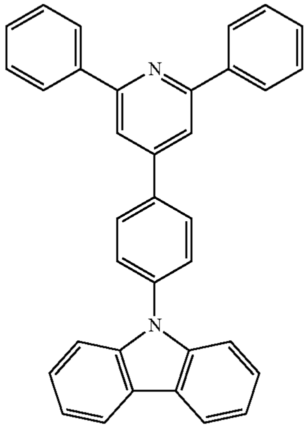
E9

-continued
E10
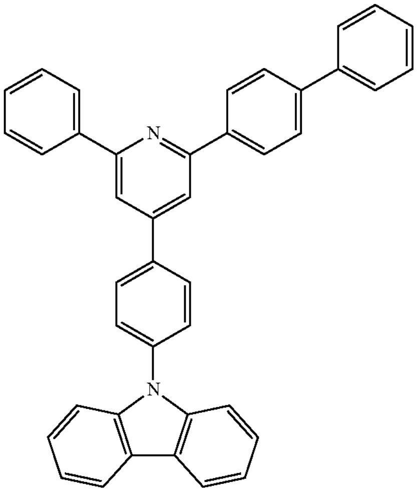
E11
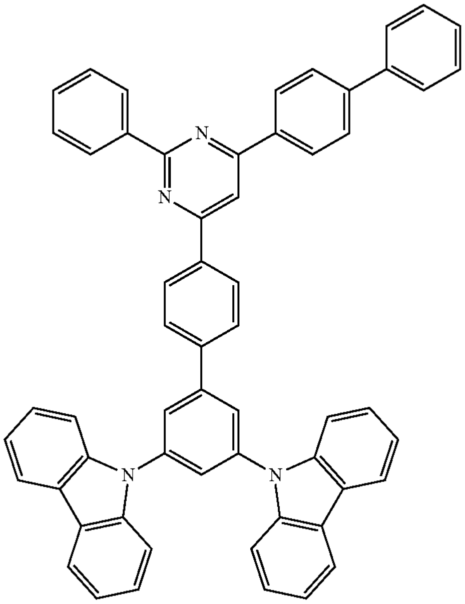
E12
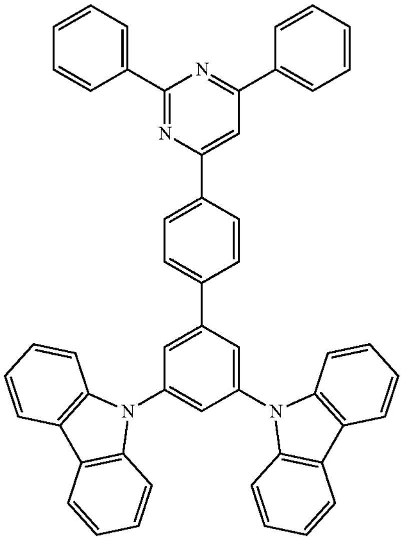
-continued
E13
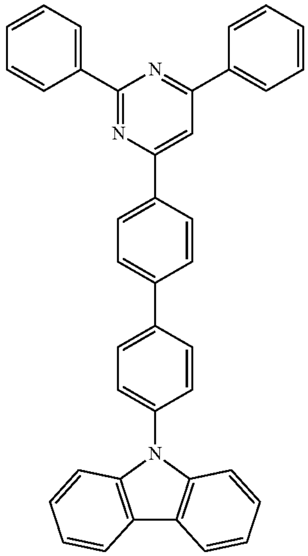
E14
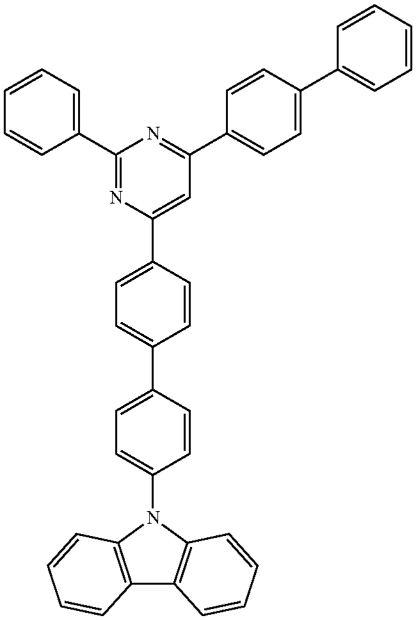
E15
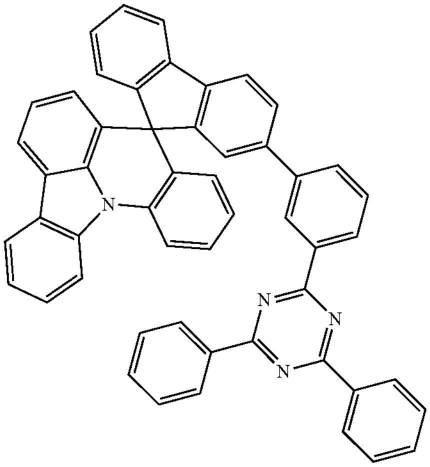

-continued
E16
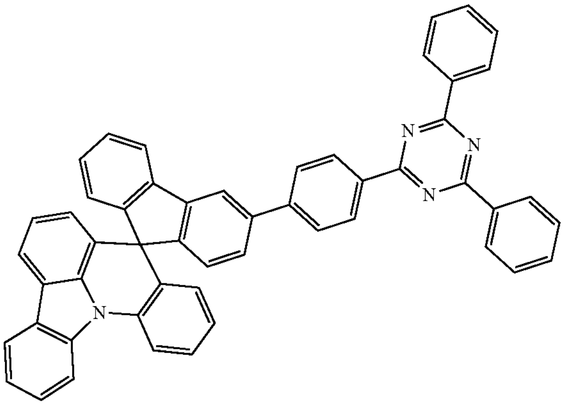
E17
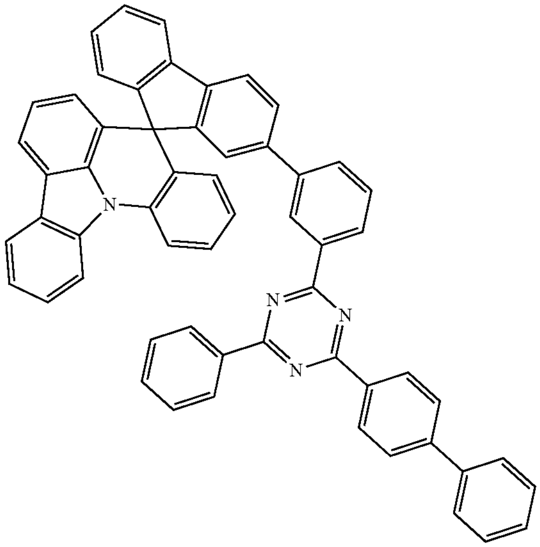
E18
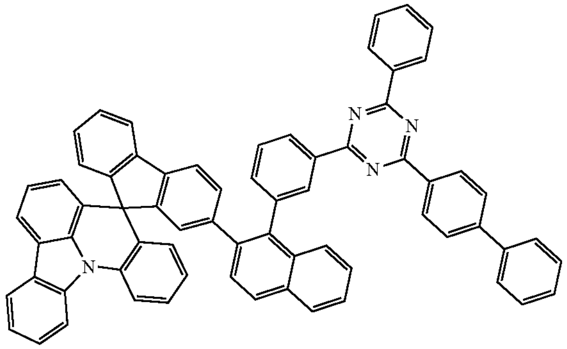
-continued
E19
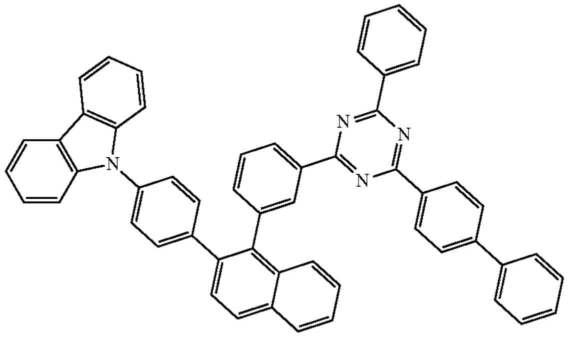
E20
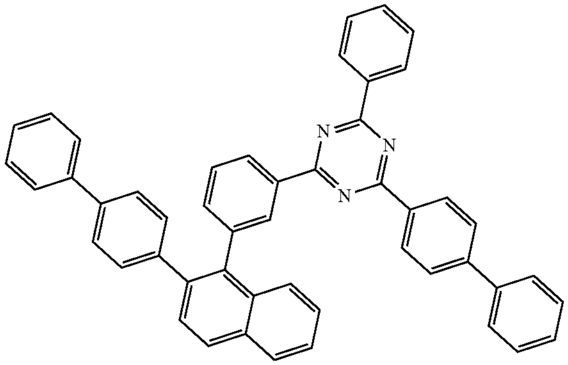
E21
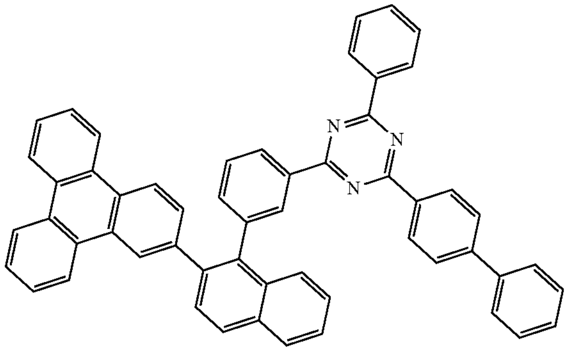
E22
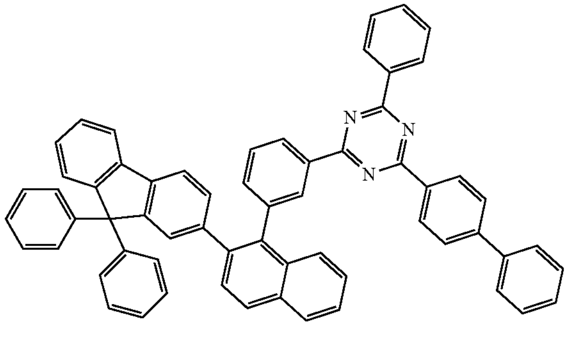

-continued

E23

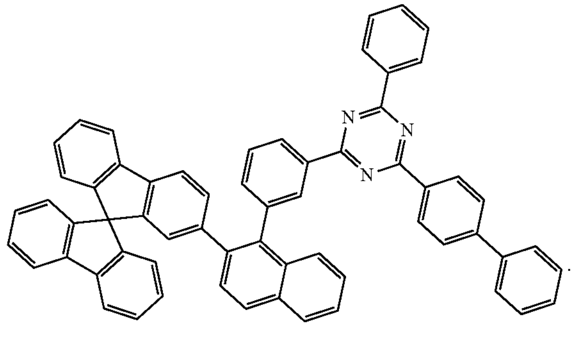

5. The organic light emitting device of claim 1, wherein the hole blocking material is represented by Formula 9:

[Formula 9]

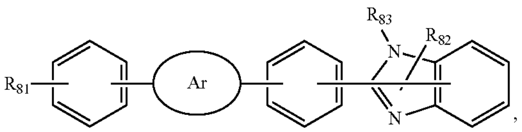

wherein Ar is $C_{10}$ to $C_{30}$ arylene group, and wherein $R_{81}$ is $C_6$ to $C_{30}$ aryl group unsubstituted or substituted with $C_1$ to $C_{10}$ alkyl group or $C_5$ to $C_{30}$ heteroaryl group unsubstituted or substituted with $C_1$ to $C_{10}$ alkyl group, and wherein each of $R_{82}$ and $R_{83}$ is independently hydrogen, $C_1$ to $C_{10}$ alkyl group or $C_6$ to $C_{30}$ aryl group.

6. The organic light emitting device of claim 5, wherein the hole blocking material is one of compounds in Formula 9:

[Formula 9]

F1

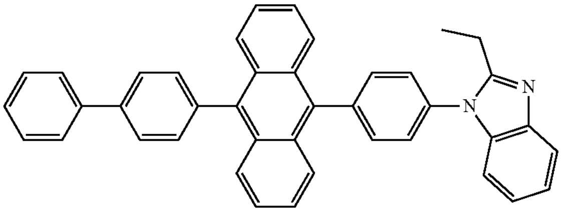

F2

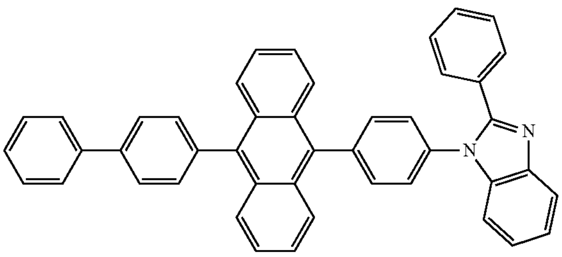

-continued

F3

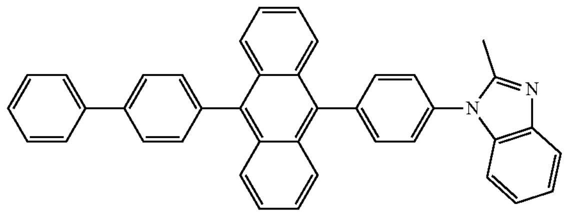

F4

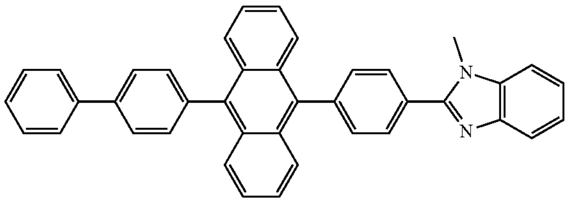

F5

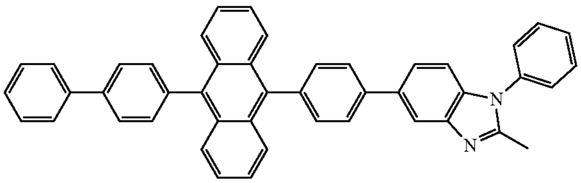

F6

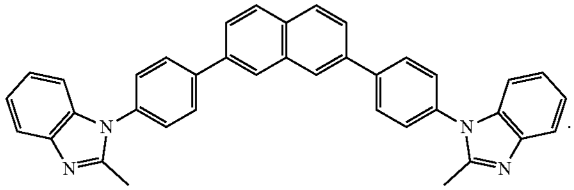

7. The organic light emitting device of claim 1, wherein the organic light emitting diode further includes:

a second emitting material layer including a second dopant of a boron derivative and a second host of an anthracene derivative and positioned between the first emitting material layer and the second electrode; and a first charge generation layer between the first emitting material layer and the second emitting material layer.

8. The organic light emitting device of claim 7, wherein the second dopant is represented by Formula 1, and the second host is represented by Formula 2.

9. The organic light emitting device of claim 8, wherein a red pixel, a green pixel and a blue pixel are defined on the substrate, and the organic light emitting diode corresponds to each of the red pixel, the green pixel, and the blue pixel, and wherein the organic light emitting device further includes:

a color conversion layer disposed between the substrate and the organic light emitting diode or on the organic light emitting diode and corresponding to the red pixel and the green pixel.

10. The organic light emitting device of claim 7, wherein the organic light emitting diode further includes:

a third emitting material layer emitting a yellow-green light and positioned between the first charge generation layer and the second emitting material layer; and a second charge generation layer between the second emitting material layer and the third emitting material layer.

11. The organic light emitting device of claim 10, wherein a red pixel, a green pixel and a blue pixel are defined on the substrate, and the organic light emitting diode corresponds to each of the red pixel, the green pixel, and the blue pixel, and wherein the organic light emitting device further includes:

a color filter layer disposed between the substrate and the organic light emitting diode or on the organic light emitting diode and corresponding to the red pixel, the green pixel, and the blue pixel.

12. The organic light emitting device of claim 7, wherein the organic light emitting diode further includes:

a third emitting material layer emitting a red light and a green light and positioned between the first charge generation layer and the second emitting material layer; and a second charge generation layer between the second emitting material layer and the third emitting material layer.

13. The organic light emitting device of claim 7, wherein the organic light emitting diode further includes:

a third emitting material layer including a first layer and a second layer and positioned between the first charge generation layer and the second emitting material layer; and a second charge generation layer between the second emitting material layer and the third emitting material layer, wherein the first layer emits a red light, and the second layer emits a yellow-green light.

14. The organic light emitting device of claim 13, wherein the third emitting material layer further includes a third layer emitting a green light.

15. The organic light emitting device of claim 1, wherein the organic light emitting diode further includes:

a second emitting material layer emitting a yellow-green light and positioned between the first emitting material layer and the second electrode; and a first charge generation layer between the first emitting material layer and the second emitting material layer.

16. The organic light emitting device of claim 1, wherein a red pixel, a green pixel and a blue pixel are defined on the substrate, and the organic light emitting diode corresponds to each of the red pixel, the green pixel, and the blue pixel, and wherein the organic light emitting device further includes:

a color conversion layer disposed between the substrate and the organic light emitting diode or on the organic light emitting diode and corresponding to the red pixel and the green pixel.

17. The organic light emitting device of claim 1, wherein the electron blocking material is one of compounds in Formula 6-1:

[Formula 6-1]

EBL-1

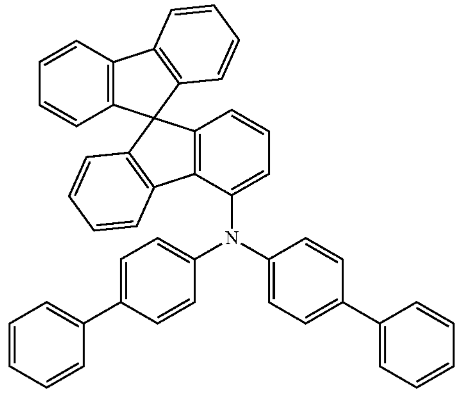

EBL-2

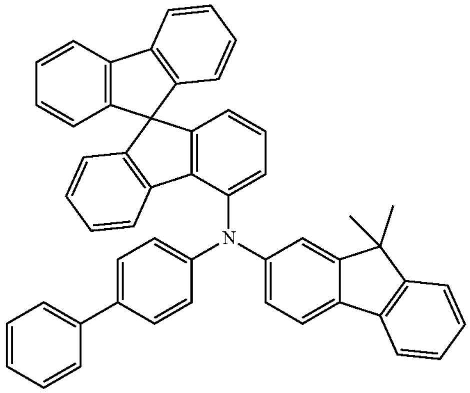

EBL-3

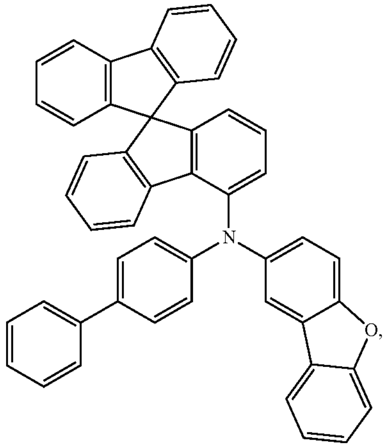

and wherein the hole blocking material is represented by Formula 8-1:

[Formula 8-1]
E1
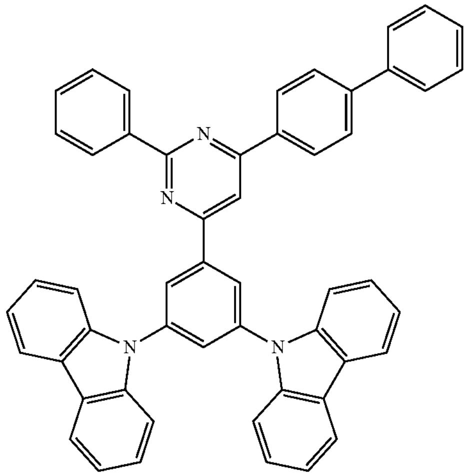
F1
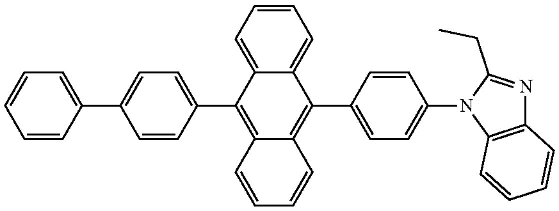
.
* * * * *